(12) United States Patent
Vescovi et al.

(10) Patent No.: US 9,078,857 B2
(45) Date of Patent: Jul. 14, 2015

(54) COMPOSITIONS COMPRISING INHIBITORS OF EPH RECEPTOR EXPRESSION IN TUMOR STEM CELLS AND METHODS OF TREATMENT THEREOF

(75) Inventors: Angelo Luigi Vescovi, Maroggia (CH); Elena Binda, Bergamo (IT)

(73) Assignee: StemGen S.P.A., Milan (IT)

( * ) Notice: Subject to any disclaimer, the term of this patent is extended or adjusted under 35 U.S.C. 154(b) by 0 days.

(21) Appl. No.: 13/089,217

(22) Filed: Apr. 18, 2011

(65) Prior Publication Data
US 2012/0083454 A1 Apr. 5, 2012

(30) Foreign Application Priority Data
Oct. 1, 2010 (EP) .................................. 10185930

(51) Int. Cl.
A61K 38/00 (2006.01)
A61P 35/00 (2006.01)
A61K 38/17 (2006.01)

(52) U.S. Cl.
CPC .................................. *A61K 38/177* (2013.01)

(58) Field of Classification Search
None
See application file for complete search history.

(56) References Cited

U.S. PATENT DOCUMENTS

| | | | | |
|---|---|---|---|---|
| 7,659,374 B2* | 2/2010 | Wu et al. | ..................... | 530/387.1 |
| 2005/0281783 A1* | 12/2005 | Kinch et al. | ................. | 424/93.2 |
| 2007/0248628 A1* | 10/2007 | Keller et al. | ............... | 424/277.1 |
| 2009/0123371 A1 | 5/2009 | Debinski et al. | | |
| 2010/0183618 A1 | 7/2010 | Hasegawa et al. | | |

OTHER PUBLICATIONS

Pasquale EB. Nature 10:165-180, Mar. 2010.*
PL Aló, et al. Immunohistochemical study of fatty acid synthase, Ki67, proliferating cell nuclear antigen, and p53 expression in hyperplastic parathyroids. Ann Diagn Pathol 3:287-293 (1999).
Amendola M, et al. Coordinate dual-gene transgeness by lentiviral vectors carrying synthetic bidirectional promoters. Nat Biotechnol 23:108-16 (2005).
Erba E, et al. Ecteinascidin-743 (ET-743), a natural marine compound, with a unique mechanism of action. Eur J Cancer; 37:97-105 (2001).
Gale NW, et al. Ephrins and their receptors: a repulsive topic?. Cell Tissue Res 290:227-41 (1997).
Galli R, et al. Isolation and characterization of tumorigenic, stem-like neural precursors from human glioblastoma. Cancer Res; 64(19): 7011-21 (2004).
Gritti A, et al. Multipotential stem cells from the adult mouse brain proliferate and self-renew in response to basic fibroblast growth factor. J Neurosci 16:1091-1100 (1996).
Gritti A, et al. Cultures of Stem Cells of the Central Nervous System, Humana Press Edition: S. Fedoroff (2001).
Jenkins DE, et al. Bioluminescent human breast cancer cell lines that permit rapid and sensitive in vivo detection of mammary tumors and multiple metastases in immune deficient mice. Breast Cancer Res; 5:R444-54 (2005).
Holland EC. Glioblastoma multiforme: the terminator. Proc Natl Acad Sci U S A 97:6242-4 (2000).
Pennacchietti S, et al. Hypoxia promotes invasive growth by transcriptional activation of the met proto oncogene. Cancer Cell 3:347-361 (2003).
Piccirillo SG, et al. Bone morphogenetic proteins inhibit the tumorigenic potential of human brain tumor-initiating cells. Nature; 444(7120): 761-5 (2006).
Stupp R, et al. Radiotherapy plus concomitant and adjuvant temozolomide for glioblastoma. N Engl J Med; 352(10):987-96 (2005).
Vescovi AL, et al. Isolation and cloning of multipotential stem cells from the embryonic human CNS and establishment of transplantable human neural stem cell lines by epigenetic stimulation. Exp Neurol 156:71-83 (1999).
Wykosky J, et al. A novel, potent, and specific ephrinA1-based cytotoxin against EphA2 receptor-expressing tumor cells. Mol Cancer Ther doi: 10.1158/1535-7163.MCT-07-0200 (2007) 6; 3208.
Li JJ, et al. EphrinA5 acts as a tumor suppressor in glioma by negative regulation of epidermal growth factor receptor. Oncogene 28, 1759-1768 (2009).
Wykosky J, et al. EphA2 as a Novel Molecular Marker and Target in Glioblastoma Multiforme. Mol Cancer Res 2005;3(10) Oct. 2005.
Vescovi, A.L., et al., Ephrins regulate the activity of cancer stem cells from human glioblastomas, FENS Forum 2010, Apr. 7, 2010, Amsterdam, Netherlands.
Vescovi, A.L., et al., Recent advances in regulatory mechanisms of human GBM cancer stem cells, Updates in neuro-oncology, Brain Tumor Symposium Jul. 2-4, 2010, Cortona, Italy.
Vescovi, A.L., et al., Ephrins inhibit tumorigenicity in cancer stem cells of human glioblastomas, The 18th International Conference on Brain Tumor Research Therapy, May 18-20, 2010, Travemünde, Germany.
EPO Search Report of European Application 10 18 5930 in the name of Stemgen, S.P.A., (search date Apr. 26, 2011).
1-Binda, E. et al., *The EphA2 Receptor Drives Self-Renewal and Tumorigenicity in Stem-like Tumor-Propagating Cells from Human Glioblastomas*, Cancer Cell, 2012, 22, pp. 765-780.
2-Pasquale, E., *Eph-Ephrin Bidirectional Signaling in Physiology and Disease*, Cell, 2008, 133, pp. 38-52.
1-Brantley, D.M. et al. *Soluble Eph A receptors inhibit tumor angiogenesis and progression in vivo.* Oncogene, 21, pp. 7011-7026, 2002.
2-Hatano, M. et al. *EphA2 as a Glioma-Associated Antigen: A Novel Target for Glioma Vaccines.* Neoplasia, vol. 7 (8), pp. 717-722, Aug. 2005.
Lin-Fang Wang et al., Increased Expression of EphA2 Correlates with Adverse Outcome in Primary and Recurrent Glioblastoma Multiforme Patients, Oncology Reports 19: 151-156, 2008.

* cited by examiner

*Primary Examiner* — Robert Landsman
(74) *Attorney, Agent, or Firm* — Beverly W. Lubit

(57) ABSTRACT

The present disclosure concerns the field of malignant tumors of the central nervous system and provides pharmaceutical compositions suitable for the therapeutic and for the prophylactic treatment of brain tumors and for inhibiting the growth of the tumor mass.

15 Claims, 35 Drawing Sheets

| Genes | Controls | | GBM-CSCs | |
|---|---|---|---|---|
| | U87 | HNSCs | #1 | #7 |
| RECEPTORS | | | | |
| EphA1 | - | + | + | - |
| EphA2 | + | + | + | + |
| EphA3 | - | + | faint | + |
| EphA4 | + | + | + | + |
| EphA5 | + | - | - | - |
| EphA7 | + | + | - | - |
| EphA8 | - | - | - | - |
| EphA10 | - | - | - | - |
| EphB1 | - | - | - | - |
| EphB2 | + | + | + | + |
| EphB3 | + | + | + | + |
| EphB4 | + | + | + | + |
| EphB6 | + | + | + | - |
| LIGANDS | | | | |
| EFNA1 | - | + | + | + |
| EFNA2 | - | faint | + | - |
| EFNA3 | + | + | + | + |
| EFNA4 | + | + | + | + |
| EFNA5 | - | - | - | - |
| EFNB1 | + | + | + | + |
| EFNB2 | + | + | + | faint |
| EFNB3 | - | + | + | faint |

Fig. 1A

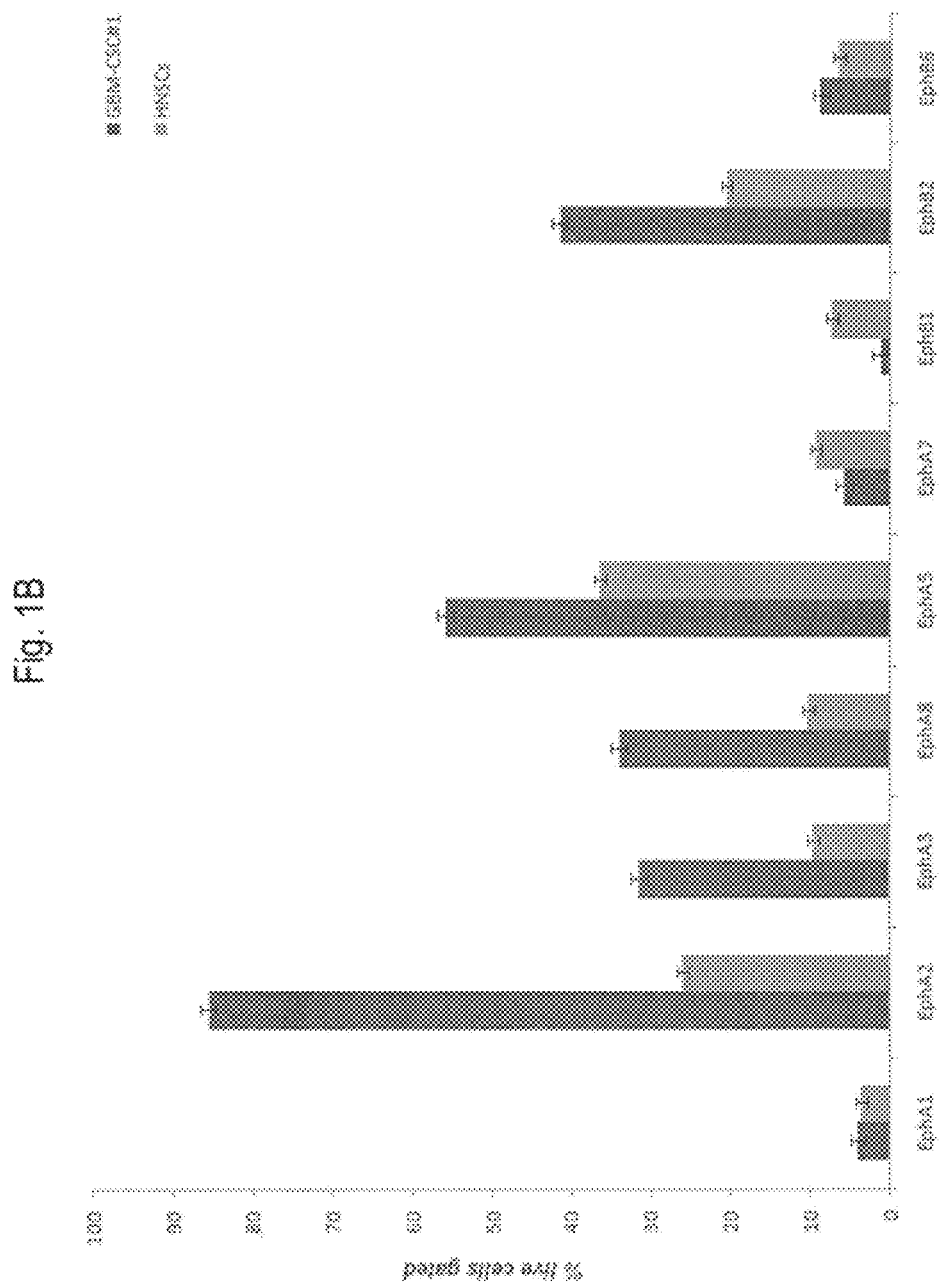

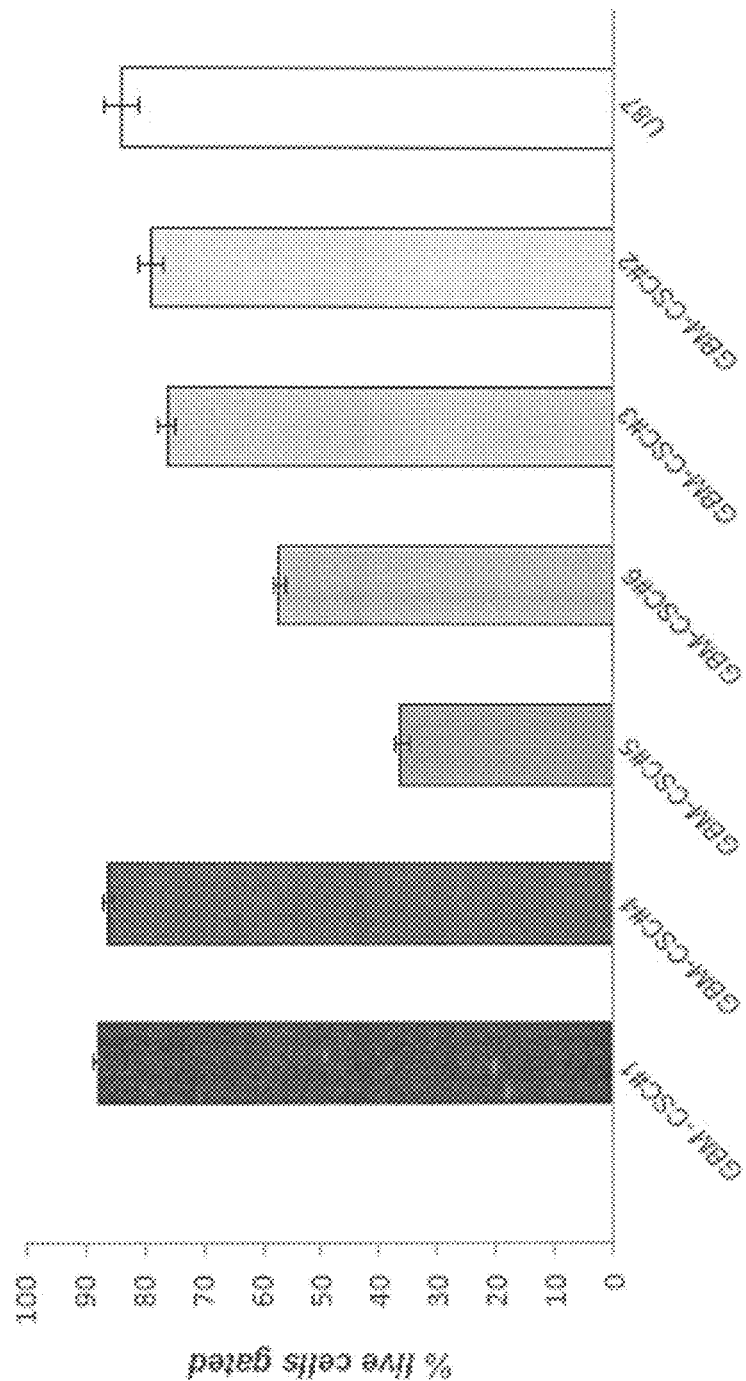

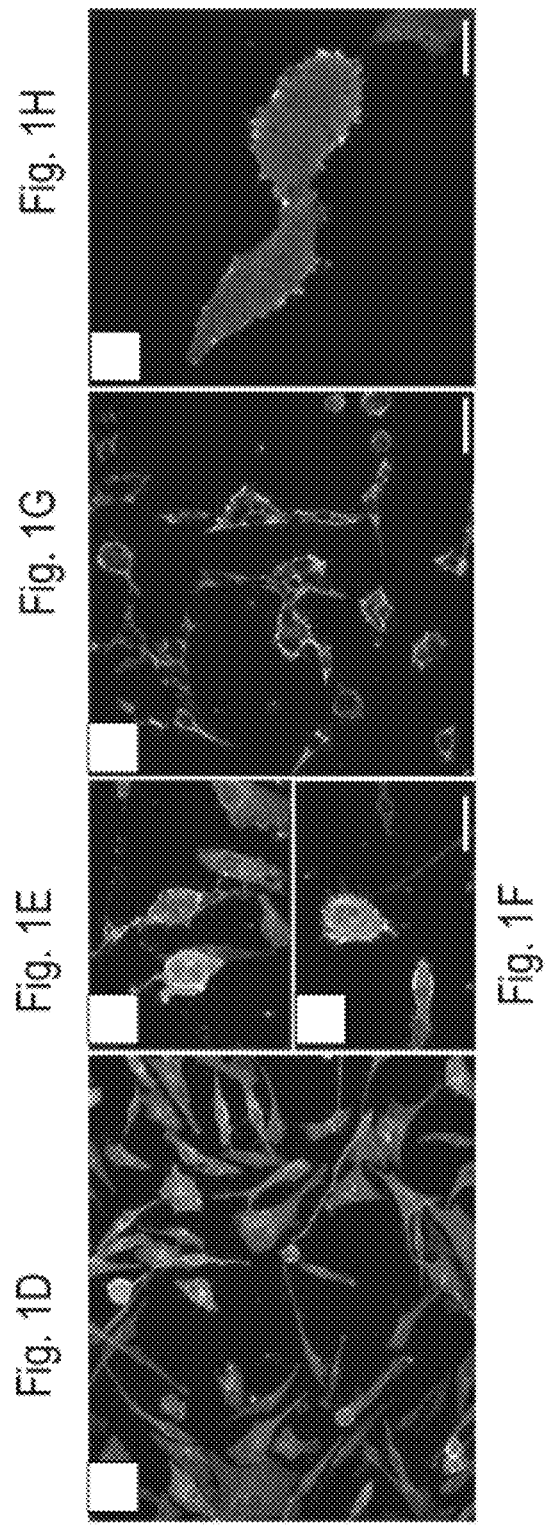

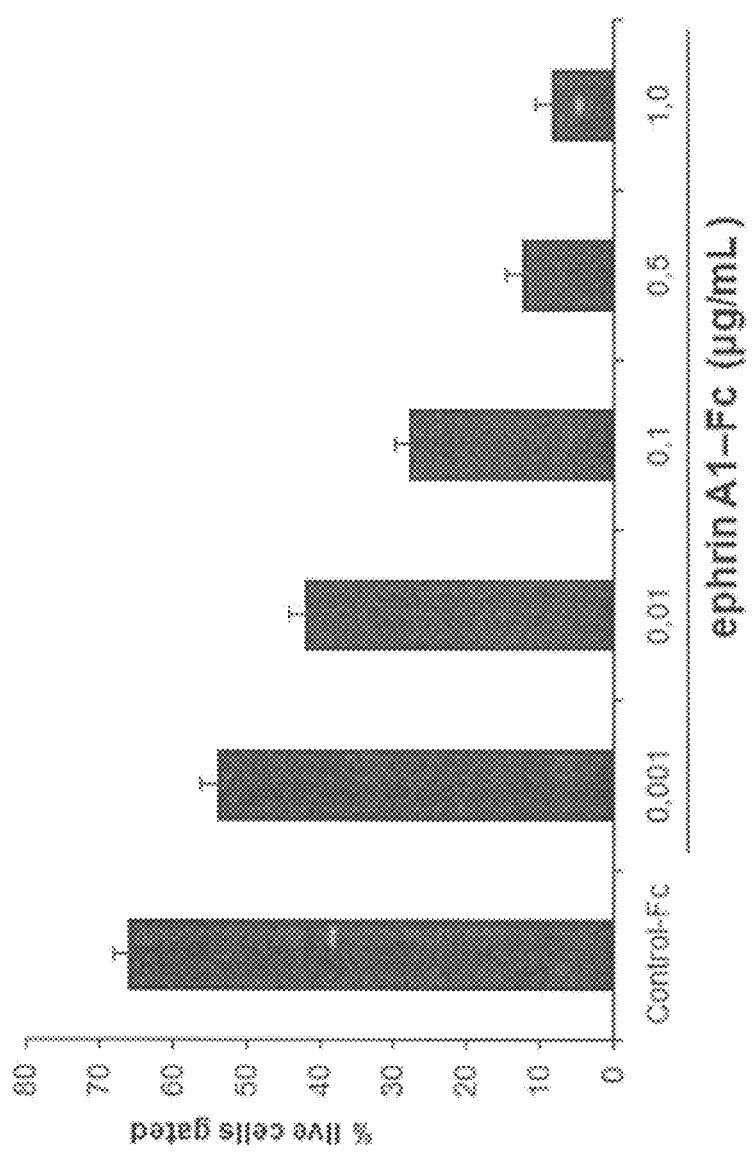

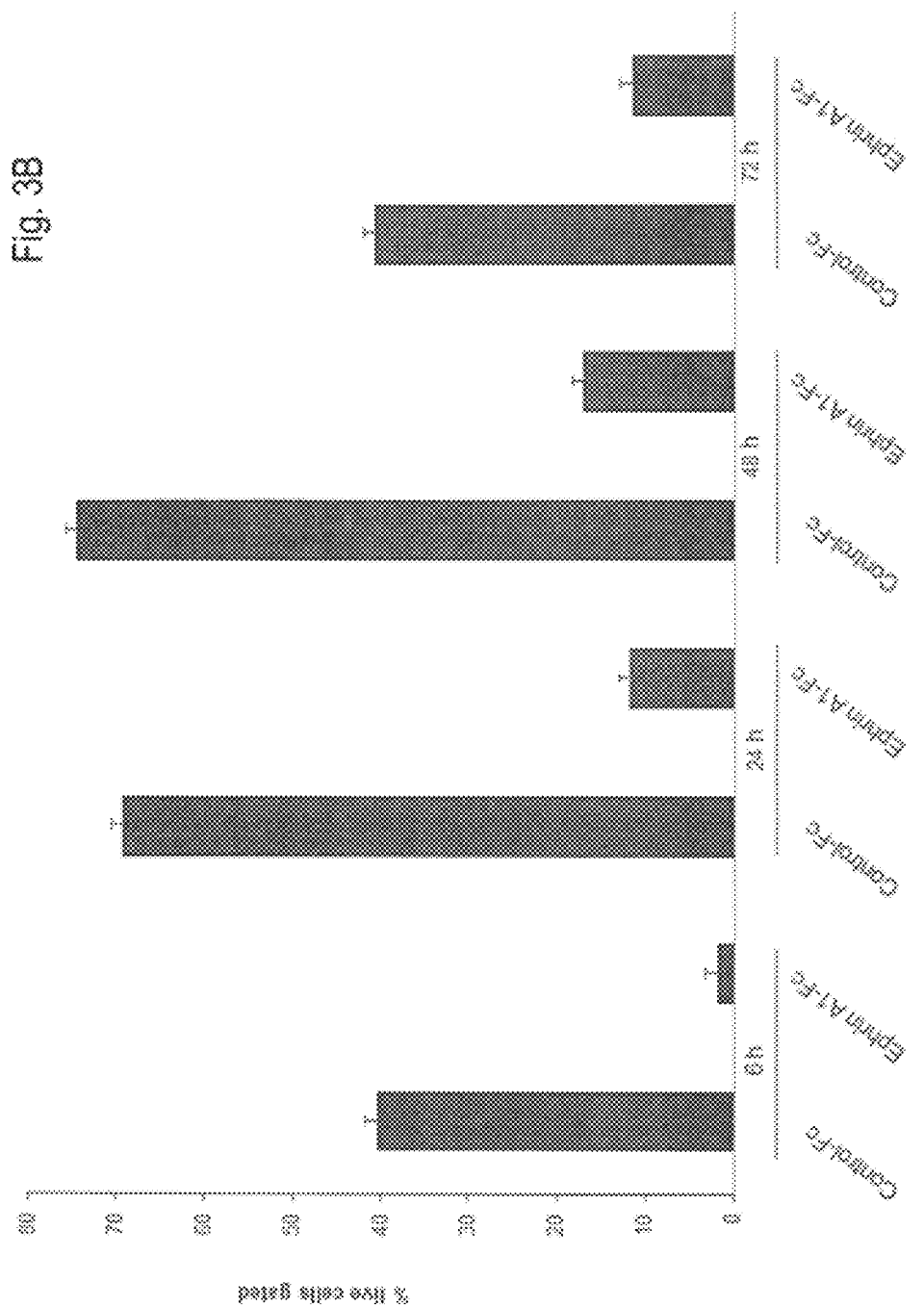

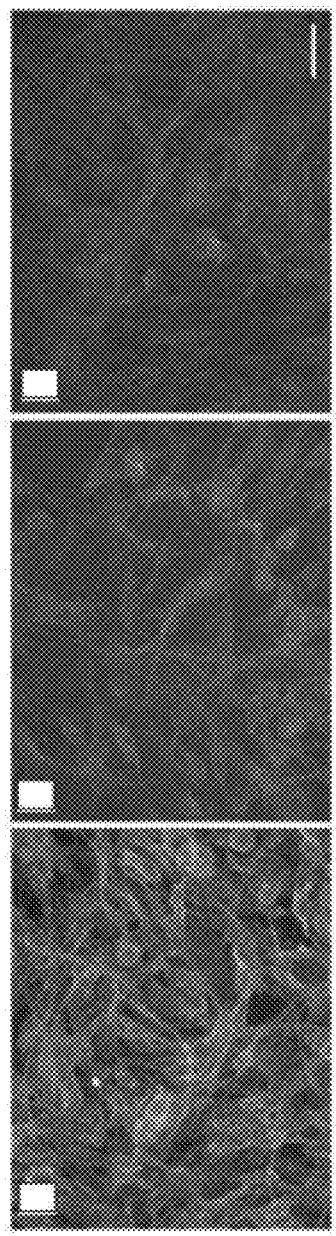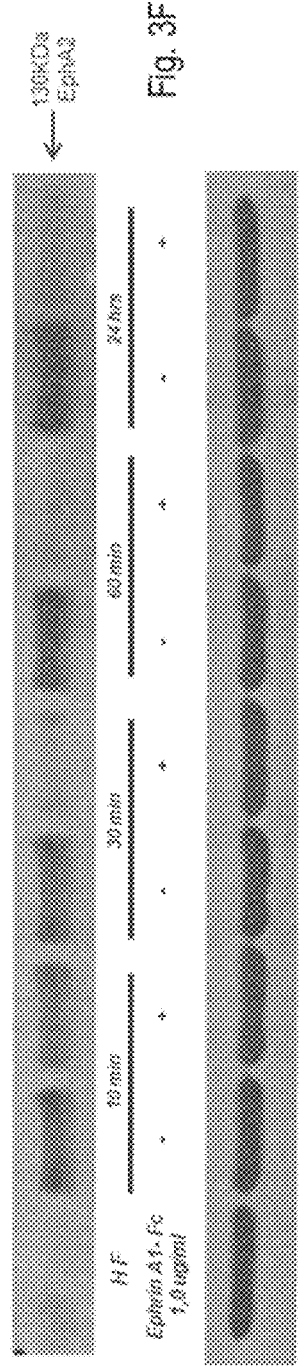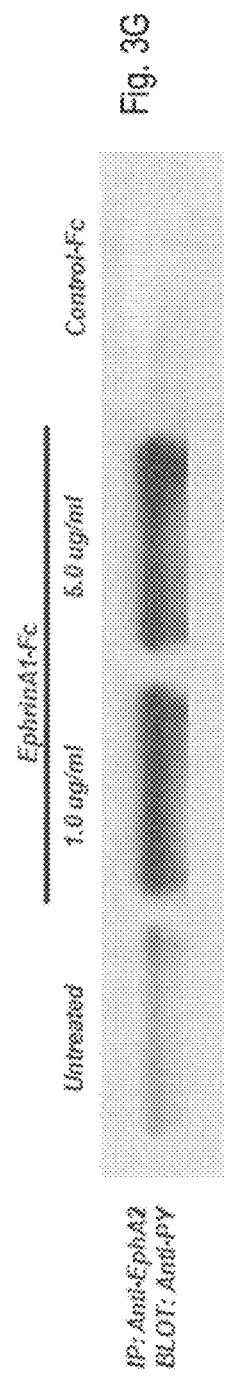

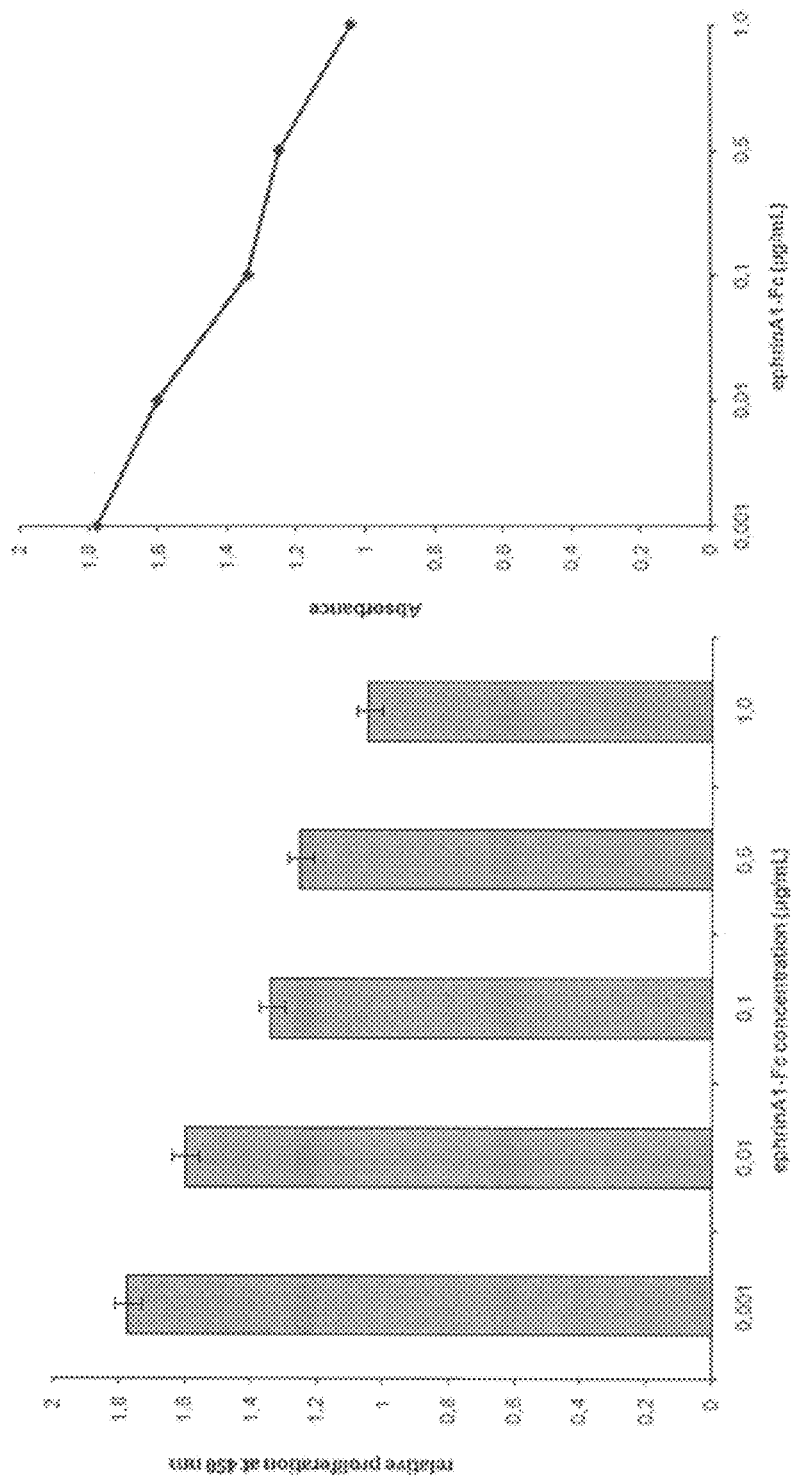

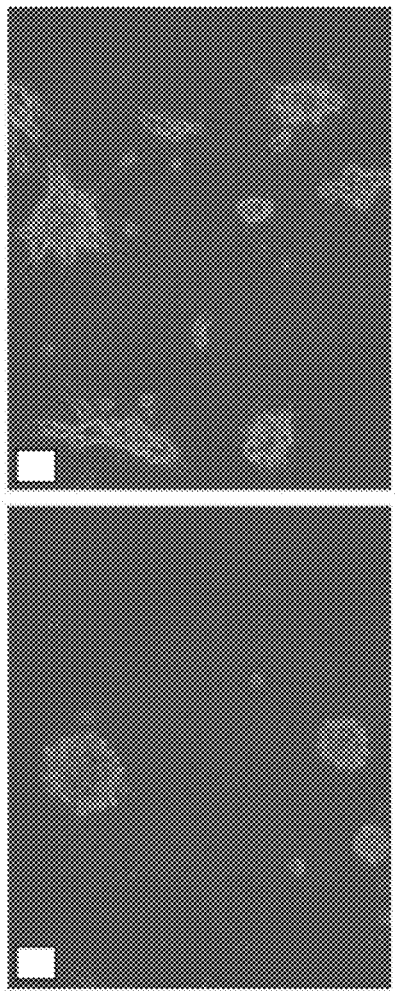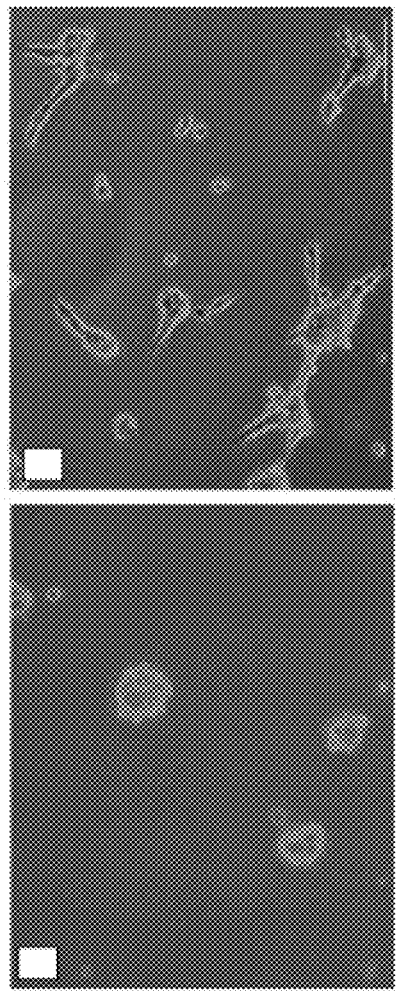
Fig. 4L
Fig. 4M
Fig. 4J
Fig. 4K

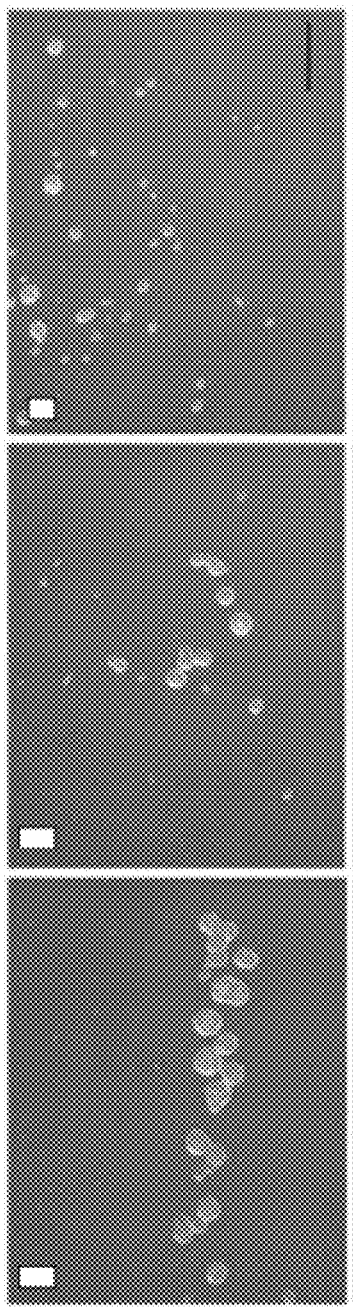
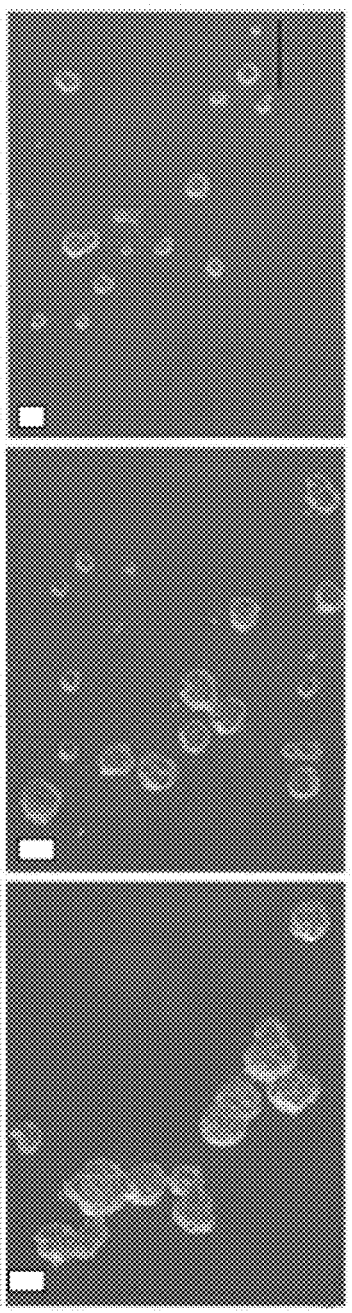

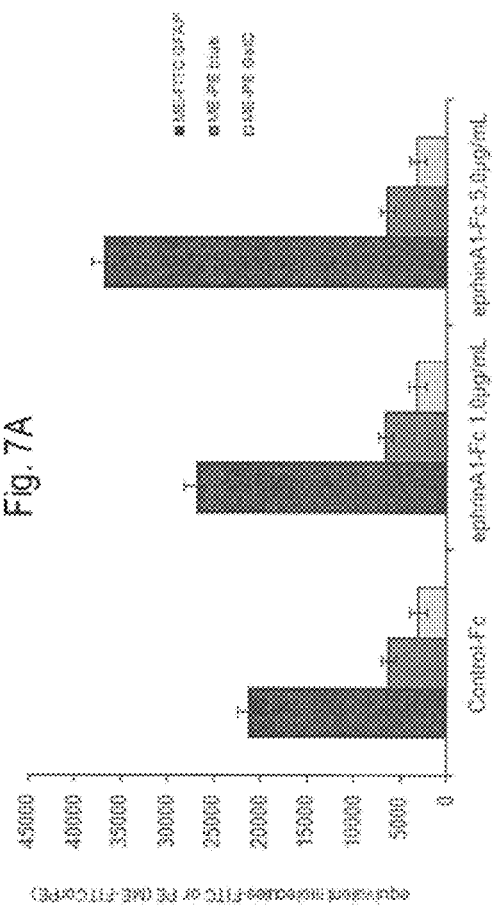
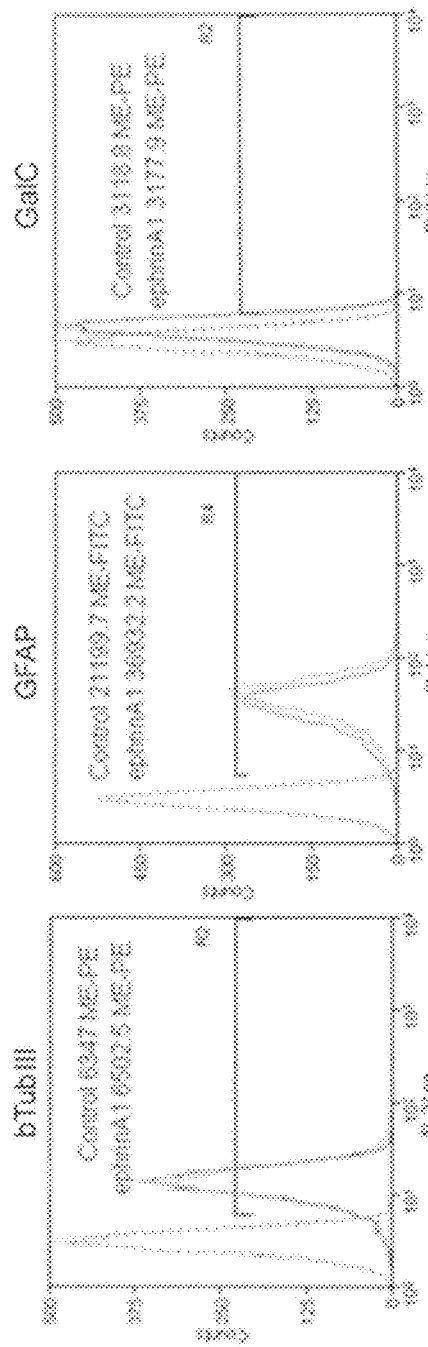

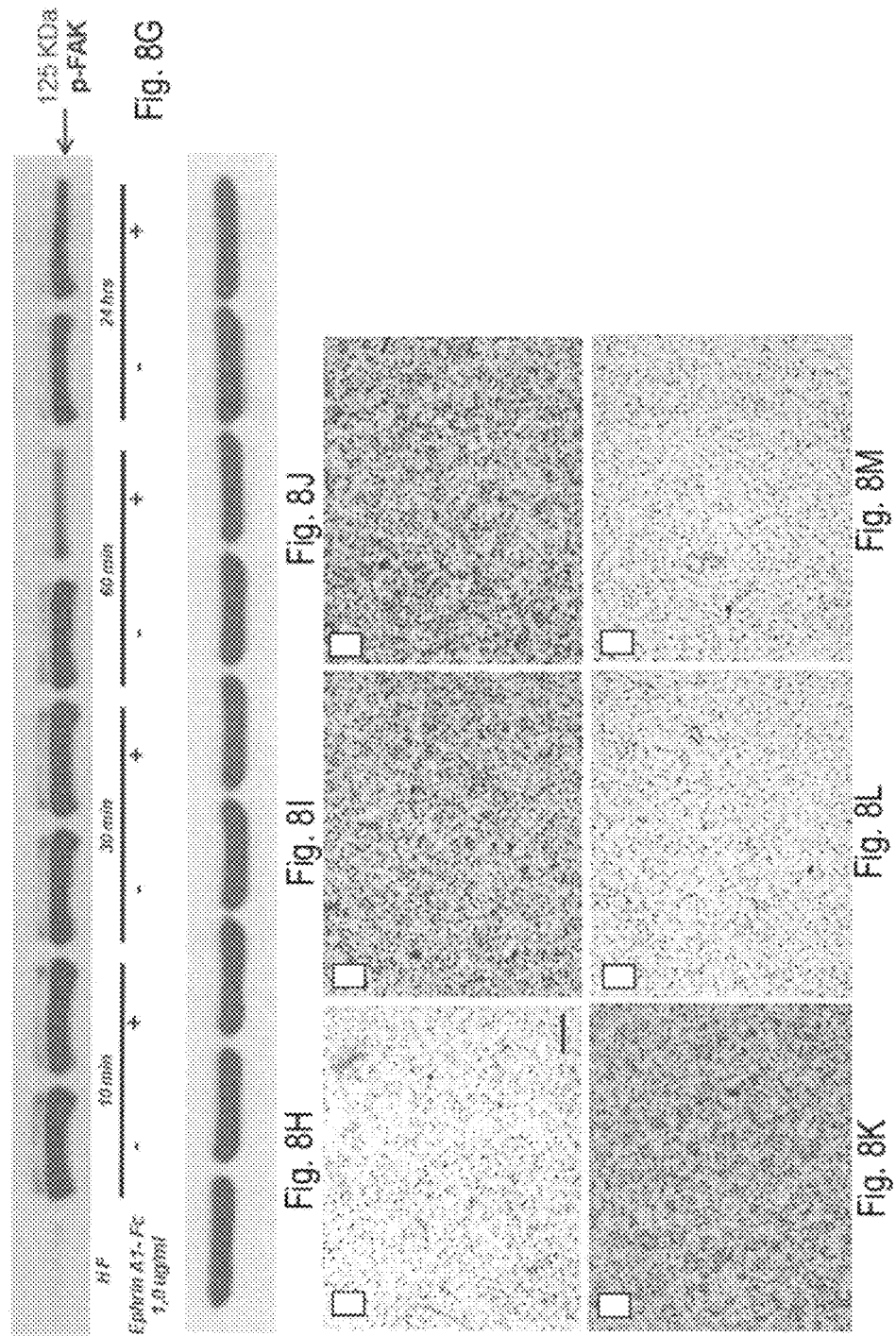

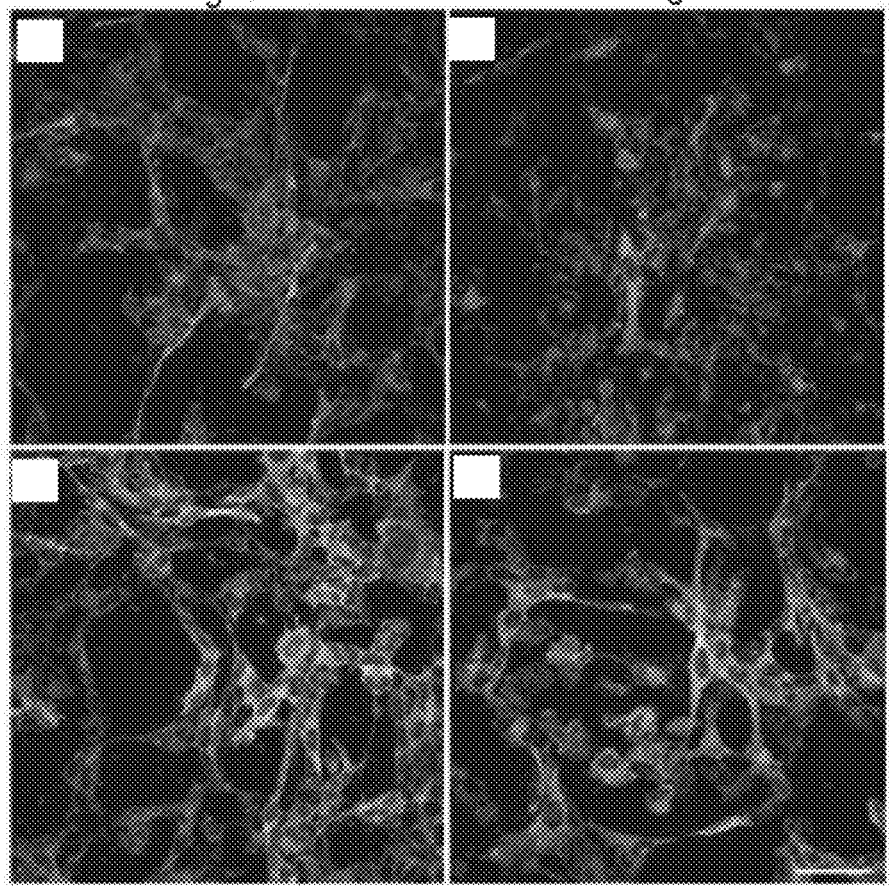
Fig. 8N  Fig. 8P
Fig. 8O  Fig. 8Q
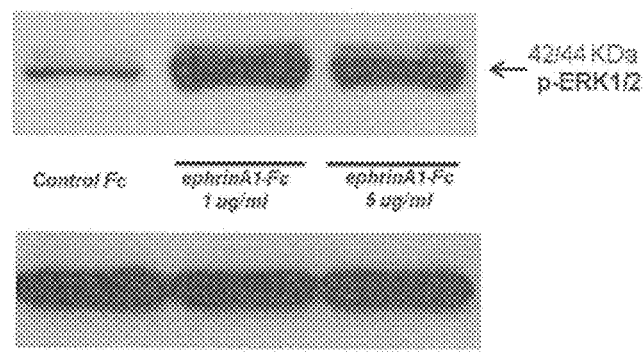
Fig. 8R

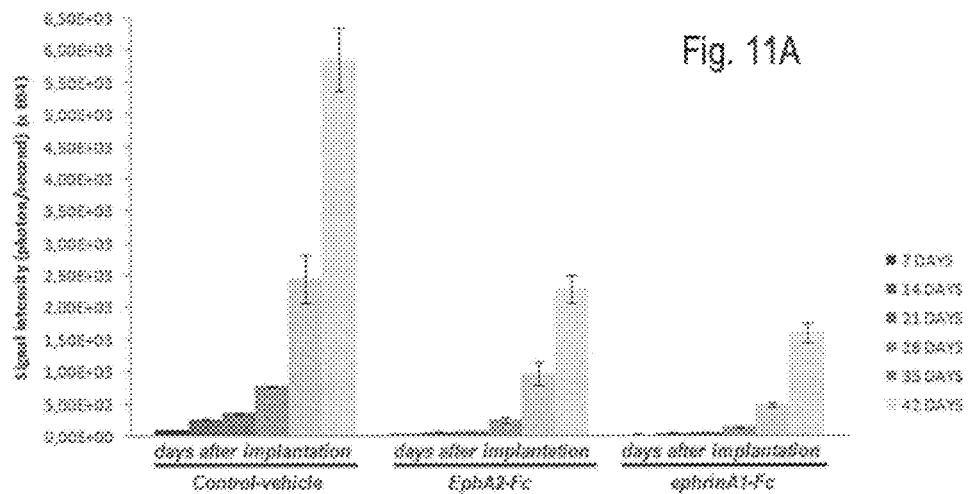
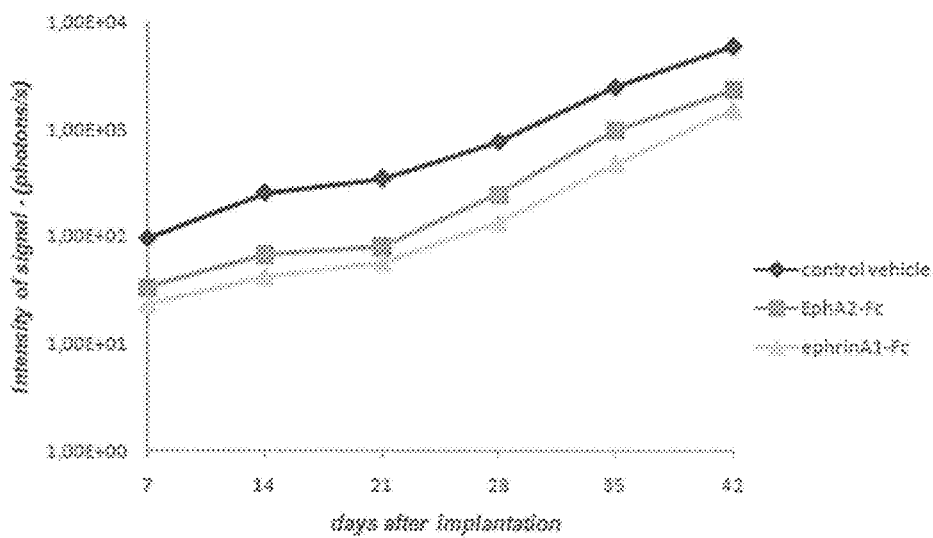
Fig. 11B

```
                          SEQUENCE LISTING

<160> NUMBER OF SEQ ID NOS: 4

<210> SEQ ID NO 1
<211> LENGTH: 205
<212> TYPE: PRT
<213> ORGANISM: Homo sapiens

<400> SEQUENCE: 1

Met Glu Phe Leu Trp Ala Pro Leu Leu Gly Leu Cys Cys Ser Leu Ala
1               5                   10                  15

Ala Ala Asp Arg His Thr Val Phe Trp Asn Ser Ser Asn Pro Lys Phe
            20                  25                  30

Arg Asn Glu Asp Tyr Thr Ile His Val Gln Leu Asn Asp Tyr Val Asp
        35                  40                  45

Ile Ile Cys Pro His Tyr Glu Asp His Ser Val Ala Asp Ala Ala Met
    50                  55                  60

Glu Gln Tyr Ile Leu Tyr Leu Val Glu His Glu Glu Tyr Gln Leu Cys
65                  70                  75                  80

Gln Pro Gln Ser Lys Asp Gln Val Arg Trp Gln Cys Asn Arg Pro Ser
                85                  90                  95

Ala Lys His Gly Pro Glu Lys Leu Ser Glu Lys Phe Gln Arg Phe Thr
            100                 105                 110

Pro Phe Thr Leu Gly Lys Glu Phe Lys Glu Gly His Ser Tyr Tyr Tyr
        115                 120                 125

Ile Ser Lys Pro Ile His Gln His Glu Asp Arg Cys Leu Arg Leu Lys
    130                 135                 140

Val Thr Val Ser Gly Lys Ile Thr His Ser Pro Gln Ala His Asp Asn
145                 150                 155                 160

Pro Gln Glu Lys Arg Leu Ala Ala Asp Asp Pro Glu Val Arg Val Leu
                165                 170                 175

His Ser Ile Gly His Ser Ala Ala Pro Arg Leu Phe Pro Leu Ala Trp
            180                 185                 190

Thr Val Leu Leu Leu Pro Leu Leu Leu Leu Gln Thr Pro
        195                 200                 205

<210> SEQ ID NO 2
<211> LENGTH: 1590
<212> TYPE: DNA
<213> ORGANISM: Homo sapiens

<400> SEQUENCE: 2
gccagatctg tgagcccagc gctgactgcg ccgcggagaa agccagtggg aacccagacc      60
cataggagac ccgcgtcccc gctcggcctg gccaggcccc gcgctatgga gttcctctgg     120
gcccctctct tgggtctgtg ctgcagtctg gccgctgctg atcgccacac cgtcttctgg     180
aacagttcaa atcccaagtt ccggaatgag gactacacca tacatgtgca gctgaatgac     240
tacgtggaca tcatctgtcc gcactatgaa gatcactctg tggcagacgc tgccatggag     300
cagtacatac tgtacctggt ggagcatgag gagtaccagc tgtgccagcc ccagtccaag     360
gaccaagtcc gctggcagtg caaccggccc agtgccaagc atggcccgga gaagctgtct     420
gagaagttcc agcgcttcac acctttcacc ctgggcaagg agttcaaaga aggacacagc     480
```

```
tactactaca tctccaaacc catccaccag catgaagacc gctgcttgag gttgaaggtg      540
actgtcagtg gcaaaatcac tcacagtcct caggcccatg acaatccaca ggagaagaga      600
cttgcagcag atgacccaga ggtgcgggtt ctacatagca tcggtcacag tgctgcccca      660
cgcctcttcc cacttgcctg gactgtgctg ctccttccac ttctgctgct gcaaaccccg      720
tgaaggtgta tgccacacct ggccttaaag agggacaggc tgaagagagg gacaggcact      780
ccaaacctgt cttggggcca ctttcagagc cccagccct gggaaccact cccaccacag       840
gcataagcta tcacctagca gcctcaaaac gggtcagtat taaggttttc aaccggaagg      900
aggccaacca gcccgacagt gccatcccca ccttcacctc ggagggatgg agaaagaagt      960
ggagacagtc ctttcccacc attcctgcct ttaagccaaa gaaacaagct gtgcaggcat     1020
ggtcccttaa ggcacagtgg gagctgagct ggaaggggcc acgtggatgg caaagcttg     1080
tcaaagatgc ccctccagg agagagccag gatgcccaga tgaactgact gaaggaaaag     1140
caagaaacag tttcttgctt ggaagccagg tacaggagag gcagcatgct tgggctgacc     1200
cagcatctcc cagcaagacc tcatctgtgg agctgccaca gagaagtttg tagccaggta     1260
ctgcattctc tcccatcctg gggcagcact ccccagagct gtgccagcag ggggctgtg      1320
ccaacctgtt cttagagtgt agctgtaagg gcagtgccca tgtgtacatt ctgcctagag     1380
tgtagcctaa agggcagggc ccacgtgtat agtatctgta tataagttgc tgtgtgtctg     1440
tcctgatttc tacaactgga gttttttat acaatgttct ttgtctcaaa ataaagcaat      1500
gtgttttttc ggacatgctt ttctgccact ccatattaaa acatatgacc attgagtccc     1560
tgctaaaaaa aaaaaaaaaa aaaaaaaaaa                                       1590

<210> SEQ ID NO 3
<211> LENGTH: 976
<212> TYPE: PRT
<213> ORGANISM: Homo sapiens

<400> SEQUENCE: 3

Met Glu Leu Gln Ala Ala Arg Ala Cys Phe Ala Leu Leu Trp Gly Cys
1               5                   10                  15

Ala Leu Ala Ala Ala Ala Ala Gln Gly Lys Glu Val Val Leu Leu
                20                  25                  30

Asp Phe Ala Ala Ala Gly Gly Glu Leu Gly Trp Leu Thr His Pro Tyr
        35                  40                  45

Gly Lys Gly Trp Asp Leu Met Gln Asn Ile Met Asn Asp Met Pro Ile
    50                  55                  60

Tyr Met Tyr Ser Val Cys Asn Val Met Ser Gly Asp Gln Asp Asn Trp
65                  70                  75                  80

Leu Arg Thr Asn Trp Val Tyr Arg Gly Glu Ala Glu Arg Ile Phe Ile
                85                  90                  95

Glu Leu Lys Phe Thr Val Arg Asp Cys Asn Ser Phe Pro Gly Gly Ala
                100                 105                 110

Ser Ser Cys Lys Glu Thr Phe Asn Leu Tyr Tyr Ala Glu Ser Asp Leu
            115                 120                 125

Asp Tyr Gly Thr Asn Phe Gln Lys Arg Leu Phe Thr Lys Ile Asp Thr
        130                 135                 140

Ile Ala Pro Asp Glu Ile Thr Val Ser Ser Asp Phe Glu Ala Arg His
145                 150                 155                 160

Val Lys Leu Asn Val Glu Glu Arg Ser Val Gly Pro Leu Thr Arg Lys
                165                 170                 175
```

-continued

```
Gly Phe Tyr Leu Ala Phe Gln Asp Ile Gly Ala Cys Val Ala Leu Leu
                180                 185                 190

Ser Val Arg Val Tyr Tyr Lys Lys Cys Pro Glu Leu Leu Gln Gly Leu
            195                 200                 205

Ala His Phe Pro Glu Thr Ile Ala Gly Ser Asp Ala Pro Ser Leu Ala
        210                 215                 220

Thr Val Ala Gly Thr Cys Val Asp His Ala Val Pro Pro Gly Gly
225                 230                 235                 240

Glu Glu Pro Arg Met His Cys Ala Val Asp Gly Glu Trp Leu Val Pro
                245                 250                 255

Ile Gly Gln Cys Leu Cys Gln Ala Gly Tyr Glu Lys Val Glu Asp Ala
            260                 265                 270

Cys Gln Ala Cys Ser Pro Gly Phe Phe Lys Phe Glu Ala Ser Glu Ser
        275                 280                 285

Pro Cys Leu Glu Cys Pro Glu His Thr Leu Pro Ser Pro Glu Gly Ala
        290                 295                 300

Thr Ser Cys Glu Cys Glu Glu Gly Phe Phe Arg Ala Pro Gln Asp Pro
305                 310                 315                 320

Ala Ser Met Pro Cys Thr Arg Pro Pro Ser Ala Pro His Tyr Leu Thr
                325                 330                 335

Ala Val Gly Met Gly Ala Lys Val Glu Leu Arg Trp Thr Pro Pro Gln
            340                 345                 350

Asp Ser Gly Gly Arg Glu Asp Ile Val Tyr Ser Val Thr Cys Glu Gln
        355                 360                 365

Cys Trp Pro Glu Ser Gly Glu Cys Gly Pro Cys Glu Ala Ser Val Arg
        370                 375                 380

Tyr Ser Glu Pro Pro His Gly Leu Thr Arg Thr Ser Val Thr Val Ser
385                 390                 395                 400

Asp Leu Glu Pro His Met Asn Tyr Thr Phe Thr Val Glu Ala Arg Asn
                405                 410                 415

Gly Val Ser Gly Leu Val Thr Ser Arg Ser Phe Arg Thr Ala Ser Val
            420                 425                 430

Ser Ile Asn Gln Thr Glu Pro Pro Lys Val Arg Leu Glu Gly Arg Ser
        435                 440                 445

Thr Thr Ser Leu Ser Val Ser Trp Ser Ile Pro Pro Pro Gln Gln Ser
        450                 455                 460

Arg Val Trp Lys Tyr Glu Val Thr Tyr Arg Lys Lys Gly Asp Ser Asn
465                 470                 475                 480

Ser Tyr Asn Val Arg Arg Thr Glu Gly Phe Ser Val Thr Leu Asp Asp
                485                 490                 495

Leu Ala Pro Asp Thr Thr Tyr Leu Val Gln Val Gln Ala Leu Thr Gln
            500                 505                 510

Glu Gly Gln Gly Ala Gly Ser Lys Val His Glu Phe Gln Thr Leu Ser
        515                 520                 525

Pro Glu Gly Ser Gly Asn Leu Ala Val Ile Gly Gly Val Ala Val Gly
        530                 535                 540

Val Val Leu Leu Leu Val Leu Ala Gly Val Gly Phe Phe Ile His Arg
545                 550                 555                 560

Arg Arg Lys Asn Gln Arg Ala Arg Gln Ser Pro Glu Asp Val Tyr Phe
                565                 570                 575

Ser Lys Ser Glu Gln Leu Lys Pro Leu Lys Thr Tyr Val Asp Pro His
            580                 585                 590

Thr Tyr Glu Asp Pro Asn Gln Ala Val Leu Lys Phe Thr Thr Glu Ile
```

His Pro Ser Cys Val Thr Arg Gln Lys Val Ile Gly Ala Gly Glu Phe
              610                 615                 620

Gly Glu Val Tyr Lys Gly Met Leu Lys Thr Ser Ser Gly Lys Lys Glu
625                 630                 635                 640

Val Pro Val Ala Ile Lys Thr Leu Lys Ala Gly Tyr Thr Glu Lys Gln
                    645                 650                 655

Arg Val Asp Phe Leu Gly Glu Ala Gly Ile Met Gly Gln Phe Ser His
                660                 665                 670

His Asn Ile Ile Arg Leu Glu Gly Val Ile Ser Lys Tyr Lys Pro Met
            675                 680                 685

Met Ile Ile Thr Glu Tyr Met Glu Asn Gly Ala Leu Asp Lys Phe Leu
        690                 695                 700

Arg Glu Lys Asp Gly Glu Phe Ser Val Leu Gln Leu Val Gly Met Leu
705                 710                 715                 720

Arg Gly Ile Ala Ala Gly Met Lys Tyr Leu Ala Asn Met Asn Tyr Val
                    725                 730                 735

His Arg Asp Leu Ala Ala Arg Asn Ile Leu Val Asn Ser Asn Leu Val
                740                 745                 750

Cys Lys Val Ser Asp Phe Gly Leu Ser Arg Val Leu Glu Asp Asp Pro
            755                 760                 765

Glu Ala Thr Tyr Thr Thr Ser Gly Gly Lys Ile Pro Ile Arg Trp Thr
        770                 775                 780

Ala Pro Glu Ala Ile Ser Tyr Arg Lys Phe Thr Ser Ala Ser Asp Val
785                 790                 795                 800

Trp Ser Phe Gly Ile Val Met Trp Glu Val Met Thr Tyr Gly Glu Arg
                    805                 810                 815

Pro Tyr Trp Glu Leu Ser Asn His Glu Val Met Lys Ala Ile Asn Asp
                820                 825                 830

Gly Phe Arg Leu Pro Thr Pro Met Asp Cys Pro Ser Ala Ile Tyr Gln
            835                 840                 845

Leu Met Met Gln Cys Trp Gln Gln Glu Arg Ala Arg Arg Pro Lys Phe
        850                 855                 860

Ala Asp Ile Val Ser Ile Leu Asp Lys Leu Ile Arg Ala Pro Asp Ser
865                 870                 875                 880

Leu Lys Thr Leu Ala Asp Phe Asp Pro Arg Val Ser Ile Arg Leu Pro
                    885                 890                 895

Ser Thr Ser Gly Ser Glu Gly Val Pro Phe Arg Thr Val Ser Glu Trp
                900                 905                 910

Leu Glu Ser Ile Lys Met Gln Gln Tyr Thr Glu His Phe Met Ala Ala
            915                 920                 925

Gly Tyr Thr Ala Ile Glu Lys Val Val Gln Met Thr Asn Asp Asp Ile
        930                 935                 940

Lys Arg Ile Gly Val Arg Leu Pro Gly His Gln Lys Arg Ile Ala Tyr
945                 950                 955                 960

Ser Leu Leu Gly Leu Lys Asp Gln Val Asn Thr Val Gly Ile Pro Ile
                    965                 970                 975

<210> SEQ ID NO 4
<211> LENGTH: 3970
<212> TYPE: DNA
<213> ORGANISM: Homo sapiens

<400> SEQUENCE: 4

-continued

| | |
|---|---|
| ggttctcacc caacttccat taaggactcg gggcaggagg ggcagaagtt gcgcgcaggc | 60 |
| cggcgggcgg gagcggacac cgaggccggc gtgcaggcgt gcgggtgtgc gggagccggg | 120 |
| ctcgggggga tcggaccgag agcgagaagc gcggcatgga gctccaggca gcccgcgcct | 180 |
| gcttcgccct gctgtgggc tgtgcgctgg ccgcggccgc ggcggcgcag ggcaaggaag | 240 |
| tggtactgct ggactttgct gcagctggag gggagctcgg ctggctcaca cacccgtatg | 300 |
| gcaaagggtg ggacctgatg cagaacatca tgaatgacat gccgatctac atgtactccg | 360 |
| tgtgcaacgt gatgtctggc gaccaggaca actggctccg caccaactgg gtgtaccgag | 420 |
| gagaggctga gcgtatcttc attgagctca agtttactgt acgtgactgc aacagcttcc | 480 |
| ctggtggcgc cagctcctgc aaggagactt tcaacctcta ctatgccgag tcggacctgg | 540 |
| actacggcac caacttccag aagcgcctgt tcaccaagat tgacaccatt gcgcccgatg | 600 |
| agatcaccgt cagcagcgac ttcgaggcac gccacgtgaa gctgaacgtg gaggagcgct | 660 |
| ccgtgggcc gctcacccgc aaaggcttct acctggcctt ccaggatatc ggtgcctgtg | 720 |
| tggcgctgct ctccgtccgt gtctactaca agaagtgccc cgagctgctg cagggcctgg | 780 |
| cccacttccc tgagaccatc gccggctctg atgcaccttc cctggccact gtggccggca | 840 |
| cctgtgtgga ccatgccgtg gtgccaccgg ggggtgaaga gccccgtatg cactgtgcag | 900 |
| tggatggcga gtggctggtg cccattgggc agtgcctgtg ccaggcaggc tacgagaagg | 960 |
| tggaggatgc ctgccaggcc tgctcgcctg gattttttaa gtttgaggca tctgagagcc | 1020 |
| cctgcttgga gtgccctgag cacacgctgc catcccctga gggtgccacc tcctgcgagt | 1080 |
| gtgaggaagg cttcttccgg gcacctcagg acccagcgtc gatgccttgc acacgacccc | 1140 |
| cctccgcccc acactacctc acagccgtgg gcatgggtgc caaggtggag ctgcgctgga | 1200 |
| cgccccctca ggacagcggg ggccgcgagg acattgtcta cagcgtcacc tgcgaacagt | 1260 |
| gctggcccga gtctggggaa tgcgggccgt gtgaggccag tgtgcgctac tcggagcctc | 1320 |
| ctcacggact gacccgcacc agtgtgacag tgagcgacct ggagcccac atgaactaca | 1380 |
| ccttcaccgt ggaggcccgc aatggcgtct caggcctggt aaccagccgc agcttccgta | 1440 |
| ctgccagtgt cagcatcaac cagacagagc ccccaaggt gaggctggag ggccgcagca | 1500 |
| ccacctcgct tagcgtctcc tggagcatcc cccgccgca gcagagccga gtgtggaagt | 1560 |
| acgaggtcac ttaccgcaag aagggagact ccaacagcta caatgtgcgc cgcaccgagg | 1620 |
| gtttctccgt gaccctggac gacctggccc cagacaccac ctacctggtc caggtgcagg | 1680 |
| cactgacgca ggagggccag ggggccggca gcaaggtgca cgaattccag acgctgtccc | 1740 |
| cggagggatc tggcaacttg gcggtgattg gcggcgtggc tgtcggtgtg gtcctgcttc | 1800 |
| tggtgctggc aggagttggc ttctttatcc accgcaggag gaagaaccag cgtgcccgcc | 1860 |
| agtccccgga ggacgtttac ttctccaagt cagaacaact gaagcccctg aagacatacg | 1920 |
| tggaccccca cacatatgag gaccccaacc aggctgtgtt gaagttcact accgagatcc | 1980 |
| atccatcctg tgtcactcgg cagaaggtga tcggagcagg agagtttggg gaggtgtaca | 2040 |
| agggcatgct gaagacatcc tcggggaaga aggaggtgcc ggtggccatc aagacgctga | 2100 |
| aagccggcta cacagagaag cagcgagtgg acttcctcgg cgaggccggc atcatgggcc | 2160 |
| agttcagcca ccacaacatc atccgcctag agggcgtcat ctccaaatac aagcccatga | 2220 |
| tgatcatcac tgagtacatg gagaatgggg ccctggacaa gttccttcgg gagaaggatg | 2280 |
| gcgagttcag cgtgctgcag ctggtgggca tgctgcgggg catcgcagct ggcatgaagt | 2340 |
| acctggccaa catgaactat gtgcaccgtg acctggctgc ccgcaacatc ctcgtcaaca | 2400 |

```
gcaacctggt ctgcaaggtg tctgactttg gcctgtcccg cgtgctggag gacgaccccg    2460
aggccaccta caccaccagt ggcggcaaga tccccatccg ctggaccgcc ccggaggcca    2520
tttcctaccg gaagttcacc tctgccagcg acgtgtggag ctttggcatt gtcatgtggg    2580
aggtgatgac ctatggcgag cggccctact gggagttgtc caaccacgag gtgatgaaag    2640
ccatcaatga tggcttccgg ctccccacac ccatggactg cccctccgcc atctaccagc    2700
tcatgatgca gtgctggcag caggagcgtg cccgccgccc caagttcgct gacatcgtca    2760
gcatcctgga caagctcatt cgtgccctg actccctcaa gaccctggct gactttgacc     2820
cccgcgtgtc tatccggctc cccagcacga gcggctcgga gggggtgccc ttccgcacgg    2880
tgtccgagtg gctggagtcc atcaagatgc agcagtatac ggagcacttc atggcggccg    2940
gctacactgc catcgagaag gtggtgcaga tgaccaacga cgacatcaag aggattgggg    3000
tgcggctgcc cggccaccag aagcgcatcg cctacagcct gctgggactc aaggaccagg    3060
tgaacactgt ggggatcccc atctgagcct cgacagggcc tggagcccca tcggccaaga    3120
atacttgaag aaacagagtg gcctccctgc tgtgccatgc tgggccactg gggactttat    3180
ttatttctag ttctttcctc cccctgcaac ttccgctgag gggtctcgga tgacaccctg    3240
gcctgaactg aggagatgac cagggatgct gggctgggcc ctctttccct gcgagacgca    3300
cacagctgag cacttagcag gcaccgccac gtcccagcat ccctggagca ggagccccgc    3360
cacagccttc ggacagacat atgggatatt cccaagccga ccttccctcc gccttctccc    3420
acatgaggcc atctcaggag atggagggct tgcccagcg ccaagtaaac agggtacctc     3480
aagccccatt tcctcacact aagagggcag actgtgaact tgactgggtg agacccaaag    3540
cggtccctgt ccctctagtg ccttctttag accctcgggc cccatcctca tccctgactg    3600
gccaaaccct tgctttcctg ggcctttgca agatgcttgg ttgtgttgag gtttttaaat    3660
atatattttg tactttgtgg agagaatgtg tgtgtgtggc aggggccccc gccagggctg    3720
gggacagagg gtgtcaaaca ttcgtgagct ggggactcag ggaccggtgc tgcaggagtg    3780
tcctgcccat gccccagtcg gccccatctc tcatcctttt ggataagttt ctattctgtc    3840
agtgttaaag attttgtttt gttggacatt tttttcgaat cttaatttat tatttttttt    3900
atatttattg ttagaaaatg acttatttct gctctggaat aaagttgcag atgattcaaa    3960
ccgaaaaaaa                                                           3970
```

COMPOSITIONS COMPRISING INHIBITORS OF EPH RECEPTOR EXPRESSION IN TUMOR STEM CELLS AND METHODS OF TREATMENT THEREOF

CROSS REFERENCE TO RELATED APPLICATIONS

The present application claims priority to European Patent No: 10185930.4, filed on Oct. 1, 2010, which is incorporated herein by reference in its entirety.

FIELD

The present disclosure concerns the field of malignant tumors of the central nervous system and provides pharmaceutical compositions suitable for the therapeutic and for the prophylactic treatment of brain tumors and for inhibiting the growth of the tumor mass.

BACKGROUND

Gliomas are the most common brain tumors, and, in particular, grade IV glioma, also named glioblastoma multiforme (GBM), represents the most severe type. This highly aggressive tumor develops either de novo (primary GBM) or as consequence of the malignant progression from low-grade glioma (secondary GBM). In both cases, due to the intrinsic characteristic of this tumor, prognosis is poor and the median survival when radiotherapy and chemotherapy are combined is 14.6 months (12.).

Glioblastoma multiforme is a highly heterogeneous tumor, which shows clear cellular and tissue dissimilarities, displaying a strong hemorrhagic component and wide areas of necrosis, which, at the microscopic level, coincide with the presence of massive microvascular proliferation and pseudopalisading patterns (9.).

Most importantly, GBM is characterized by a diffuse tissue-distribution pattern, with extensive dissemination of the tumor cells within the brain that hinders complete surgical resection. Therefore, disease recurrence occurs in the majority of the patients. Moreover, GBM progression is also accompanied by extensive angiogenesis.

The need and importance is increasingly felt for the development of new markers, and for the identification of specific molecular targets for the development of a therapy for blocking the growth and diffusion of GBM and for its treatment.

In the last decade, several seminal studies have dealt with the identification and isolation of cancer stem cells (CSCs), which might be responsible for the initiation, maintenance and progression of different types of tumors. It has been suggested that the persistent growth of cancers, clonal diversification and evolution, tumor metastasis and recurrence after therapy may be the consequence of the maintenance by tumor cells of the proliferative potential of stem cells from which the tumor may have originated, which are called cancer stem cells. Transformed stem-like cells have been found in hematopoietic malignancies, breast cancer and stem-like neural progenitors also in human brain tissues.

The discovery that malignant brain tumors, or at least some of them, comprise cancer stem cells provides new opportunities at both the experimental and clinical level. In fact, even if the cancer stem cell hypotesis suggests that these cells constitute a minor cell pool within the overall tumor mass, this small pool, would be the true culprit responsible for establishing and expanding the tumor and perpetuating it following surgery.

Long-term proliferating cancer stem cells (CSCs) have been studied in GBM (GBM-CSCs), which possess both the full complement of neural stem cell functional characteristics (13.) and the ability to produce tumors which closely resemble the main histological, cytological and architectural features of the human GBM pathology (5.).

Due to their ability to generate true phenocopies of the human disease over time, these GBM-CSCs represent one of the most suitable models for studying GBM physiology in vitro and in vivo and might enable the discovery of genes/pathways directly involved in the regulation of the invasive and angiogenic behavior of the GBM itself. Molecular markers that either are found specifically on tumor cells or are highly over-expressed on malignant cells and nearly absent or downregulated on normal cells are attractive therapeutic targets for approaches such as targeted drug delivery. The Eph receptors comprise the largest family of tyrosine kinases encoded in the human genome and play important roles in development and disease receiving an external stimulus and responding by transmitting a signal to the inside of the cell, starting numerous processes that are vital for the maintenance of organism function. They can be distinguished from other RTKs in that they all recognize ligands, knows as ephrins, which are anchored to the membrane of apposing cells. Ligand binding typically triggers tyrosine phosphorylation of Eph receptors. (4.).

It is therefore object of the present disclosure the development of novel and more specific therapeutic strategies for brain cancers, in particular to identify an inhibitor of the growth and proliferation of glioblastoma.

SUMMARY

The present disclosure concerns a pharmaceutical composition which comprises at least one inhibitor of expression and/or an inhibitor of activity of an Ephrin receptor and a pharmaceutically acceptable bioactive means.

As will be further described in the detailed description of the disclosure, the pharmaceutical composition of the present disclosure has the advantages of being specific for the molecular target of the Ephrin receptor, which is highly expressed in the development of the nervous system, is critical for signal transmission and regulation of many processes within the brain cells.

A further aspect of the present disclosure is an inhibitor of expression and/or an inhibitor of activity of an Ephrin receptor for use in the treatment of a brain tumor and related methods and systems for treatment and/or prevention of a brain tumor.

BRIEF DESCRIPTION OF THE DRAWING

The characteristics and advantages of the present disclosure will be apparent from the detailed description reported below, from the Examples given for illustrative and non-limiting purposes, and from the annexed FIGS. 1-12, wherein:

FIGS. 1A-1H: shows the expression of Eph receptors and ephrin ligands in human GBM-CSC cells, as described in Example 2.

FIG. 1A Relative mRNA expression levels of Ephrin receptors (Ephs) and ephrin ligands (ephrins or EFNs) in GBM CSC cells analyzed by RT-PCR.

FIG. 1B cytofluorimetric analysis of the expression of Eph receptors in GBM-CSCs.

FIG. 1C FACS analysis confirming EphA2 receptor enhanced expression in various GBM-CSC lines.

FIGS. 1D-1H Confocal images of immunofluorescence labeling confirming the expression of both EphA2 receptor and ephrinA1 ligand in a representative GBM-CSC line at various magnifications.

FIG. 2A Immunolocalization of EphA2 protein levels in frozen primary GBM in the core of the tumor.

FIG. 2B Immunolocalization of EphA2 protein levels in frozen primary GBM at the periphery of the tumor.

FIGS. 2C-2D Cytofluorimetric analysis of EphA2 receptor protein in GBM-CSCs.

FIGS. 3A-3H: the influence of ephrinA1-Fc or EphA2-Fc treatment on EphA2 receptor phosphorylation and down-regulation in GBM-CSCs as described in Example 4.

FIG. 3A Dose-response curve and FACS analysis of ephrinA1-Fc or EphA2-Fc treatment on EphA2 receptor expression and phosphorylation in GBM-CSCs at the noted concentrations.

FIG. 3B GidTime-course curve and FACS analysis of ephrinA1-Fc or EphA2-Fc treatment on EphA2 receptor expression and phosphorylation in GBM-CSCs at the indicated periods of time.

FIG. 3C: Immuno-fluorescence for human EphA2 performed on GBM-CSCs confirms that most of the cells were positive for the receptor.

FIGS. 3D-3E: Immuno-fluorescence for human Eph2 performed on GBM-CSCs after, respectively, ephrinA1-Fc 1.0 μg/mL and 5.0 μg/mL confirms that only few cells were labeled for the same antigen.

FIG. 3F: Western blotting on total cell lysates of EphA2 receptor in ephrinA1-Fc treated GBM-CSCs. Cells were grown in the absence (−) or in the presence (+) of ephrinA1-Fc at the indicate periods of time.

FIG. 3G: Total cell lysates immunoblotting with phosphotyrosine-specific (4G10) antibody of immunoprecipitated EphA2 levels.

FIG. 3H Western blot analysis showing EphA2 receptor expression in GBM-CSCs after EphA2-Fc treatment.

FIGS. 4A-4M: ephrinA1-Fc and EphA2-Fc treatment reduces GBM-cancer stem cells proliferation in vitro as described in Example 5.

FIGS. 4A-C Growth kinetics curves after ephrinA1-Fc addition at the indicated concentrations to the GBM-CSC cells in culture.

FIG. 4D Growth kinetics curves after ephrinA1-Fc addition to human neural stem cells.

FIG. 4E Growth kinetics curves after ephrinA1-Fc addition to U87 human glioma cells.

FIG. 4F Growth kinetics curves after ephrinA1-Fc or EphA2-Fc addition to the GBM-CSC cells in culture.

FIGS. 4G-4H Cells proliferation index estimated by BrdU cell proliferation assay.

FIG. 4I Cells proliferation index estimated by quantification of KI67-positive immunoreactive cells.

FIGS. 4J-4K Phase-bright microscopy images of neurospheres from two acutely dissociated GBM-CSC lines in the absence of EphA2-Fc.

FIGS. 4L-4M Phase-bright microscopy images of neurospheres from two acutely dissociated GBM-CSC lines grown in the presence of EphA2-Fc.

FIGS. 5A-5J: soluble ligand and receptor deplete the GBM brain tumor initiating cell population in vitro as described in Example 6.

FIG. 5A Serial clonogenic assays in GBM-CSC cells.

FIGS. 5B-5C Phase-bright microphotographs of neurospheres from two GBM-CSC line cultures showing the effects of ephrinA1-Fc on clone size of resting controls.

FIGS. 5D-5E Phase-bright microphotographs of neurospheres derived from two GBM-CSC line grown with ephrinA1-Fc 0.5 μg/mL showing the effects of ephrinA1-Fc on clone size.

FIGS. 5F-5G Phase-bright microphotographs of neurospheres from two GBM-CSC line cultures showing the effects of ephrinA1-Fc 1.0 μg/mL on clone size.

FIGS. 5H-5I Sorter-based purification of two different cell populations, differing for EphA2 expression level, indicated that EphA2 protein expression directly correlates with the clonal efficiency of GBM-CSCs. Schematic of the experimental design.

FIG. 5J Clonogenic percentage of EphA2++ and EphA2−− GBM-CSCs.

Hoechst 33342 dye staining profiles (2 μg/mL) of human resting GBM-CSCs and treated with 5.0 ug/mL of EphA2-Fc or ephrinA1-Fc for 48 hours.

FIGS. 7A-7D: ephrinA1-Fc elicits a pro-differentiation effect on GBM-CSCs as described in Example 8.

Cytofluorimetric quantification of the frequency of neurons (ME-PE βtubIII), astrocytes (ME-FITC GFAP) and oligodendrocytes (ME-PE GalC) in Fc treated control versus ephrinA1-Fc-treated GBM-CSCs.

Figure 8:
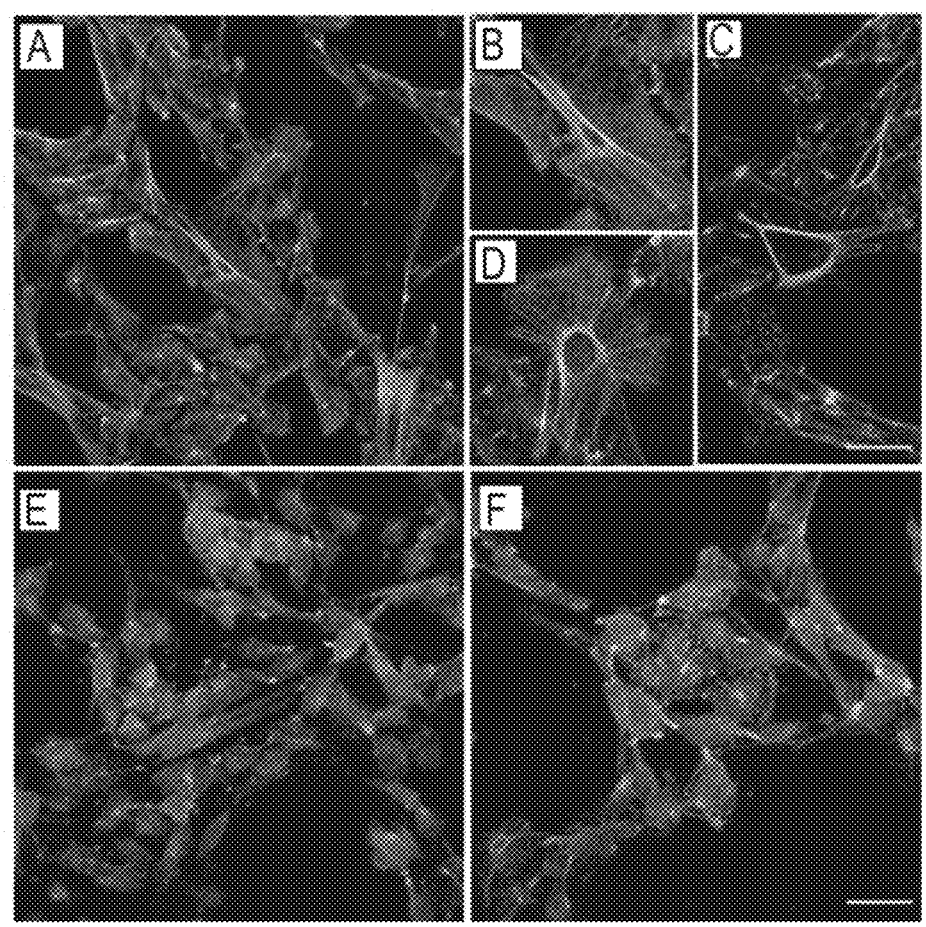

FIGS. 8A-8R: EphA2 activation by either soluble ephrinA1-Fc or EphA2-Fc induces cytoskeletal re-organization and inhibits GBM-CSC cell spreading and migration in vitro as described in Example 10.

FIGS. 8A-8D Confocal localization of F-actin protein (phalloidin staining) in untreated GBM-CSC cells, which have a highly migratory phenotype.

FIGS. 8E-8F Confocal localization of F-actin protein (phalloidin staining) changes 5 min after respectively ephrinA1-Fc or EphA2-Fc treatment. Cells remained rounded and failed to spread.

FIG. 8G: Western blot analysis showing that ephrinA1-Fc stimulation induces FAK rapid inactivation and dephosphorylation. Cells were grown in the absence (−) or in the presence (+) of ephrinA1-Fc for the indicated periods of time, and then lysated.

FIG. 8H: cultrex invasion assays showing human microvascular dermal endothelial cells (HMVECs) migrated to the lower surface of the membrane fixed and stained. HMVECs plated in the top of the chamber in basal medium as control FIGS. 8I-8J HMVECs plated in the top of the chamber in basal medium and In the low compartment VEGF (20 ng/mL) or GBM-CSCs conditioned medium.

FIGS. 8L-8M HMVECs plated in the top of the chamber in the presence of EphA2-Fc (5.0 ug/mL) and in the low compartment VEGF (20 ng/mL) or GBM-CSCs conditioned medium.

FIG. 8K Control human IgG as control in the upperside did not affect cell migration in response to VEGF in the low compartment.

FIG. 8N Confocalimmuno-fluorescence showing the positivity of GBM-CSCs Fc-treated control for phosphorylated ERK1/2.

FIG. 8P Confocalimmuno-localization of phosphorylated ERK1/2 in GBM-CSCs after a chemical inhibitor of MEK1 activation (U0126) treatment.

FIG. 8O and FIG. 8Q Confocalimmuno-fluorescence showing the frequency of phosphorylated ERK1/2 positivity in GBM-CSCs 6 hours after, respectively, EphA2-Fc or ephrinA1-Fc addition.

FIG. 8R: Western blot analysis of equalized cell lysates with the phosphorylated ERK1/2 confirmed that increasing concentrations of ephrinA1-Fc enhance ERK1/2 in GBM-CSCs FIGS. 9A-9B: Treatment of GBM-CSCs with rhBMP4 enhances ephrinA1-Fc inhibitory effects as described in Example 11.

Figure 9A:
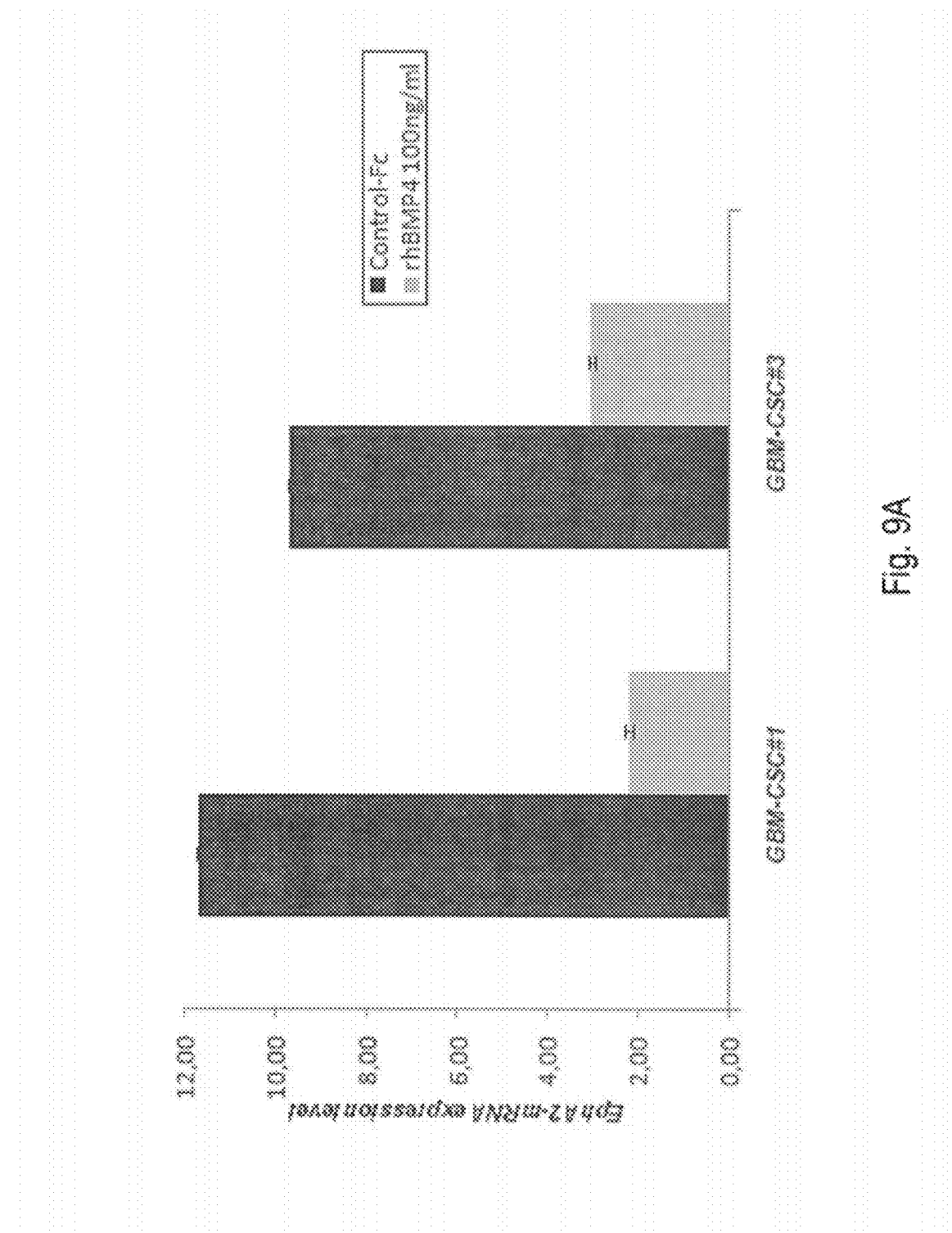

FIG. 9A RT-PCR analysis using specific primers for the measurement of average levels of EphA2 in GBM-CSC cell lines with control-Fc or rhBMP4 at the indicated concentration for 48 hours before isolation of mRNA.

Figure 9B:
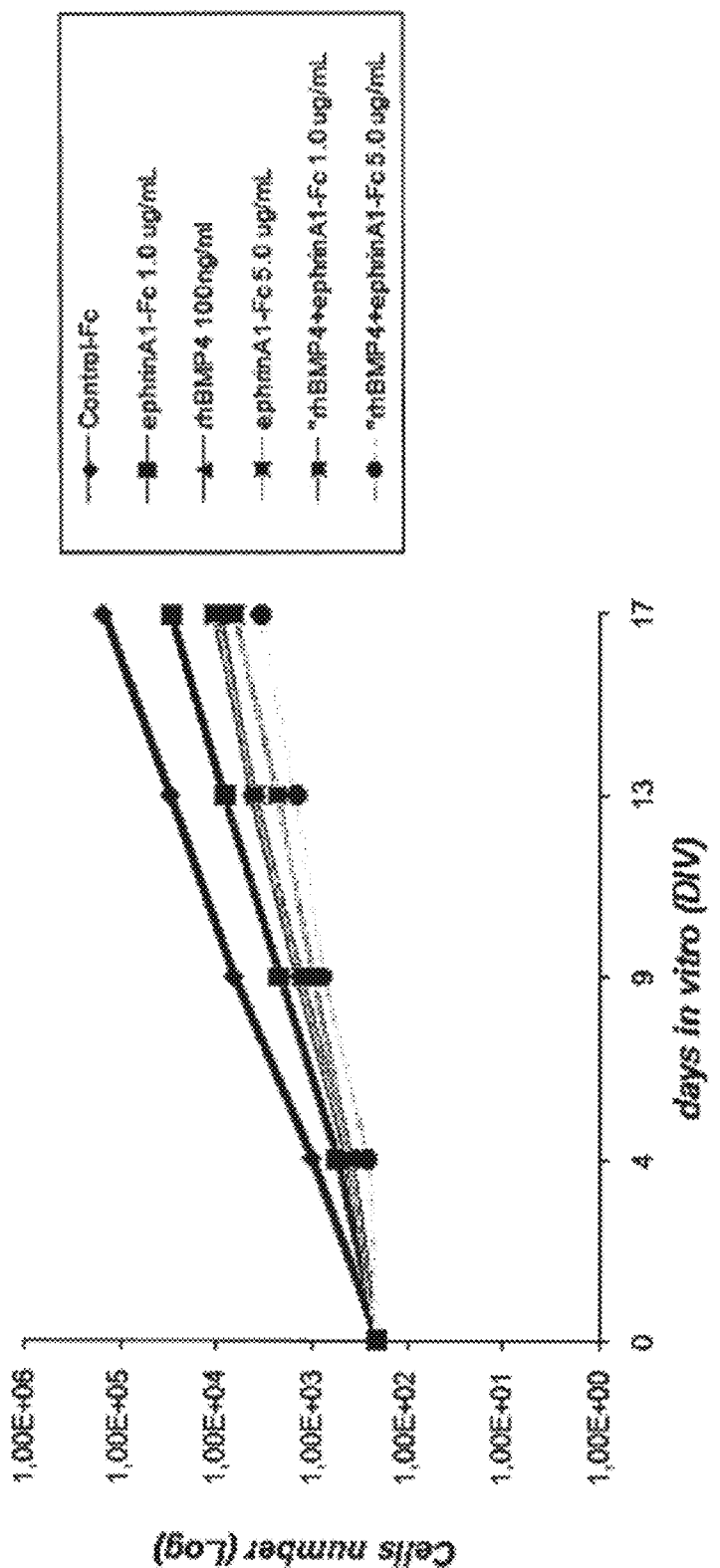

FIG. 9B Growth kinetics curves of GBM-CSCs grown with ephrinA1-Fc in the absence or in the presence of rhBMP4. Growth curves are representative of one GBM-CSC line.

Figure 10A:
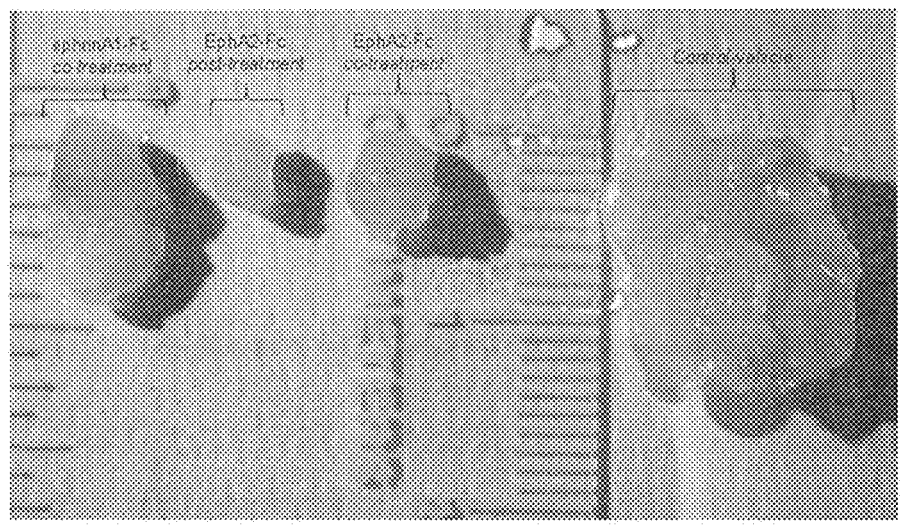
Figure 10B:
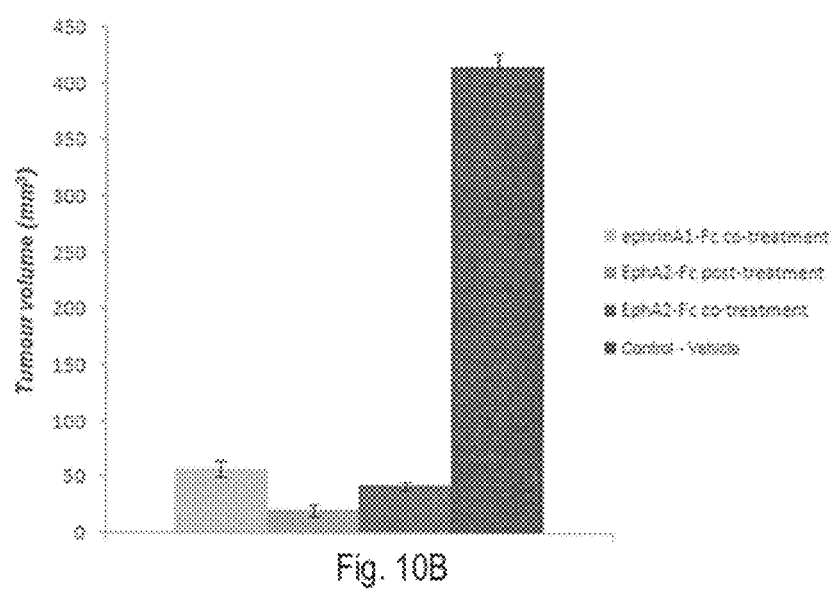

FIGS. 10A-10B: EphrinA1-Fc and EphA2-Fc treatment inhibit tumor growth in vivo in a xenograft model as described in Example 12.

FIG. 10A Comparison of tumor morphology associated with different treatments 35 days after cells injection.

FIG. 10B Relative tumor sizes measurement. The graph shows mean±s.e.m. in the four groups of six mice.

FIGS. 11A-11F: EphA2 recruitment by soluble ligand or receptor inhibits tumorigenicity of GBM-CSCs in an orthotopic model of human GBM as described in Example 13.

FIGS. 11A-11B Bioluminescence monitoring of luc-GBM-CSCs tumor xenografts showing a corresponding signal increase from the tumors.

Figure 11C:
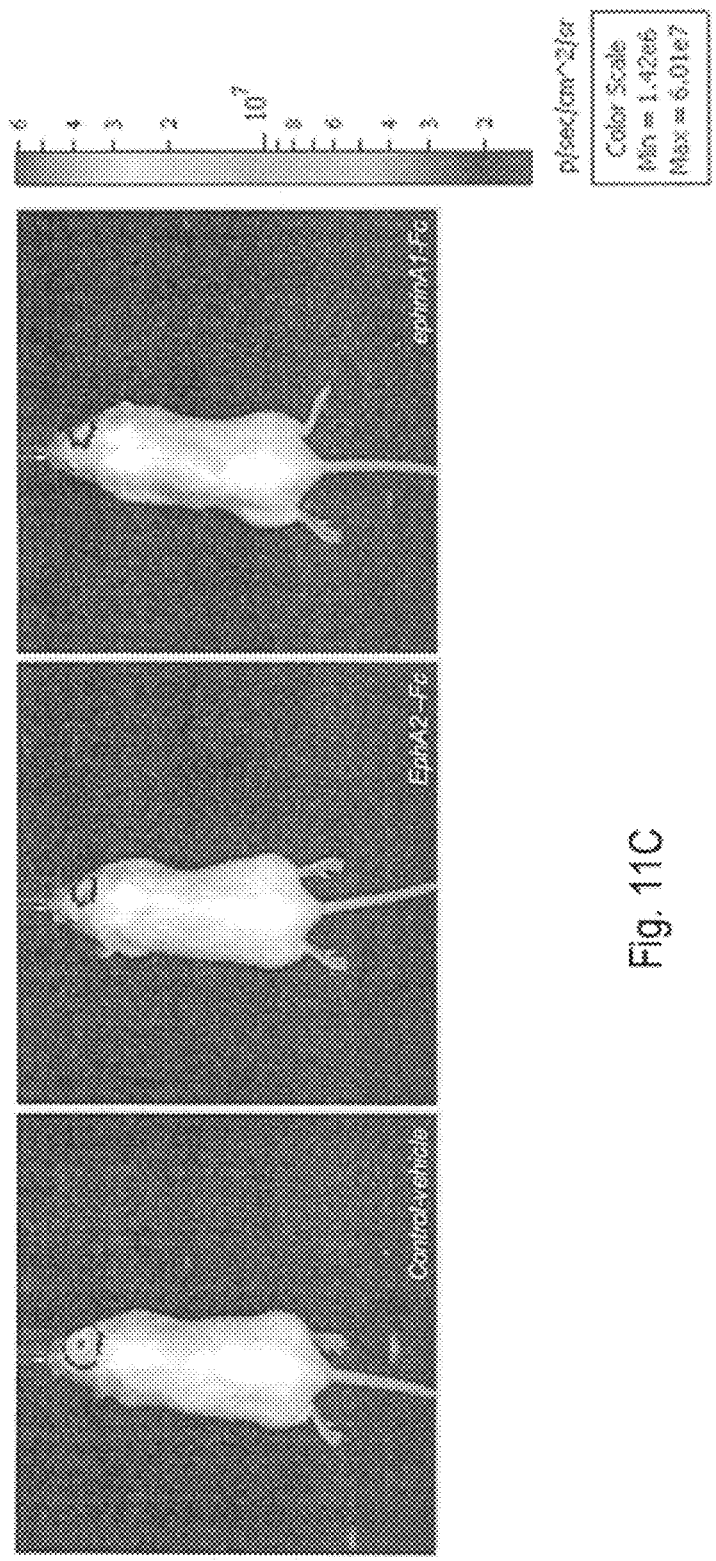

FIG. 11C Differences in tumor growth and tumor size detected in vivo following intracranial injection of resting GBM-CSCS and pre-treated with EphA2-Fc or ephrinA1-Fc.

Figures 11D, 11E, 11F:
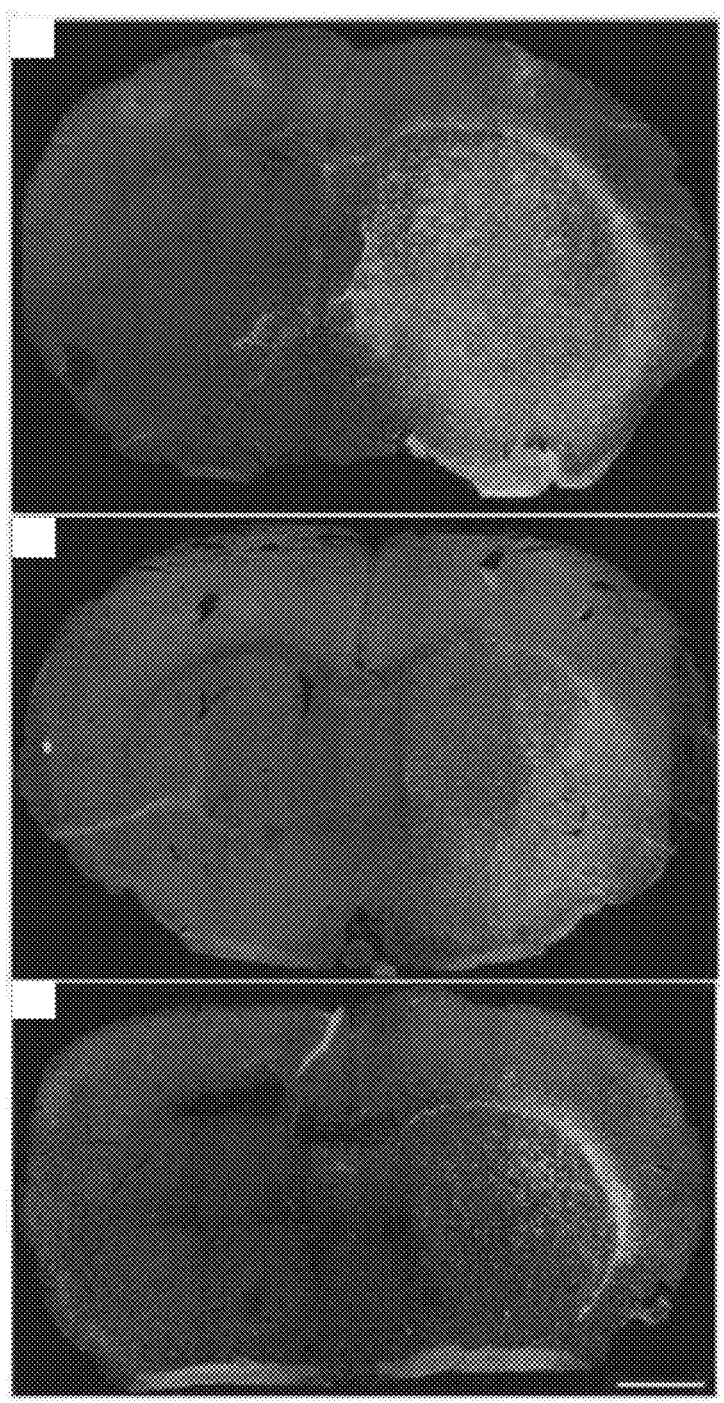

FIG. 11D Confocal images showing tumors derived from untreated luc-GBM-CSCs six weeks following orthotopic implantation.

FIGS. 11E-11F Confocal images showing tumors derived from, respectively, ephrinA1-Fc or EphA2-Fc treated luc-GBM-CSCs, six weeks following orthotopic implantation.

Figure 12:
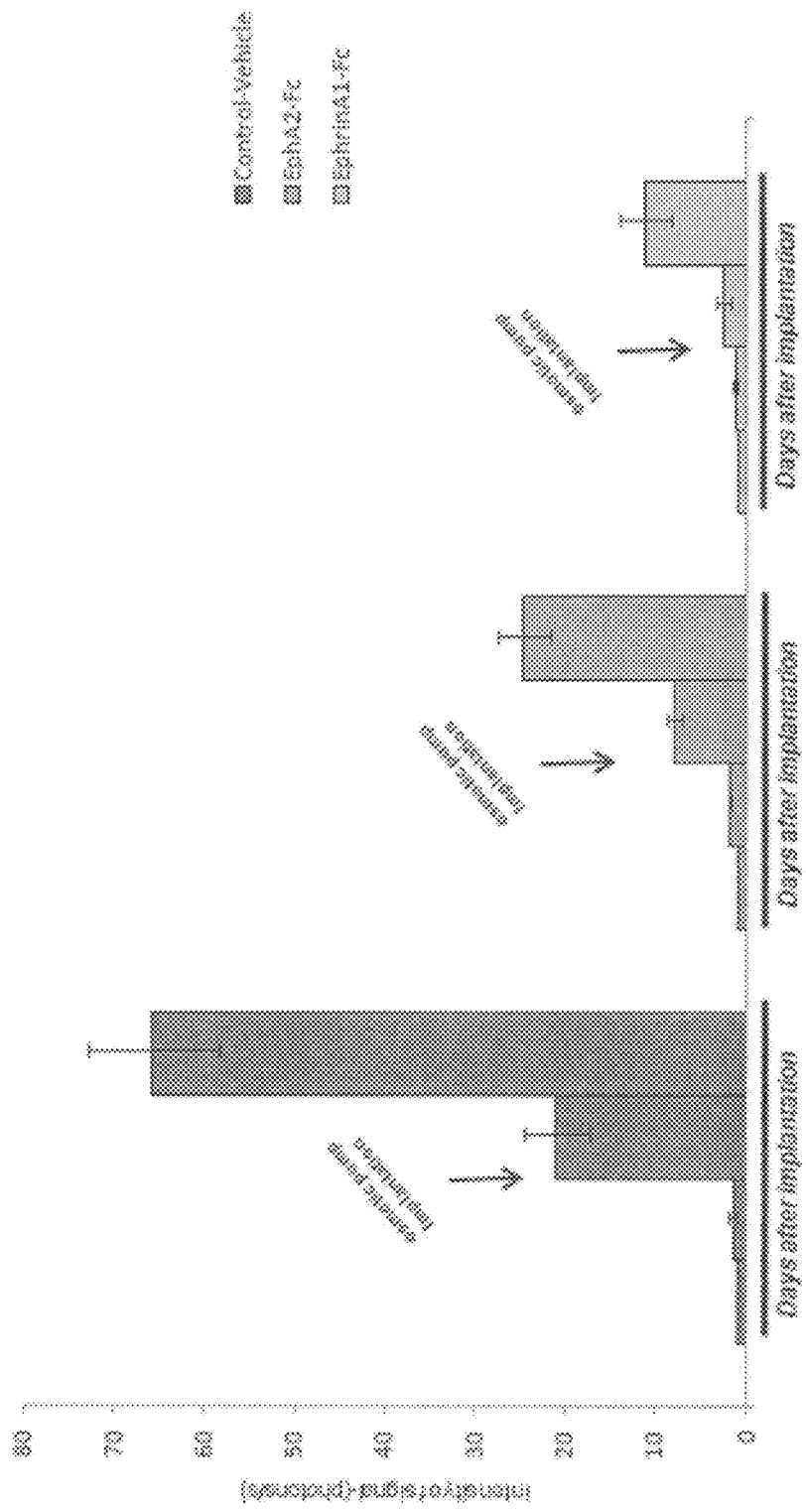

FIG. 12: EphA2-Fc and ephrinA1-Fc administration inhibits established primary tumor growth in an orthotopic model of human GBM as described in Example 14.

Bioluminescence monitoring of luc-GBM-CSCs tumor xenografts post-treated for 14 days with ephrinA1-Fc or EphA2-Fc.

DETAILED DESCRIPTION

The present disclosure concerns a pharmaceutical composition which comprises at least one inhibitor of expression and/or an inhibitor of activity of an Ephrin receptor and a pharmaceutically acceptable bioactive means.

In the present disclosure, by inhibitor of activity of an Ephrin receptor, a type of receptor ligand that does not provoke a biological response, but blocks or diminishes agonist-mediated responses is intended.

In the present disclosure, by inhibitor of expression of an Ephrin receptor, a downregulator of the expression and/or of activity of the receptor is intended.

The pharmaceutical compositions of the present disclosure has the advantages of being specific for the molecular target of the Ephrin receptor, which is highly expressed in the development of the nervous system, is critical for signal transmission and regulation of many processes within brain cells.

A specific pharmaceutical composition which acts on the molecular target of glioblastoma multiforme (GBM) would avoid the need of surgical resection and therefore the extensive dissemination of tumor cells within the brain after such operations, which often results in tumor recurrence.

A further advantage of the pharmaceutical composition according to the present disclosure is that of being less toxic and more efficacious and specific than the commonly used radiotherapy and chemotherapy alone or combined, by targeting the true tumor-initiating cells, rather than the overall tumor mass.

This approach portrays a scenario by which one attempts at "reprogramming" the tumor-initiating cell to acquire a non-pathogenic phenotype, rather than trying to kill the cells by cytotoxic means.

In a further aspect, the disclosure provides the pharmaceutical composition which comprises at least one inhibitor of expression and/or an inhibitor of activity of an Ephrin receptor, wherein said inhibitor of expression and/or activity of an Ephrin receptor is an inhibitor of cancer stem cell proliferation.

Since the presence of proliferating cancer stem cells in GBM has been demonstrated, it has been increasing felt for the need of a specific composition that acts on the proliferation and persistent growth of cancers, also due to the cancer stem cells present in the tumors.

The pharmaceutical composition of the present disclosure surprisingly can act on the proliferative potential of stem cells.

In a still further aspect, the disclosure provides the pharmaceutical composition which comprises at least one inhibitor of expression and/or an inhibitor of activity of an Ephrin receptor, wherein said inhibitor of expression and/or activity of an Ephrin receptor is an inhibitor of cancer stem cell migration.

The advantages of the present disclosure can be further demonstrated by the inhibition not only of the establishment, but also of the expansion of the cancer stem cell whose migratory capabilities are blocked.

In a still further aspect, the disclosure provides the pharmaceutical composition which comprises at least one inhibitor of expression and/or an inhibitor of activity of an Ephrin receptor, wherein said cancer stem cell is a malignant brain cancer stem cell.

GBM represents a very severe type of brain tumor, which is highly aggressive and has a malignant progression.

The pharmaceutical composition of the present disclosure has the advantage of acting specifically on the molecular target of glioblastoma multiforme inhibiting the malignant stem cell cancer progression.

In a still further aspect, the disclosure provides the pharmaceutical composition which comprises at least one inhibitor of expression and/or an inhibitor of activity of an Ephrin receptor, wherein said inhibitor of expression and/or activity of an Ephrin receptor is selected from the group consisting of SEQ ID NO. 1 and SEQ ID NO. 3.

For the purposes of the present disclosure, each inhibitor of expression and of activity of Ephrin receptors has a corresponding SEQ ID NO. as follows:

SEQ ID NO. 1 corresponds to the aminoacidic sequence of ephrinA1, amino acid sequence gi[333596]ref[NP_004419.2] ephrin-A1 isoform a precursor [*Homo sapiens*];

SEQ ID NO. 2 corresponds to the nucleotidic sequence of ephrinA1, nucleotide sequence gi[33359681]ref[NM_004428.2] *Homo sapiens* ephrin-A1 (EFNA1), transcript variant 1 mRNA;

SEQ ID NO. 3 corresponds to the aminoacidic sequence of EphA2 amino acid sequence gi[32967311]ref[NP_004422.2] Ephrin type-A receptor 2 precursor [*Homo sapiens*];

SEQ ID NO. 4 corresponds to the nucleotidic sequence of EphA2, nucleotide sequence gi[296010835]ref[NM_004431.3] *Homo sapiens* EPH receptor A2 (EPHA2), mRNA.

A further aspect of the present disclosure is an inhibitor of expression and/or an inhibitor of activity of an Ephrin receptor for use in the treatment of a brain tumor.

The advantages provided by the present disclosure are due to the use of specific inhibitors which act on the molecular target involved with the development and progression of brain tumors.

In a preferred embodiment, the present disclosure provides an inhibitor of expression and/or an inhibitor of activity of an Ephrin receptor for use in the treatment of a brain tumor, wherein said inhibitor expression and/or activity of an Ephrin receptor is selected from the group consisting of SEQ ID NO. 1 and SEQ ID NO. 3.

For the purposes of the present disclosure, each inhibitor of expression and of activity of Ephrin receptors has a corresponding SEQ ID NO. as described above.

The unregulated over-expression of Ephrin receptors is correlated with tumorigenesis, as related to tumor growth and survival, and associated with angiogenesis and metastasis in human cancer progression. The inhibition of the expression and activity of the Ephrin receptor is therefore advantageous for blocking tumor progression.

A still further aspect of the present disclosure is the use of an inhibitor of expression and/or an inhibitor of activity of an Ephrin receptor, wherein said brain tumor is a glioblastoma, and in a still further aspect, wherein said brain tumor is glioblastoma multiforme.

A still further aspect of the present disclosure is the use of an inhibitor of expression and/or an inhibitor of activity of an Ephrin receptor, wherein said treatment is the prophylactic treatment of a brain tumor recurrence after surgery.

A still further aspect of the present disclosure is the use of an inhibitor of expression and/or an inhibitor of activity of an Ephrin receptor, wherein said treatment is the therapeutic treatment of a brain tumor recurrence after surgery.

The Ephrin receptor, expressed in tumor blood vessel, also plays an important role in angiogenesis and tumor neovascularization through association with its endogenous ligand, ephrinA1. Their signalling in tumors promotes the migration of endothelial cells and their assembly into capillary structures by regulating cytoskeletal plasticity, matrix attachment, and/or intercellular adhesion.

The inhibitors of expression and inhibitors of activity of an Ephrin receptor according to the present disclosure surprisingly block angiogenesis and tumor neovascularization, inhibiting the tumor growth and recurrence after surgery.

A still further aspect of the present disclosure is the use of an inhibitor of expression and/or an inhibitor of activity of an Ephrin receptor, wherein said treatment inhibits the growth of the brain tumor mass.

A still further aspect of the present disclosure is the use of an inhibitor of expression and/or an inhibitor of activity of an Ephrin receptor, wherein said inhibitor of expression and/or activity of an Ephrin receptor is an inhibitor of cancer stem cell proliferation.

The advantage of the present disclosure can be further demonstrated by the fact that the Ephrin receptor inhibition blocks the cancer stem cell migration and proliferation.

A further advantage of the pharmaceutical composition according to the present disclosure is that of being able to provide patient-selective therapies, effectively designed to target a specific cancer stem cell population inside a solid tumor and tailored to deplete the cancer stem cell pool and tumorigenicity.

EXAMPLES

Example 1

Isolation of Glioblastoma Multiforme-Derived Cancer Stem Cells (GBM-CSCs) from Tumor Samples Tumor specimens were obtained from the Unit of Neurosurgery, after patients' surgical resections. Adult human glioblastoma (GBM) tissue samples were obtained and classified according to World Health Organization guidelines. Each neoplastic tissue was divided in two pieces. The first one used for histopatological analysis: in details, the tissue was immersed either in 4% paraformaldehyde for 24 hours for paraffin embedding and immunohistochemistry, or placed in a sucrose solution at decreasing concentrations beginning at 40% to obtain floating sections for confocal microscopy.

The second piece was used to obtain GBM cancer stem cell lines. Tissues were cut into 1 mm$^3$ pieces and then mechanically and enzymatically triturated as in Gritti A, 1996 and Galli R, 2004 (6. and 5.) as follows: pieces were transferred into 4 mL of a EBSS solution with 0.8 mg/ml papain (20 U/mL, Worthinghton), 0.2 mg/mL L-cystein (Sigma), 0.2 mg/mL EDTA (Sigma) in a 6 well-plate (Nunc) and incubated for 45 min at 37° C. Tissue sections were then carefully triturated with a fire-polished Pasteur pipette. The cells were collected by centrifugation and single cells were plated in 25 cm$^2$ tissue culture flasks (Nunc) at a density of 8,000/cm$^2$ in the so-called complete medium, a DMEM/F12 (1:1 v/v Gibco) serum-free medium. Complete medium contains 2 mM L-glutamine, 0.6% glucose, 9.6 µg/ml putrescine, 6.3 ng/ml progesterone, 5.2 ng/ml sodium selenite, 0.025 mg/ml insulin, 0.1 mg/ml transferrin (sodium salt, grade II, Sigma), in the presence of 20 ng/mL of both epidermal growth factor (EGF, Peprotech) and fibroblast growth factor (FGF2, Peprotech). Fresh medium was added every 4 days.

The number of primary spheres generated in each flask was assessed 10-20 days after plating. Spheres were then collected in 15 ml tube (BD) by centrifuging for 10 min at 192×g. Primary spheres were then mechanically dissociated to a single-cell suspension and replated for culturing. By days (2-7) typical for each line new spheres were formed that could undergo further passaging.

These cell lines were identified with the name glioblastoma derived cancer stem cells (or tumor initiating cells) (GBM-CSCs).

Part of the GBM-CSCs from successfully established cell lines were frozen down at every sequential third-fourth subculturing step in complete medium plus 10% DMSO (Sigma) and banked. The remainder was expanded further.

Results:

Brain tumors, particularly glioblastomas, embody cells endowed with tumor-initiating capacity and defined with functional features of neural stem cells (GBM-CSCs). Hence, the study of regulatory mechanisms of normal neurogenesis may lead to the identification of novel inhibitors of GBM- CSCs and may result in the development of more specific therapeutic strategies for brain cancers.

Example 2

Determination of Eph Receptors Expression in GBM-CSC Lines by RT-PCR and Cytofluorimetric Analysis Unregulated or overexpressed Eph receptors can drive transformation, tumor growth and survival. The expression and regulation of ephrins and their cognate receptors in human GBM specimens and GBM-CSCs contained therein, both acutely isolated or serially sub-cultured were studied.

RNA Extraction and cDNA Preparation:

Total RNA was extracted from: GBM-CSC lines isolated from different patients with diagnosis of glioblastoma, fresh primary GBM specimens, non-invasive U87 cells (a commercially available human astrocitom 14 e) and from normal human neural stem cells (HNSCs, available in our laboratory, 13.) by using the RNeasy Mini kit (Qiagen).

cDNA was obtained by using Superscript RNase H–Reverse Transcriptase (Gibco) by following the instructions provided by the manufacturer. One μg of total RNA was primed with oligo-dT for cDNA synthesis.

PCR Amplification

The cDNAs were each individually amplified with the PCR primers designed for the identification of the EphA1, EphA2, EphA3, EphA4, EphA5, EphA7, EphA8, EphA10, EphB1, EphB2, EphB3, EphB4, EphB6 receptors and EFNA1, EFNA2, EFNA3, EFNA4, EFNA5, EFNB1, EFNB2, EFNB3 ligands.

All cDNAs used as templates were previously normalized throughout a β-Actin RT-PCR using the following primer pair for 22 rounds of amplification: β-ActinF1 (5'-GGCATCGT-GATGGACTCCG-3') and β-Actin R1 (5'-GCTGGAAG-GTGGACAGCGA-3'). The 610 bp PCR products were then run on a 2% agarose gel and compared for signal intensity against the same PCR product obtained from a cDNA derived from one μg of Human Brain Total RNA (Ambion). Specific primers were designed:

```
EphA1
forward: 5'- GCC TGA CAC CAC ATA CAT CG -3' reverse: 5'- ATA TGC GGG TGG CTA AAC TG -3'

EphA2
forward: 5'- AAA GCC GGC TAC ACA GAG AA -3' reverse: 5'- TTG GAC AAC TCC CAG TAG GG -3'

EphA3
forward: 5'- GAG TTT GCC AAG GAA TTG GA -3' reverse: 5'- TTG GGA TCT TCC CTC CTC TT -3'

EphA4
forward: 5'- ACC AAG CAG TGC GAG AGT TT -3' reverse: 5'- CTC CCC GTA CGA CAT CAC TT -3'

EphA5
forward: 5'- CAA GCC TAA TAT GGC GGT GT -3' reverse: 5'- GTG AAC TGC CCA TCG TTT TT -3'

EphA7
forward: 5'- ATC ATT GGG AGA AGG CAC TG -3' reverse: 5'- ATG GAC AAC ATT TGG GTG GT -3'

EphA8
forward: 5'- GAG AAC GGC TCT CTG GAC AC -3' reverse: 5'- CCT CCA CAG AGC TGA TGA CA -3'

EphA10
forward: 5'- CGA CTA ATG CTC GAC TGC TG -3' reverse: 5'- TGA TCA AGC AAC TGC CAC TC -3'

EphB1
forward: 5'- CAG GGT ACT CGG AGA AGC AG -3' reverse: 5'- CCA GCA TGA GCT GGT GTA GA -3'

EphB2
forward: 5'- AGT TCG GCC AAA TTG TCA AC -3' reverse: 5'- AGG CAG GTG AAT GTC AAA CC -3'

EphB3
forward: 5'- AGC AAC CTG GTC TGC AAA GT -3' reverse: 5'- GGA TGA GCT TGT CCA GGG TA -3'

EphB4
forward: 5'- GAG AGC TGT GTG GCA ATC AA -3' reverse: 5'- TGT AGG TGG GAT CGG AAG AG -3'

EphB6
forward: 5'- TCA TTG CAC ATG GAA AGC AT -3' reverse: 5'- GGG TGA GTC CAG ACA AGG AA -3'

EFNA1
forward: 5'- GGT GAC TGT CAG TGG CAA AA -3' reverse: 5'- AGT GGA AGG AGC AGC ACAT -3'

EFNA2
forward: 5'- ATC TAC TGC CCG CAC TAT GG -3' reverse: 5'- AGG CGT GGC AGA GAT GTA GT -3'

EFNA3
forward: 5'- CAT GCG GTG TAC TGG AAC AG -3' reverse: 5'- GTG GAA CTC GTA GCC CAG AG -3'

EFNA4
forward: 5'- ACA TTG TCT GCC CCC ACT AC -3' reverse: 5'- TGG GCT GAC TCA GAC TTC CT -3'

EFNA5
forward: 5'- AGG ACT CCG TCC CAG AAG AT -3' reverse: 5'- ATC TGG GAT TGC AGA GGA GA -3'

EFNB1
forward: 5'- GCC TGG AGT TCA AGA AGC AC -3' reverse: 5'- GAA CAA TGC CAC CTT GGA GT -3'

EFNB2
forward: 5'- GTG CCA AAC CAG ACC AAG AT -3' reverse: 5'- GAT GTT GTT CCC CGA ATG TC -3'

EFNB3
forward: 5'- AGG CAG AGG GTG GTT ATG TG -3' reverse: 5'- TCT CTT TCC ATG GGC ATT TC -3'
```

Flow Cytometry Analysis with Cell Lines:

To determine Eph receptors expression in various GBM-CSC lines, cell preparations (500,000 cells for each tube) were centrifuged and resuspended in 0.2 mL complete medium. Cells were then exposed for 30 min in the dark at 4°

C. to the primary antibodies. U87 cells as reference control for tumor cells and HNSCs for neural stem cells.

For intracellular stainings, cell preparations (500,000 cells for each tube) were alternatively permeabilized with 0.5 mL of Cytofix/Cytoperm solution (BD Biosciences) at room temperature for 30 min. Cells were washed with 2 mL of BD Perm/Wash 1× (BD) and incubated at room temperature for 10 min. After centrifugation, they were resuspended in 0.2 mL BD Perm/Wash solution 1× (BD) containing the appropriate primary antibody mix.

Primary antibodies employed were:
anti-EphA1 goat polyclonal antibody (0.3 µg, R&D)
anti-EphA2 goat polyclonal antibody (0.5 µg, R&D)
anti-EphA3 goat polyclonal antibody (0.3 µg, Gene Tex)
anti-EphA5 rabbit polyclonal antibody (0.5 µg, Abcam)
anti-EphA7 rabbit polyclonal antibody (0.5 µg, Abcam)
anti-EphA8 goat polyclonal antibody (0.5 µg, Santa Cruz)
anti-EphB1 rabbit polyclonal antibody (0.5 µg, Abcam)
anti-EphB2 rabbit polyclonal antibody (0.5 µg, Abcam)
anti-EphB6 rabbit polyclonal antibody (0.5 µg, Santa Cruz)

After extensive washes 0.3 mL of the appropriate secondary antibody was added:
donkey anti-goat Ig PE-labeled antibody (0.2 µg, Jackson Immunoresearch)
goat anti-rabbit Ig FITC-labeled antibody (0.5 µg, Jackson Immunoresearch)

Each sample incubated for 30 min in the dark at 4° C. After two washes cells were resuspended in 0.5 mL complete medium and analyzed by flow cytometry. Autofluorescence and isotype controls were run routinely for all these assays.

For all the above assays, analyses were performed by flow cytometry Cyan (Coulter) using Summit 4.3 software. Background fluorescence was estimated by substituting the specific primary antibodies with specific isotype controls. Measurement of autofluorescence was also routinely conducted for each condition tested.

Results:

Ephrin receptors and their cognate ligands over-expression can be associated to many type of human cancer progression. As showed in FIG. 1A, most of the Ephrin receptors (13 analyzed) and ligands (8 analyzed) messenger RNA transcript can be retrieved by conventional PCR. All the cDNA were previously normalized throughout a β-actin. A human astrocytoma cell line (U87) was employed as reference for tumor cells, and human neural stem cells (HNSCs) as reference for normal neural stem cells. Interestingly, as opposed to normal and cancer stem cells, ephrinA1 ligand cannot be retrieved at both messenger RNA transcript and protein level in U87 cells.

Remarkably, the expression of Ephrin receptors in GBM-CSCs was confirmed at the protein level by cytofluorimetric analysis, as shown in FIG. 1B. Furthermore, as reported in FIG. 1C, EphA2 is widely upregulated in GBM-derived cancer stem cell lines (n=6). The histograms show means±s.e.m. of three separate assays.

An example of the widespread expression of both EphA2 receptor and ephrinA1 ligand in a representative GBM-CSC line was shown also in FIGS. 1D-1H. Confocal images of immunofluorescence labeling confirm the presence and identify a weak positive staining of EphA2 receptor (FIG. 1D) and its local higher magnification (FIG. 1E, FIG. 1F) and ephrinA1 ligand (FIG. 1G) and its local higher magnification (FIG. 1H) in tumor cells. Scale bar, 40 µm (FIG. 1D, FIG. 1G); 20 µm (FIG. 1E, FIG. 1F); 13 µm (FIG. 1H).

Example 3

Determination of EphA2 Receptor Expression in Primary GBM Tissues

After the demonstration that enhanced levels of EphA2 could be retrieved in GBM-CSC lines, the identification of the presence of immunoreactive EphA2 also in fresh tumor tissues, thus ruling out the possibility that the receptor might develop as a mere consequence of long-term culturing in vitro.

Immunohistochemistry with Primary Tissues:

For immunohistochemical stainings, primary GBM tumor tissues were postfixed in paraformaldheyde for 24 h. Tissues were then cryoprotected in 10%-20% and 30% sucrose solutions in PBS overnight at 4° C., followed by an overnight embedding step in a 2:1 (v/v) 20% sucrose/Tissue-Tek OCT embedding compound mixture. Ten-micrometer-thick serial sections were cut in a cryostat and mounted onto gelatin-coated glass slides for double immunolabelling. Briefly, sections were air-dried and rinsed in 0.1 M Tris-HCl buffer (pH 7.6) containing 0.005% BSA and 0.1% Triton and incubated with the primary antibody overnight at 4° C. (13.).

Tissue sections were stained with goat anti-human EphA2 (1:50, R&D) or monoclonal mouse IgG 1 anti-human EphA2 clone D7 (1:100, Sigma).

Flow Cytometry with Primary Tissues:

Soon after the ezymatical and mechanical digestion described above, cell suspensions isolated from primary tumor specimens were subjected to FACS analysis for EphA2 receptor expression. Briefly, cells derived from GBM tissue dissociation were stained with LDS 751 (10 ng/mL, Molecular Probes) 15 min at room temperature to identify intact nucleated cells. Cells were analyzed by flow cytometer (FACSAria, BD Biosciences), and using a back gating technique (LDS751 positive cells) a region (P1) that identify intact nucleated cells in the dot plot FSC vs SSC was created. To identify intacts nucleated and lives cells, a combined gate was created by adding region (P1), to a region containing 7AAD negative cells. Then, CSCs derived from GBM tissue dissociation were incubated with goat anti-human EphA2 (0.5 µg, R&D) and 7AAD (5 µg/mL, Coulter) in order to identify both positive and died cells.

Figure 2B:
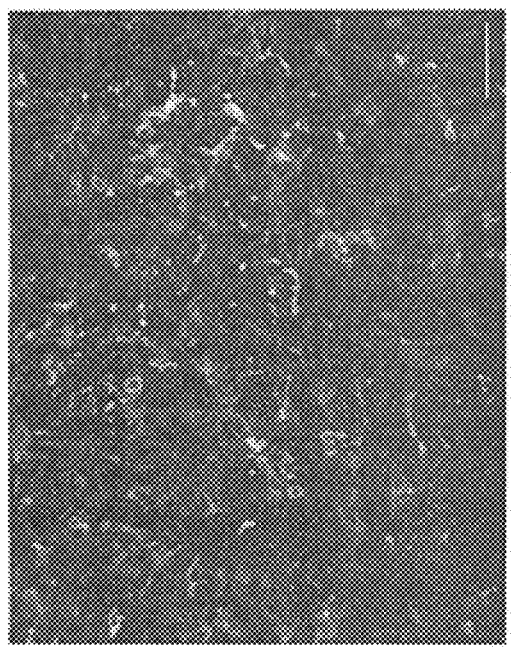
FIGS. 2A-2D: EphA2 enhanced expression levels also in GBM primary patient's tumor tissues as described in Example 3.
Figure 2A:
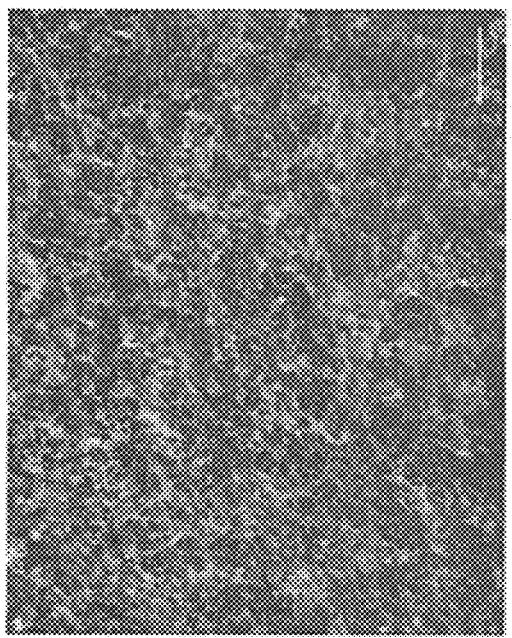
Figure 2D:
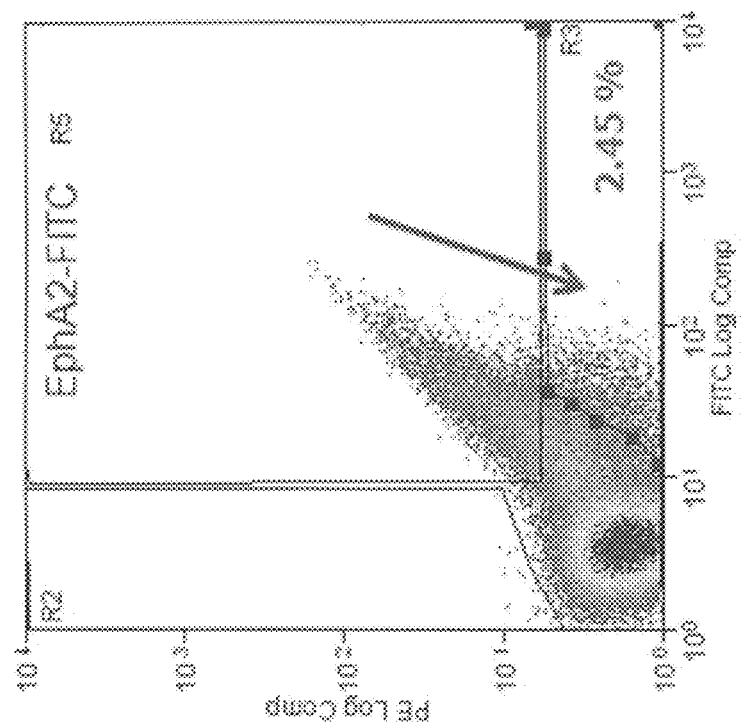
Figure 2C:
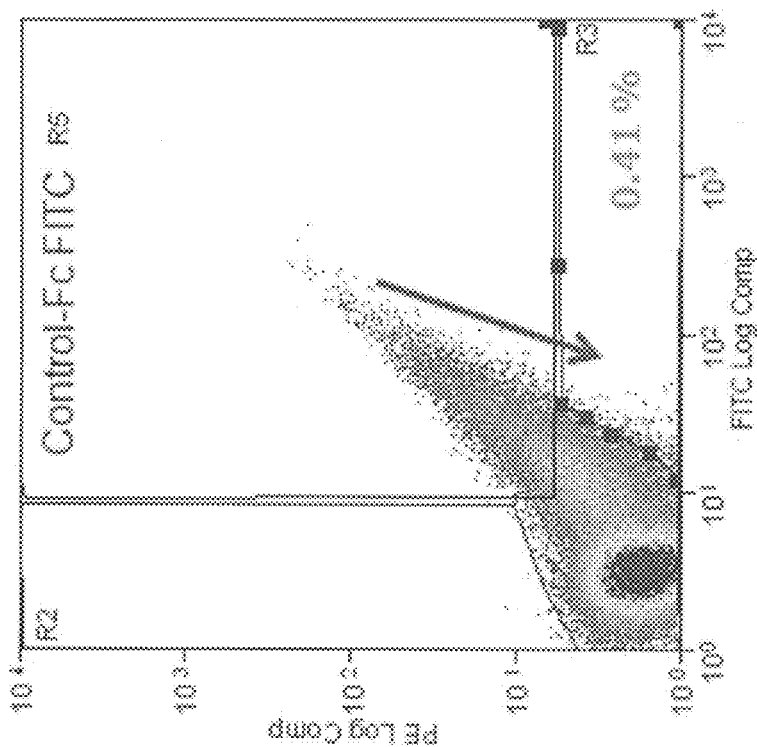

Results:

Immunohistochemistry was employed to examine the localization of EphA2 receptor in primary gliomas and their neighbouring "normal" (peripheric) counterparts from glioma patients. The results shown in the FIGS. 2A-2B clearly reveal a more elevated EphA2 signal in the core of the tumor FIG. 2A relative to its less malignant periphery FIG. 2B (at least 2 cm away from the core). Scale bar, 50 ſm. As shown in FIGS. 2C-2D the lower panel of the same Figure, EphA2 receptor protein was detected also in acutely dissociated GBM-CSCs, constitutively retrievable within the patient's tumor, by cytofluorimetric analysis (n=4) (arrows).

Example 4

Effect of Soluble EphrinA1-Fc (R&D) and Soluble EphA2-Fc Receptor (R&D) on EphA2 Expression and Phosphorylation in Human GBM-CSCs Owed to ligand-induced receptor degradation, down-regulation of EphA2 expression can occur, which results in increased cell adhesion to extracellular matrix (ECM), decreased cell migration and inhibition of malignant growth. Hence, the over-expression of this receptor in GBM-CSC cells might reflect into malignant behaviour and its engagement by ephrinA1-Fc might counteract tumorigenicity.

In this view, the effects of enforced down-regulation of expression or of the activity of EphA2 on tumorigenic properties in GBM-CSCs were determined. EphA2 receptor was engaged to decrease its expression and determine how this contributes to regulate the overall functional properties of these cells, both in vitro and in vivo. The EphA2 was engaged using a soluble ephrinA1-Fc, a mouse ephrinA1-human IgG1 Fc chimera protein. Furthermore, EphA2 seems to be unique among Eph receptors in that its kinase activity may not be entirely dependent on ligand binding. These ligand-independent effects of EphA2 are important in influencing processes that are critical for malignant progression.

The effects of preventing endogenous EphA2 phosphorylation were alternatively analyzed by means of the EphA2-Fc receptor—a chimera protein with an extracellular ligand-binding domain of the receptor fused to the Fc portion of human IgG1—which competitively binds available ligand.

Cytofluorimetric Analysis:

For dose-response analysis, soon after mechanical dissociation cells were seeded in the presence of ephrinA1-Fc (0.001, 0.01, 0.1, 0.5, 1.0 µg/mL) for 24 hours. For time-course analysis, cells were incubated with ephrinA1-Fc (1.0 µg/mL) for 6, 24, 48, 72 hours.

Cell preparations (500,000 cells/sample) were centrifuged and resuspended in 0.2 mL complete medium. Then, they were exposed to anti-EphA2 goat polyclonal antibody (0.5 µg, R&D) for 30 min in the dark at 4° C. After extensive washes, a donkey anti-goat Ig FITC-labeled antibody (0.56 µg/sample, Jackson Immunoresearch) was added and each tube was incubated for 30 min in the dark at 4° C. After two washes cells were resuspended in 0.5 mL complete medium and analyzed by flow cytometry. Autofluorescence and isotype controls were run routinely for all these assays.

Immunocytochemistry:

Cells were seeded at a density of $2.5 \times 10^4$ cells/cm$^2$ onto Cultrex-coated 12-mm diameter glass coverslips (Trevigen) in complete medium as control or in the presence of ephrinA1-Fc (0.5, 1.0 µg/mL) for 24 hours. Cells were washed, fixed with 4% paraformaldheyde in PBS, pH7.4, and immunostaining was carried out. Coverslips were incubated overnight at 4° C. in PBS containing 10% normal goat serum (NGS) or 10% foetal bovine serum (FBS), 0.3% TritonX-100, and the appropriate primary antibodies or antisera (rabbit anti-human ephrinA1, 1:50 Abcam, goat anti-human EphA2, 1:50 R&D). Alternatively, cells were immunostained with mouse monoclonal IgG1 EphA2 clone D7 (1:100, Sigma).

After thorough washing with PBS cells were reacted for 45 min in the dark at room temperature (RT) with the appropriate secondary antibody:
  Cianine Cy2 or Alexa-Fluor 488-conjugated goat anti rabbit (1:200, Jackson Immunoresearch, 1:2000, Invitrogen)
  Cianine Cy3 or Alexa-Fluor 546-conjugated donkey anti goat (1:500, Jackson Immunoresearch, 1:2000 Invitrogen)
  Cianine Cy3-conjugated goat anti mouse (1:800, Jackson Immunoresearch)

Following washing, cell nuclei were counterstained 10 min at room temperature with 4,6-diamidine-2-phenylindole dihydro-chloride (DAR, 50 g/ml in PBS, Sigma), rinsed three times in PBS and once in distilled water and mounted on glass slides with Fluorsave (Calbiochem).

Proper controls for primary and secondary antibodies revealed either non specific staining nor antibody cross-reactivity.

Imaging was analyzed by Zeiss Axioplan2 Microscope and Leica DMIRE2 Confocal Microscope.

Western Blot:

Soon after dissociation cells were plated in complete medium in the presence of ephrinA1-Fc 5.0 µg/mL or EphA2-Fc 5.0 µg/mL for 10, 30, 60 min and 24 hours. Cells were also plated onto Cultrex-coated (Trevigen) flasks and their differentiation induced by removing EGF/FGF2 and adding leukemia inhibitory factor (LIF 10 ng/mL) for 7-10 days. Cells were then resuspended, centrifuged and lysated. Lysis buffer was composed of 50 mM Tris-HCl pH 7.4, 1 mM EDTA and 1% TritonX-100 supplemented with 1% protease inhibitor cocktail (Sigma) and 10% phosphatase inhibitor cocktail (Roche). Cells were collected, washed in PBS and centrifuged at 14,460×g. Protein quantification was performed by the DC Protein Assay (Bio-Rad), using a series of albumin standards. Gel loading buffer was added to 70 µg of each lysate, and the proteins were resolved with 10% polyacrilamide gels and transferred onto the Hybond ECL nitrocellulose membrane (GE), according to standard protocols. Membranes were blocked with Tris-buffered saline (TBS)-T (TBS plus 0.02% Tween20) and 5% milk, and incubated with the following primary antibodies overnight at 4° C.:
  IgG goat anti-human EphA2 (1:750, R&D)
  IgG1 mouse anti-human EphA2 clone D7 (1:500, Sigma)

This step was followed by incubation with horseradish peroxidase-conjugated (HRP) secondary antibodies (1:10.000; Bio-Rad) for 30 min:
  donkey anti-goat IgG (1:5000, Promega)
  rabbit anti-mouse IgG (1:10.000, GE)

Peroxidase activity was detected using the enhanced chemi-luminescence system (GE) following the manufacturers' instruction. As loading control, mouse anti-glyceraldeyhde-3-phosphate dehydrogenase (GAPDH) antibody (1:500, Zymed) was used.

Immunoprecipitation:

Cells were grown in the absence or in the presence of ephrinA1 (1.0, 5.0 µg/mL) or of mouse monoclonal IgG1 isotype control (R&D) for 24 hours and then lysed as described above. To determine the levels of EphA2 phosphorylation, cell lysates containing 100 µg of total protein were incubated with mouse anti-human Eck/EphA2, (1:500, Upstate) overnight at +4° C. with gentle rotation. Following the manufacturers' instruction, Beads (Dynal Invitrogen bead separation) were washed extensively with lysis buffer, and immuno complexes were eluted with 2×LDS sample buffer (Invitrogen), boiled and centrifuged briefly. Proteins were resolved and detected by Western blotting using mouse 4G10 platinum anti-human phosphotyrosine (1:1000, Upstate).

Results:

Decreased ligand-induced receptor internalization and degradation might increase stability of the protein and contribute to the over-expression of EphA2. A dual potential tumor-suppressing role for ephrinA1-Fc that involves repression of oncogenic signaling as a result of both receptor phosphorylation as well as subsequent receptor down-regulation is shown.

Cytofluorimetric analysis in FIGS. 3A, 3B clearly shows that ephrinA1-Fc repress oncogenic signaling through EphA2 receptor down-regulation in human GBM-CSCs. The inhibitory effect of ephrinA1-Fc is either dose or time dependent. Values represent means±s.e.m. from duplicate measurement.

Furthermore, as reported in FIGS. 3C-3E, immuno-fluorescence for human EphA2 performed on GBM-CSCs confirms that most of the cells were positive for the receptor (FIG. 3C), whereas after ephrinA1-Fc 1.0 µg/mL (FIG. 3D) and 5.0

μg/mL (FIG. 3E) only few cells were labeled for the same antigen. Scalebar, 20 μm. In FIG. 3F, the decreased expression of EphA2 receptor in ephrinA1-Fc treated GBM-CSCs was confirmed at protein level by Western blotting on total cell lysates. Notably, the blot confirms that ephrinA1-Fc mediated recruitment of EphA2 receptor remarkably decreased EphA2 expression in GBM-CSCs in a concentration/time dependent manner. Cells were grown in the absence (−) or in the presence (+) of ephrinA1-Fc at the indicate periods of time. The level of immunoreactive protein quantified was completely abolished in 60 minutes. This suggests that EphA2 engagement by its cognate ligand corresponds with a rapid internalization of receptor. A human fibroblast cells line (HF) as negative control for the EphA2 antibody. GAPDH is included as control for equal loading of lysates. The data presented are a single representative of three different GBM-CSC lines.

ephrinA1-Fc triggers EphA2 receptor phosphorylation and degradation in GBM-CSCs. As assessed by immunoprecipitation, on treatment with ephrinA1-Fc (FIG. 3G) the levels of tyrosine-phosphorylated EphA2 increased dramatically over concentration in GBM-CSC cells, an indication of ephrinA1-mediated receptor activation. Soon after dissociation cells were treated with increasing concentrations of ephrinA1-Fc or Fc isotype control for 48 hours. Total cell lysates immunoblotting with phosphotyrosine-specific (4G10) antibody of immunoprecipitated EphA2 levels confirm an increase in EphA2 activation and phosphorylation by ephrinA1-Fc.

Figure 3H:
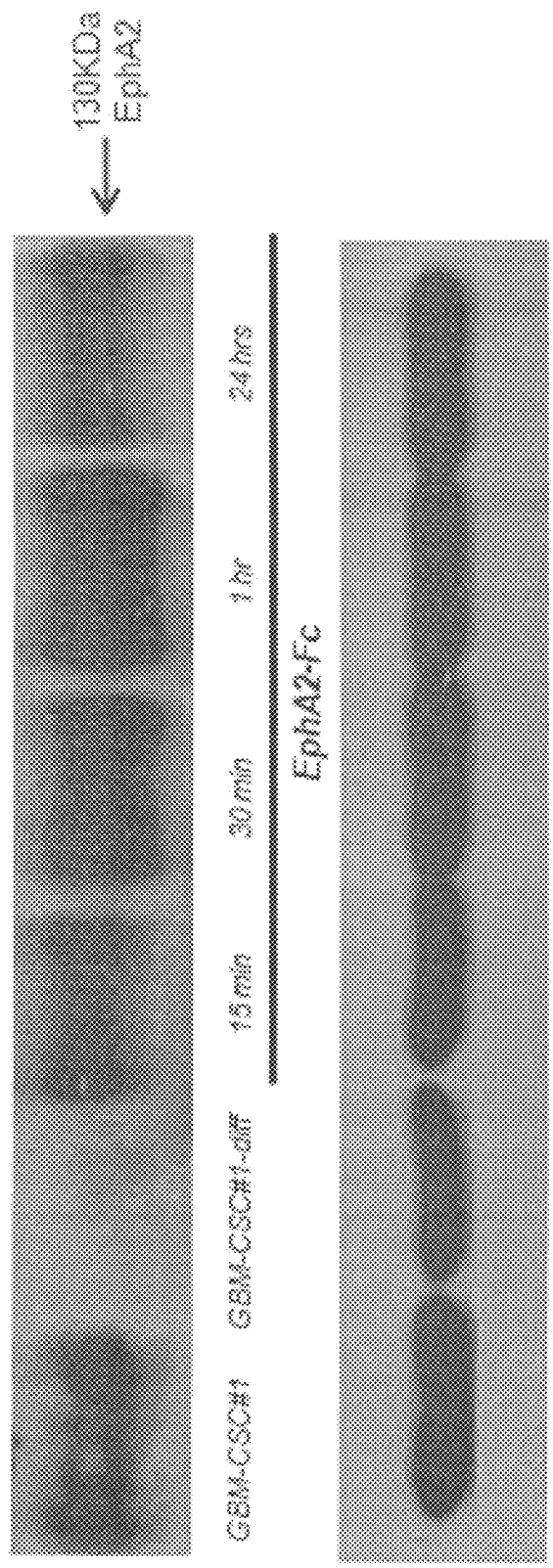

Finally, as shown in FIG. 3H, EphA2-Fc treatment might prevent endogenous EphA2 phosphorylation rather than down-regulating EphA2 protein expression in GBM-CSCs. Resting GBM-CSCs and GBM-CSCs activated with EphA2-Fc (5.0 μg/mL) at the indicate periods were subjected to Western blot analysis.

Note that no EphA2 receptor expression level was detected in differentiated GBM-CSCs, thus indicating its putative involvement in the regulation of GBM cancer stem cells oncogenic behavior, such as aberrant proliferation and migration. The immunoblot presented is a representative of three blots each analyzed at different times.

Example 5

Effects of EphrinA1-Fc or EphA2-Fc Receptor on Human GBM-CSCs Proliferation In Vitro To determine whether EphA2 down-regulation/phosphorylation enforcement or the competitive binding with its cognate ligand might affect tumorigenic properties of GBM-CSCs, here the cytostatic effects of ephrinA1-Fc and EphA2-Fc on the first critical stem cell parameter, such as the overall symmetry of division, were analyzed.

GBM-CSC cells in their active state of growth were exposed to soluble ephrinA1-Fc or to EphA2-Fc and then deviation from the kinetic was evaluated.

Growth Curves:

To analyze GBM-CSC cells proliferation index, neurospheres suspensions were transferred to 15 mL tubes (BD), centrifuged at 192×g for 10 minutes and mechanically dissociated to a single-cell suspension. By trypan blue exclusion cells were counted and $8\times10^3$ cells/cm$^2$ viable cells were plated in the presence of mouse monoclonal IgG1 isotype control (R&D), ephrinA1 (0.5, 1.0, 2.0, 3.0 or 5.0 μg/mL) or EphA2-Fc (5.0 μg/mL). The total cell number obtained at the following subculturing step (0 DIV) was plotted. At each subculture passage (every 4-6 days) single-cell suspension was obtained and the total number of viable cells was counted by trypan blue exclusion. $8\times10^3$ viable cells/cm$^2$ were re-plated under the same conditions. This lead to the definition of kinetic parameters (slope of the growth curve, as in Gritti A, 2001) (7.) that provided indications of the role of the above mentioned recombinant proteins in determining CSCs-HNSCs expansion rate. U87 cells as reference control for tumor cells and HNSCs for neural stem cells.

To assess whether the outcome of ephrinA1-Fc and EphA2-Fc treatments was on bona fide stem cells, proliferation analysis with acutely dissociated cells were performed by sub-culturing GBM-CSCs soon after isolation from the primary tumor specimens (as described above) in the presence of EphA2-Fc (5.0 μg/mL).

KI67 Immunoreactivity:

The investigation was complemented by definition of the proliferation index with KI67 analysis (1.). Briefly, cells were seeded onto Cultrex-coated (Trevigen) glass coverslip in the presence of EGF/FGF2 and exposed to ephrinA1-Fc (0.5, 1.0 μg/mL) for 24 hours. Proliferating cells were quantified by indirect immunocytochemistry using an IgG rabbit polyclonal anti-Ki67 (1:1000, Novocastra). A Cy2 goat anti-rabbit secondary antibody was used as described above (1:200, Jackson Immunoresearch). The total number of cells in each field was determined by counterstaining cell nuclei with 4,6-diamidine-2-phenylindole di-hydro-chloride (DAPI; Sigma; 50 g/ml in PBS) for 10 min at room temperature.

BrdU Assays:

Proliferation was also monitored by BrdU colorimetric assay kit according to the instructions provided by the manufactures (Roche). In brief, GBM-CSCs were plated in 96-well microplate, at a density of 5000 cells/well. The cells were exposed to ephrinA1 (0.001, 0.01, 0.1, 0.5, 1.0 μg/mL) for 24 hours and thereafter 24 hours to BrdU (1:10). Cell proliferation index was assessed in triplicate.

Figure 4A:
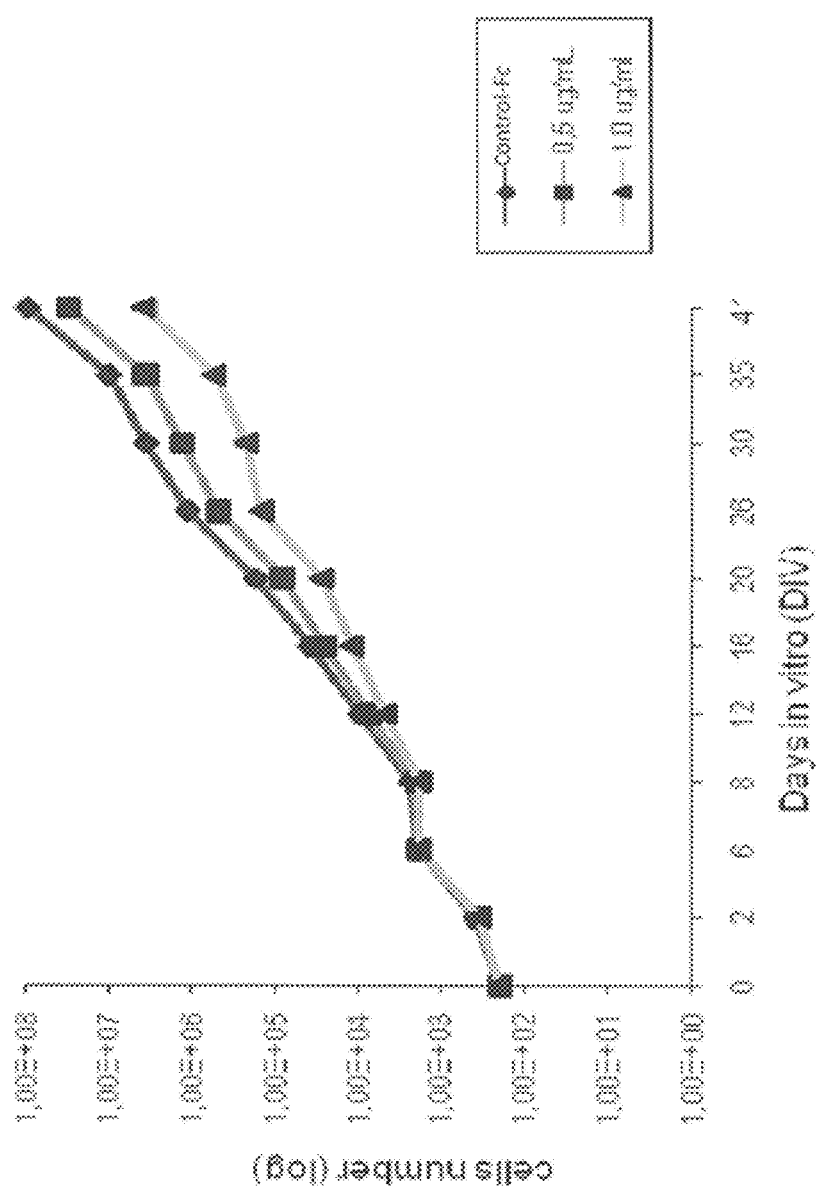
Figure 4B:
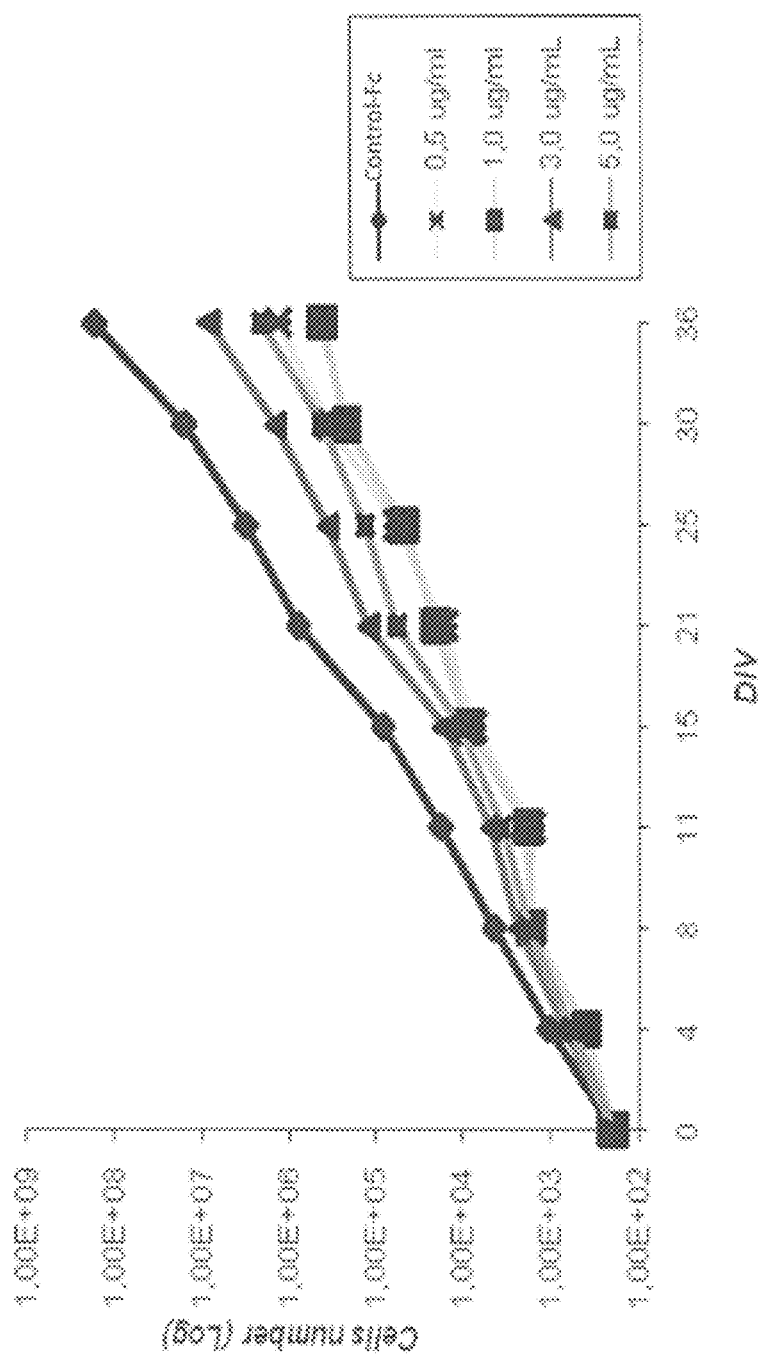
Figure 4C:
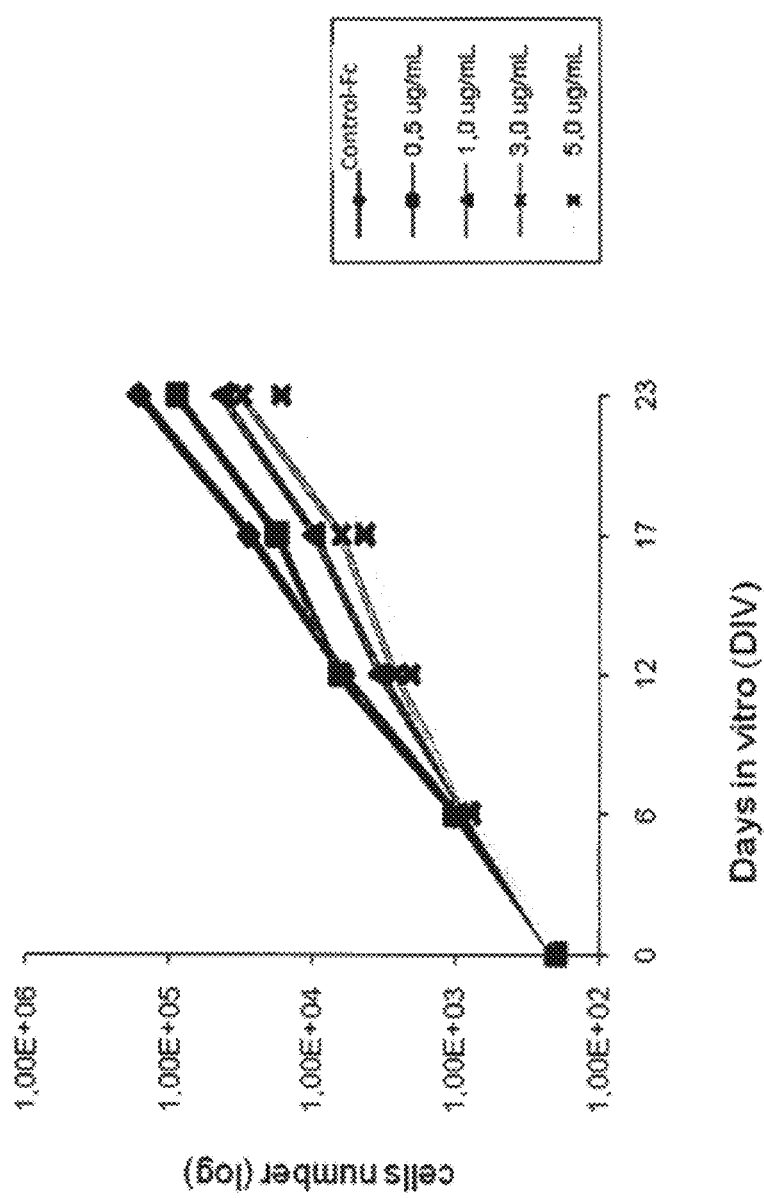
Figure 4D:
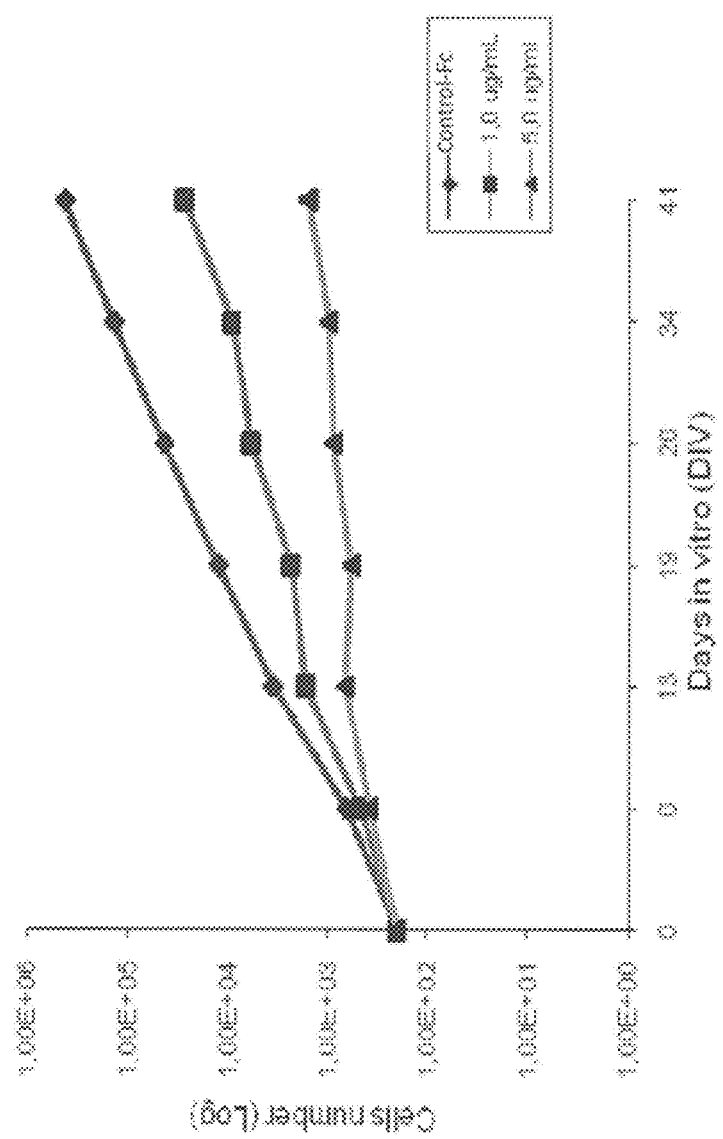
Figure 4E:
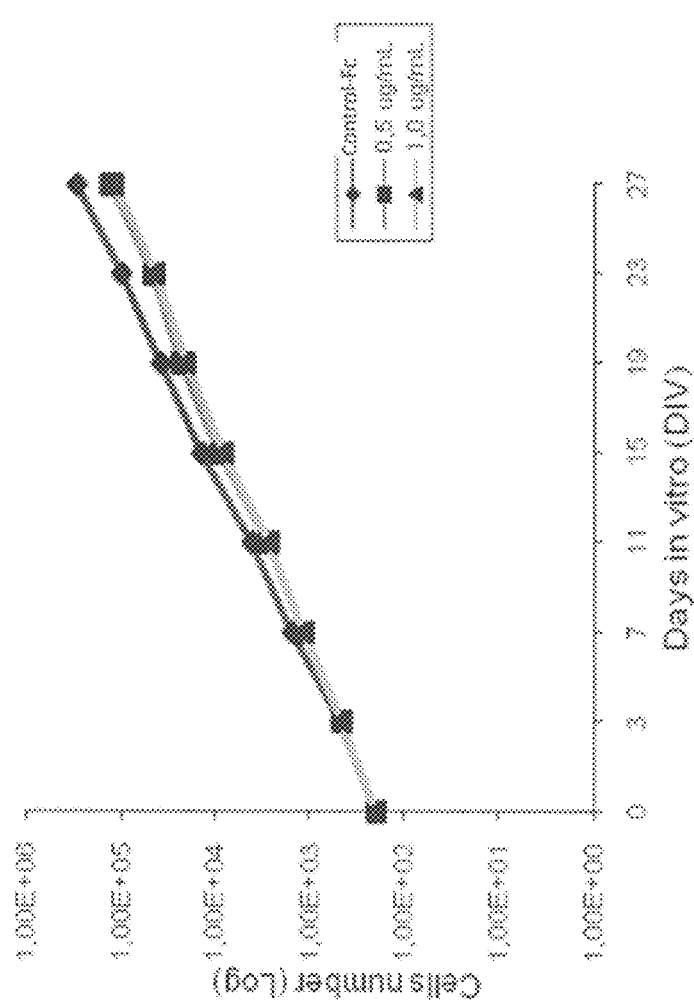
Figure 4F:
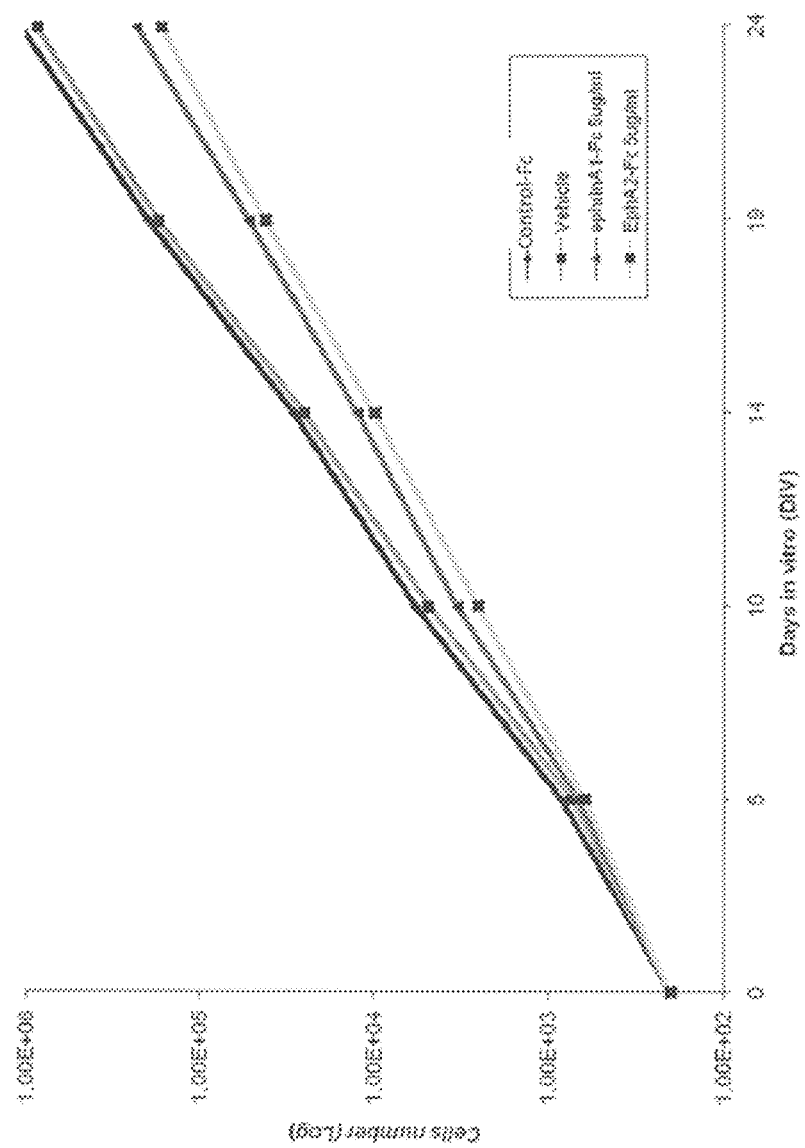
Figure 41:
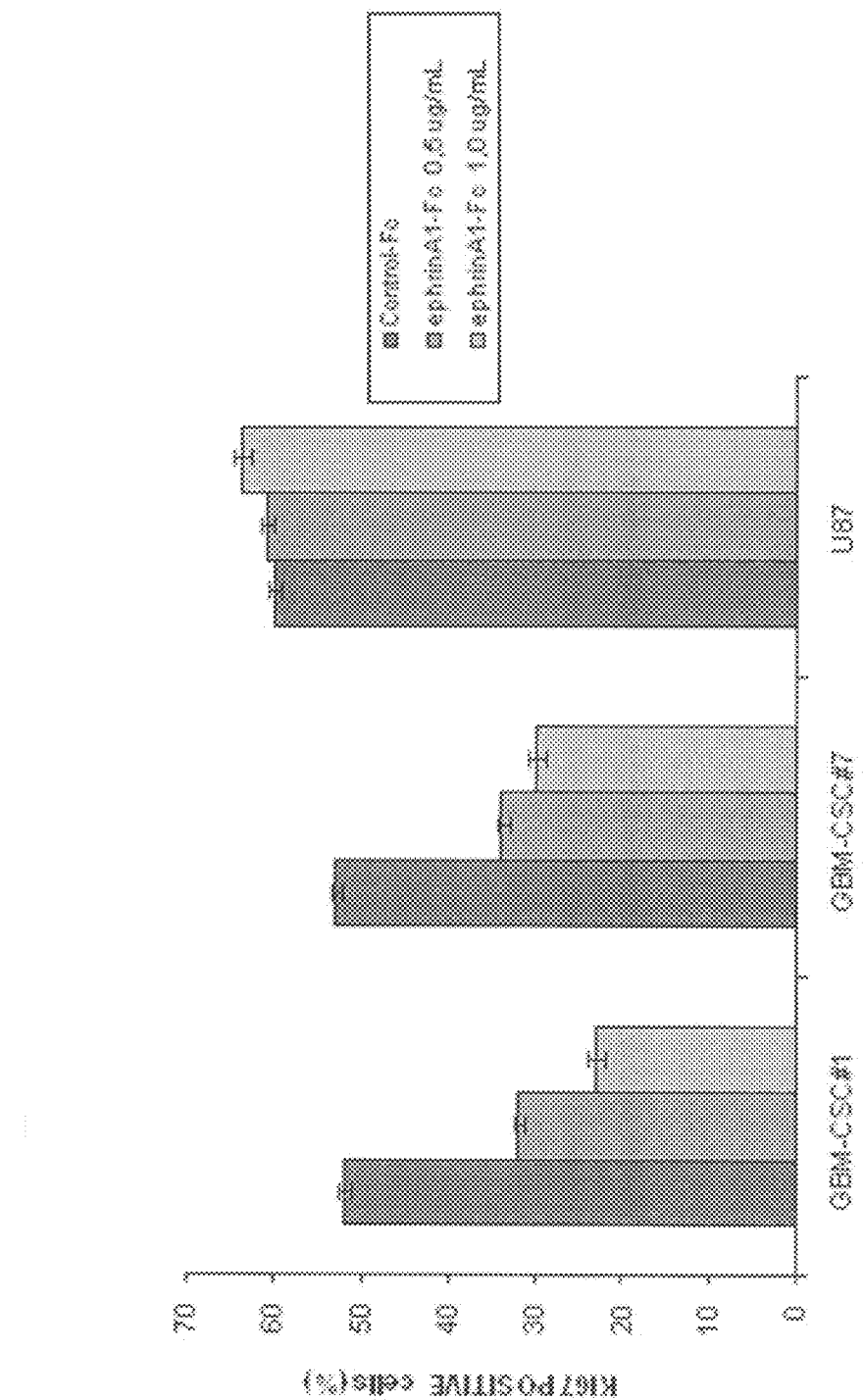

Results:

As clearly showed by growth kinetics studies in FIGS. 4A-4F, activation and rapid internalization of EphA2 receptor caused by ephrinA1-Fc ligand greatly decreased GBM-CSC lines proliferation index. Relative to cells grown with an isotype control (Fc), differences in the growth kinetics were detected after ephrinA1-Fc addition to the GBM-CSC cells in culture FIGS. 4A-4C, similar to human neural stem cells FIG. 4D but unlike U87 human glioma lines FIG. 4E. EphrinA1-Fc attenuates GBM-CSC cells proliferation in a concentration dependent manner. Growth curves are representative of three GBM-CSCs lines. FIG. 4F Relative to cells grown with ephrinA1-Fc, EphA2-Fc showed to induce a great reduction of the GBM-CSCs growth kinetics. This data might suggest once more a functional role for ephrinA1-Fc and EphA2-Fc in depleting the GBM-CSCs pool. All the graphs showed are representative of three experiments. Growth curves in f are representative of one GBM-CSC cell line.

As reported in FIGS. 4G-4I, either BrdU incorporation (FIG. 4G, FIG. H) or KI67 immunoreactive cells (FIG. 4I) was greatly reduced in the presence of soluble ligand at the indicated concentrations. EphrinA1-Fc does not elicit any inhibitory effect on U87 cells proliferation. (FIG. 4G, FIG. 4H) is representative of one GBM-CSC cell line. The data represented is mean±s.e.m. from four independent experiments.

FIGS. 4J-4M clearly shows that exposure of GBM-CSC cells to EphA2-Fc (5.0 μg/mL) soon after isolation from the primary tumor specimen prevented their expansion in culture. Phase-bright microscopy images of neurospheres from two acutely dissociated GBM-CSC lines in the absence (FIG. 4J, FIG. 4K) or in the presence (FIG. 4L, FIG. 4M) of EphA2-Fc show clear differences in clone morphology. Untreated GBM-CSC-derived clones exhibit the typical rounded morphology, whereas neurospheres obtained following EphA2-Fc treatment were irregularly shaped and characterized by the presence of many protruding elongated cells, suggestive of increased cell adhesion and probably differentiation (n=4). Bar, 50 μm.

Example 6

Effects of Soluble EphrinA1-Fc or Soluble EphA2-Fc Receptor on Human GBM-CSCs Clonogenicity and Self-Renewal Capacity The ability of GBM CSCs to self-renew, which can be defined as the ability of a cancer stem cell to produce multiple copies of itself over a given time, is a prospective index of how aggressive their behaviour may be. Here a critical stem cell parameter related to the overall symmetry of division, such as related self-renewal activity, was analyzed.

The self-renewal index after ephrinA1-Fc or EphA2-Fc exposure was assessed by means of clonogenic assays and GBM-CSC cells sorting.

Clonogenic Assay:

GBM-CSC lines derived from the dissociation of single clones were counted and 1000 viable cells/well were seeded in L-poly-Lisin-coated (0.1 mg/mL, Sigma) 24-well plates. The number of secondary spheres generated was assessed after 7-10 days (7.). Cells were plated in the presence of mouse monoclonal IgG1 isotype control (R&D), ephrinA1-Fc (0.5, 1.0, 2.0, 3.0, 5.0 μg/mL) or EphA2-Fc (5.0 μg/mL). HNSCs were employed as stem cells control.

Cell Sorting:

$2\times10^6$ GBM-CSC cells were centrifuged and resuspended in 0.5 mL complete medium with DNase (1:1000, final concentration 1 μg/mL, Sigma).

GBM-EphA2 receptor positive or negative cells were then sorted and analyzed (FACSAria, BD Biosciences) using single cell sort mode and ACDU (Automated Cell Deposition Unit) to sort a single cell in each well of the 96 multiwell plates.

FACS Aria was equipped with 488, 633 and violet lasers. Cells were identified and electronically gated on forward and orthogonal light scatter signals. Events representing cells binding anti-EphA2 were identified by their light scatter (FSC and SSC) and fluorescence signatures (FITC). As many as three cell populations were sorted simultaneously. The instrument raw data were stored electronically for archiving and data processing.

The number of primary spheres generated (clonal efficiency) in each well was assessed 10-14 days after plating (DAP).

Figure 5A:
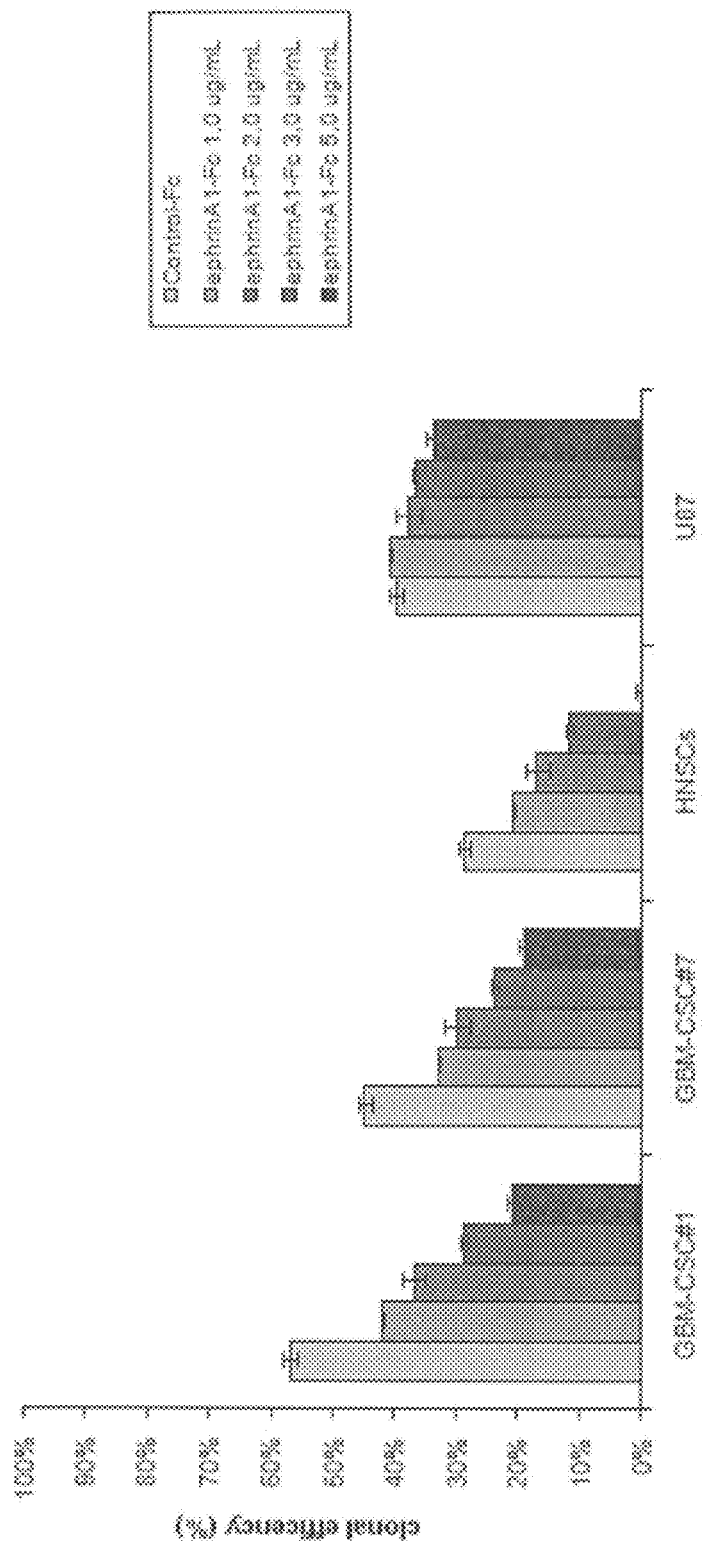

Results:

As shown in FIG. 5A, ephrinA1-Fc affects the overall symmetry of division and the related self-renewal activity in human GBM-CSCs in vitro.

By serial clonogenic assays as described in methods, relative to cells grown with control-Fc GBM-CSCs stimulated with the indicated concentration of soluble ephrinA1-Fc were shown to display a lower clonal efficiency, similar to HNSCs but unlike U87 cells. Ligand-mediated activation of EphA2 reduced in a dose-dependent manner the percentage of neural precursor clone-forming (clonal efficency). Columns, mean of three separate assays, bars, s.e.m.

Furthermore, ephrinA1-Fc induces morphological changes in GBM cells in vitro. Phase-bright microphotographs of neurospheres from two GBM-CSC line cultures, reported in FIGS. 5B-5G, show clearly the effects of ephrinA1-Fc on clone size. (FIG. 5B, FIG. 5C) resting controls, (FIG. 5D, FIG. 5E) ephrinA1-Fc 0.5 μg/mL, FIG. 5F, FIG. 5G ephrinA1-Fc 1.0 μg/mL. This might confirm the putative involvement of ephrinA1-Fc in depleting the GBM-CSCs pool. Notably, ephrinA1-Fc saturating dose (54/mL) completely abolished HNSCs neurospheres formation (data not shown). Scalebar 100 μm (FIG. 5B, FIG. 5D, FIG. 5F); 50 μm (FIG. 5C, Fig. E, FIG. 5G).

Figure 5H:
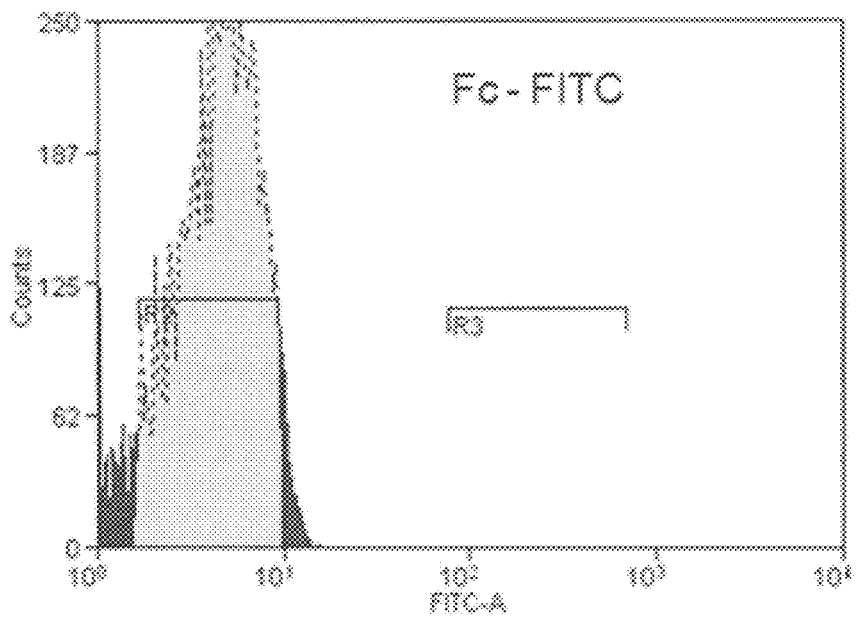
Figure 5I:
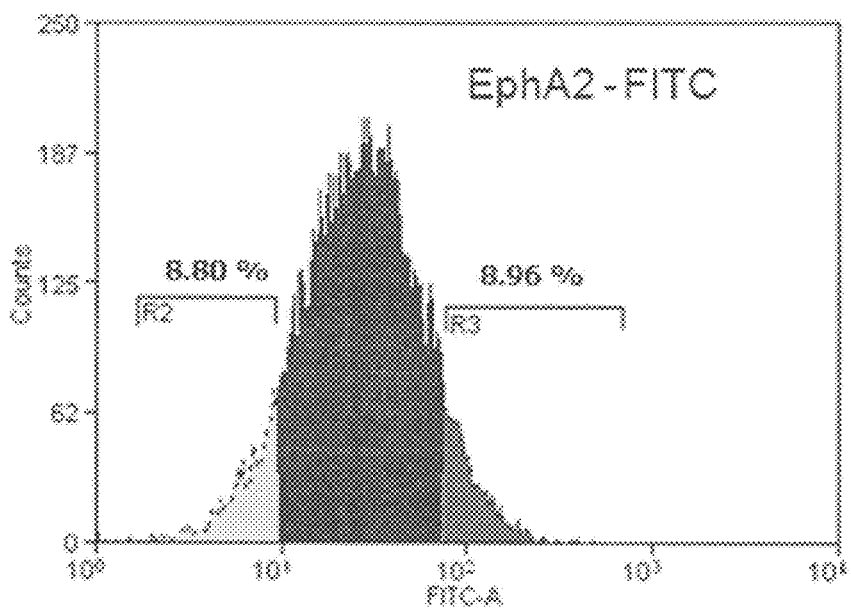
Figure 5J:
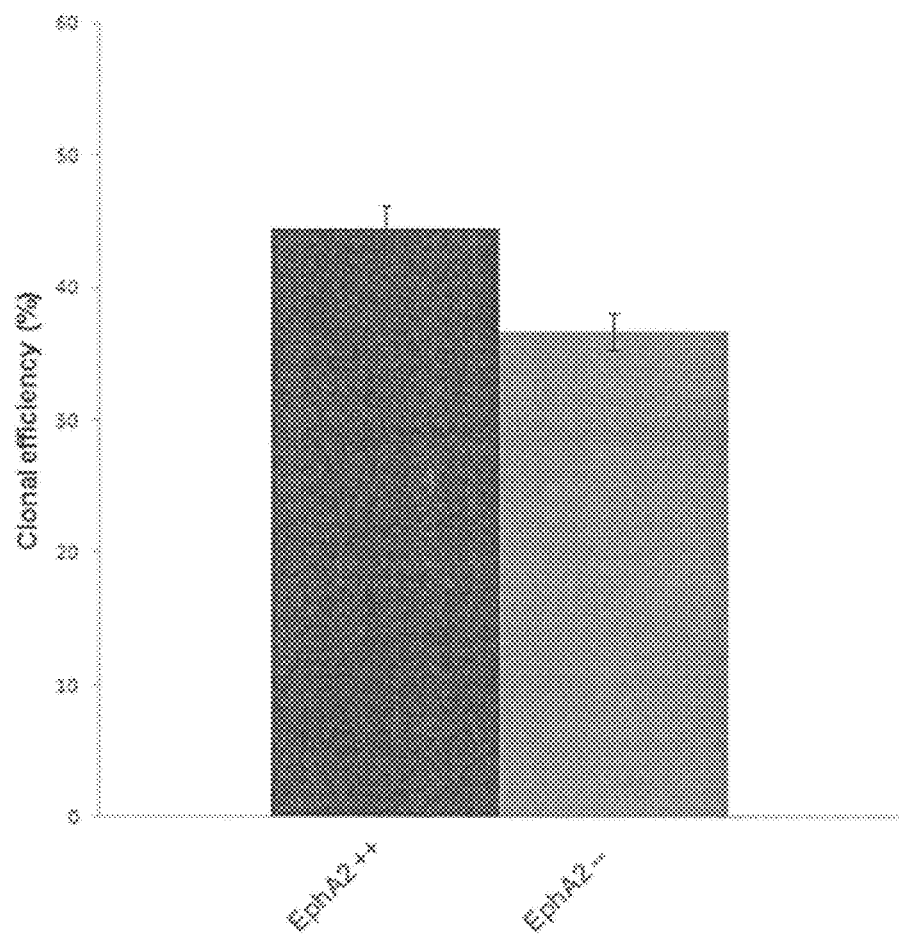

Finally, as reported in FIGS. 5H-5J, EphA2/cell sorting was performed and EphA2 positive subpopulation was remarkably more clonogenic in respect to EphA2 negative cells in vitro. Columns, mean of five separate assays, bars, s.e.m.

Example 7

Soluble EphrinA1-Fc Ligand or Soluble EphA2-Fc Receptor Effects on the Pool of Tumorigenic GBM-CSCs To assess whether the outcome of ephrinA1-Fc and EphA2-Fc treatment affects bona fide stem cells, rather than wave committed progenitor cells, ephrinA1-Fc and EphA2-Fc effects on GBM CSCs side population (SP) were investigated.

In addition, EphA2-Fc stimulated GBM-CSCs (5.0 μg/mL for 24 hours) were characterized for the expression of putative neural stem cells, brain tumor stem cells and cancer stem cells/tumor-initiating cells population markers by FACS.

Side Population:

The SP cells were identified as a characteristic low-fluorescence tail in the dot plot of dual-wavelength analysis and detected in our GBM-CSCs (1.41% of the live-gated cells, versus 0.03% in bone marrow) Treatment with verapamil, which is known to inhibit specific ABC transporters that mediate Hoechst 33342 expulsion, abolished this population. Cells were analyzed in Moflo (Coulter) using dual-wavelength analysis (blue, 450-465 nm; red, 630-730 nm) after excitation with 350 nm UV light.

Cells were grown in the presence of 5.0 μg/mL of ephrinA1-Fc or EphA2-Fc for 24 hours and then resuspended at a final concentration of $2\times10^6$/mL in DMEM/F12 plus DNase (1 μg/mL, Sigma), BSA (2 mg/mL, Sigma), heparin (4 μg/mL, Sigma) and EDTA (200 μg/mL, Sigma). GBM-CSCs were then labeled with 2 μg/mL Hoechst 33342 dye (Invitrogen) at 37° C. for 2 hours with intermittent mixing. As an inhibitory control, calcium channel blocker verapamil (Sigma) was added at a final concentration of 50 μM for 10 min at room temperature before labeling with Hoechst 33342.

At the end of the incubation, cells were spun down in the cold and resuspended in ice-cold PBS. Propidium iodide (PI) (2 μg/mL, final concentration, Sigma) was added 5 min at room temperature before fluorescence-activated cell sorting (FACS) analysis, which allows for the discrimination of dead versus live cells.

The ABC transporter gene, ABCG2 (also known as Bcrpl), is one of the primary mediators of the SP phenotype in mouse bone marrow and other tissues. We detected ABCG2 protein in GBM-CSC cells performing immunofluorescence staining using the mouse monoclonal IgG2b antibody (1:50, eBioscience) and an alexa Fluor 488-conjugated secondary goat anti-mouse antibody (1:2000, Invitrogen) as described above.

Flow Cytometry Immunophenotype Profiling:

Flow cyotmetry analysis was performed as described above. The following primary conjugated antibodies were employed:
  mouse anti CD133-PE conjugated (0.25 μg, MACS)
  mouse anti CD44-PE conjugated (20 μL/1×$10^6$ cells, BD)
  mouse anti CD184-CXCR4-APC conjugated (20 μL/1× $10^6$ cells, BD)

mouse anti CD81-TAPA1-FITC conjugated (20 μL/1×10⁶ cells, BD)

mouse anti CD15 SSEA1-FITC conjugated (20 μL/1×10⁶ cells, BD)

mouse anti CD117-cKit-PE conjugated (0.2 μg, BD)

Cells were incubated for 30 min in the dark at room temperature, washed and resuspended in 0.5 mL complete medium and analyzed by flow cytometry. Autofluorescence and isotype controls were run routinely for all these assays.

Figure 6:
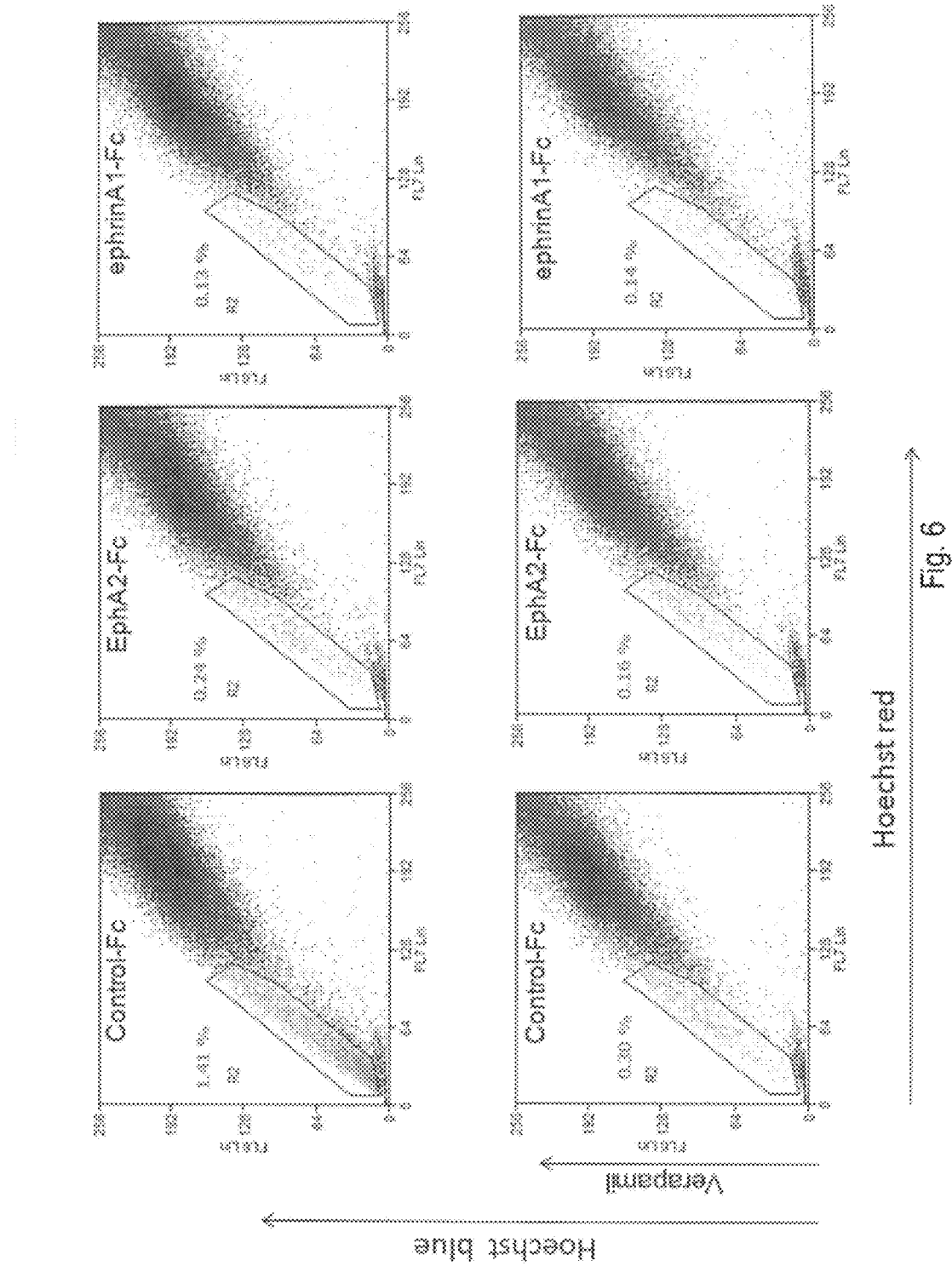
FIG. 6: shows the side populations (SP) analysis as described in Example 7.

Results:

As clearly reported in FIG. 6 the GBM-CSCs SP completely disappeared or was greatly reduced by treatment with ephrinA1-Fc and EphA2-Fc.

Cells were labeled with Hoechst 33342 either alone or in combination with 100 μmol/L verapamil and then analyzed by flow cytometry. GBM-CSCs treated with either soluble ligand or receptor showed a side population cells that were not detectable as well as in the presence of verapamil. Data shown are representative dot plots of at least 2 independent experiments.

EphA2-Fc might have an involvement in tumor stem cells or tumor-initiating cells subpopulation enrichment. The amount or the pattern of the expression of some markers was decreased after EphA2-Fc stimulation (data not shown).

Example 8

Effects of Soluble EphrinA1-Fc or Soluble EphA2-Fc Receptor on Human GBM-CSCs Multipotentiality To be qualified as stem cells, a GBM-CSCs must be multipotent. Here differentiation studies were undertaken to determine the candidate acquisition of a more differentiated phenotype in GBM-CSCs following ephrinA1-Fc or EphA2-Fc treatment. Clonal spheres grown in the absence or in the presence of ephrinA1 or EphA2-Fc were subjected to cytofluorimetric measurement of fluorescence signal intensity.

Flow Cytometry:

Clonal spheres from the self-renewal assay were subjected to FACS analysis and neural markers expression was assessed using lineage-specific markers.

For astrocytes (glial fibrillary acidic protein, GFAP), neurons (βIII-tubulin) and oligodendrocytes (galactocerebrosideC, GalC) quantification, a rainbow calibration particle mixture (8 peaks), 3.0-3.4 μm (BD Bioscience) was used for calibration, and the intensity of cell labeling was expressed as molecules of equivalent phycoerythrin (MEPE) or molecules of equivalent fluorescein (MEFL). Briefly, for intracellular staining cells were plated in the presence of 1.0 or 5.0 μg/mL ephrinA1 for 24 hours, then resuspended and permeabilized by 0.5 mL of Cytofix/Cytoperm solution (BD) at room temperature for 30 min. Cells were washed with 2 mL of BD Perm/Wash 1× (BD) and incubated at room temperature for 10 min. After centrifugation, they were resuspended in 0.2 mL BD Perm/Wash solution 1× (BD) containing the appropriate primary antibody mix. For membrane antigens, cells were resuspended in 0.2 mL of growth medium and then incubated for 30 min at 4° C. with the following primary antibodies: rabbit polyclonal anti-GFAP (1:400, Dako Corporation), mouse monoclonal anti-bIII tubulin (1:400, Babco) and mouse monoclonal anti-GalC (1:400, Chemicon). Cells were washed and exposed for 30 min at +4° C. to secondary antibody. In the case of intracellular antigens these were 1:800 goat anti-rabbit Ig FITC-labeled or goat anti-mouse IgG R-PE-labeled antibody (BD), while for membrane antigens 1:1000 FITC-conjugated F (ab') 2 goat anti-mouse IgM or FITC-conjugated goat anti-mouse IgM (Jackson ImmunoResearch) were used. After extensive washing, cells were resuspended and analyzed by flow cytometry.

Results:

As shown in FIGS. 7B-D relative to control-Fc, both soluble ligand and receptor induced overt morphological changes in GBM-CSCs. By using cytofluorimetry measurement of fluorescence signal intensity, cells stimulated with ephrinA1-Fc revealed a dose-dependent increase in the molecules of equivalent fluorescin (MEFL) for glial (GFAP) immunoreactivity. EphrinA1-Fc and EphA2-Fc trigger the acquisition of a more mature phenotype in vitro, which predominantly acquire an astroglial-like fate and depletes the pool of tumorigenic GBM-CSCs. The histogram (FIG. 7A) shows mean±s.e.m. from triplicate measurement.

Example 9

Effects of Soluble EphrinA1-Fc or Soluble EphA2-Fc Receptor on Human GBM-CSCs Apoptosis or Cell Cycle Cell Cycle Analysis: BrdU/DNA Analysis and Detection For cell cycle analysis, 1×10⁶ cells/sample were cultured in the presence of ephrinA1-Fc (5 μg/mL) or EphA2 (5 μg/mL) for 6, 24, 48 hours. Cells were then exposed to 20 μM 5-bromo-2-deoxyuridine (BrdU, 1:500, Sigma) for 20 min at 37° C., fixed in 70% ethanol in PBS and kept at 4° C. before staining (3.). DNA was denatured with 1 mL of 3N HCl for 20 min RT and then the pellet incubated with 1 mL 0.5% Tween-20 (Sigma) containing 1% of BSA (Sigma) for 15 min at RT. Cells were then incubated with anti-BrdU monoclonal antibody (1:10, BD) for 60 min at RT in the dark. The secondary antibody employed was Alexa 488 goat anti-mouse IgG (1:500, Invitrogen). The cells were then resuspended in 2.5 μg/mL of propidium iodide (PI) in PBS and 7 μL RNAse (3 mg/mL) in water, and stained overnight at 4° C. in the dark. Bi-parametric BrdU/DNA analysis were performed with at least 30000 cells for each sample by the FACSCalibur (BD Biosciences) and the data were analyzed using Summit 4.3 software.

Terminal Deoxynucleotidyl Transferase-Mediated dUTP-FITC Nick-End Labeling Assay (TUNEL)

Apoptosis was measured using the TUNEL assay kit (Roche Diagnostics) following the manufacturers' instruction for dual parameter flow cytometry. Analysis was performed on a FACSCalibur (BD Biosciences) and the data were analyzed using Summit 4.3 software (Coulter).

Results: As measured by FACS-Tunel and BrdU, relative to control cells, neither soluble ligand nor soluble receptor induce cell death/apoptosis or change GBM-CSCs and HNSCs cell cycle phases (data not shown).

Example 10

Effects of Soluble EphrinA1-Fc or Soluble EphA2-Fc Receptor on GBM-CSCs Spreading and Migration and on the Related Intracellular Pathways Involved EphA2 overexpression or lack of activation is an integral player also in GBM-CSC cells invasion, causing cytoskeletal modifications or sustaining phosphorylation and kinase activity of FAK and of other intracellular pathways.

Since cell motility depends on cytoskeletal modifications, the oncogenic-suppressing role of ephrinA1-Fc and EphA2-Fc in blocking GBM-CSCs cytoskeleton rearrangements and morphological changes was evaluated by measuring the frequency of cells displaying F-actin ring bundles by phalloidin.

The efficiency of soluble ligand or receptor in regulating vascular cells motility and invasion capacity was also determined.

Immunostaining for Cytoskeleton Markers:

GBM-CSCs were plated at a density of $2.5 \times 10^4$ cells/cm$^2$ onto Cultrex-coated glass coverslips (12 mm diameter) in the absence or in the presence of ephrinA1-Fc (5.0 µg/mL) or EphA2-Fc (5.0 µg/mL) for 5 and 30 min. For F-actin staining, cells were fixed in 4% paraformaldehyde for 20 minutes, permeabilized with 0.1% (v/v) Triton-X 100 and incubated with Alexa555-labeled phalloidin (1:40, Invitrogen) for 30 minutes at room temperature.

Migration Assays:

Invasion assays were performed in 24-well Transwell chambers (8-um pore size, 6.5 mm, 0.33 cm$^2$, Corning Costar) as in Pennacchietti 2003 (10.). The upper side of the filters was coated with Cultrex and $1 \times 10^5$ Human Dermal Microvascular Endothelial cells (HMVECs) were seeded in 1.5 mL DMEM/F12 in the absence or in the presence of EphA2-Fc (5.0 µg/mL). In the lower compartment, as positive stimuli of migration, vascular endothelial growth factor (VEGF, 20 ng/mL) or GBM-CSC cells conditioned medium (1 mL from $1 \times 10^6$ cells 1 day after plating). Stimuli were added in 2.6 mL DMEM/F12 basal medium in the absence or in the presence of EphA2-Fc on the upper side of the filter.

7-14 days after plating, cells on the upper side of the filters were mechanically removed, and those migrated onto the lower side were fixed and stained by using DiffQuick (Dade Behring) following the manufacturers' instruction. Migration of cells was evaluated by volume density values acquired by a densitometer scanner.

Western Blot:

To determine the outcome of ephrinA1-Fc or EphA2-Fc treatment on GBM-CSCs malignant behaviour, cells were seeded in the presence of ephrinA1-Fc (1.0 or 5.0 µg/mL) or EphA2-Fc (5.0 µg/mL) for the appropriate time and then lysated. All the procedures were performed as described above.

The following primary antibodies were employed:
rabbit anti-phospho FAK (Tyr576/577, Tyr 925) (1:1000, Cell Signaling)
rabbit anti-human total p42/p44 MAPK (ERK1/2) (1:1000, Cell Signaling)
rabbit anti-human phospho ERK1/2 Thr202/Tyr204) (1:1000, Cell Signaling)
rabbit anti-phospho Akt (Ser473) (1:1000; Cell Signaling)
rabbit anti-phospho mTOR (Ser2481) (1:1000, Cell Signaling)
rabbit anti-phospho PI3K p85 (Tyr458)/p55 (Tyr199) (1:1000, Cell Signaling)
rabbit anti-human E-cadherin (1:1000, Cell Signaling)
mouse anti-human gelsolin (1:1000, Sigma)

This step was followed by incubation with donkey anti rabbit HRP (1:10.000, GE) and rabbit anti mouse HRP (1:10, 000, GE).

Human Brain Protein Medley (70 µg, Clontech) or human brain tumor total protein lysate LYS054 (70 µg, Abserotec) were used as tissue controls.

Phosphorylated forms of ERK1/2 were detected also by immunocytochemistry. Cells were seeded onto Cultrex-coated (Trevigen) glass coverslip in the absence or in the presence of ephrinA1-Fc (5.0 µg/mL) or EphA2-Fc (5.0 µg/mL) for 1, 6 and 24 hours. Resting cells or cells pre-treated with MEK1/2 inibitor UO126 (100 for 2 hours, Cell Signaling) as control. Immunocytochemistry was performed with a rabbit polyclonal anti phospho-MAPK (t202/y204) (1:1000, Cell Signaling) and Alexa Fluor 488 IgG (1:2000, Invitrogen) as described above.

Results:

Either soluble receptor or soluble ligand prevents cell spreading. Adhesion and spreading proceed concomitantly with changes in both the actin an microtubule cytoskeleton. Cytoskeleton rearrangements analysis reported in FIG. 8A, clearly show that untreated GBM-CSC cells FIG. 8A, which have a highly migratory phenotype and spread well on Cultrex, are characterized by a flat and polygonal morphology, with a well-organized actin cytoskeleton, more F-actin filaments densely organized in stress fibers and a fibroblast-like morphology. (FIGS. 8B-8D insets) Ring-like actin bundles characteristics of the GBM-CSCs behaviour. Conversely, ephrinA1-Fc FIG. 8E and EphA2-Fc FIG. 8F treated cells remained rounded, characterized by bipolar and elongated cells and failed to spread, revealing less organized microtubules with focal F-actin positivity at the cell-cell contacts. Bar in FIG. 8A, FIG. 8E, and FIG. 8F, 5 µm; Bar in FIG. 8B, FIG. 8C, and FIG. 8D, 10 µm.

Data shown in the FIG. 8G, confirm that EphA2 activation might inhibit cell adhesion, spreading and migration in vitro, inducing FAK rapid inactivation and dephosphorylation. Cells were grown in the absence (−) or in the presence (+) of ephrinA1-Fc for the indicate periods of time, and then lysated. The decreased expression of phosphorylated FAK at the tyrosine residues 576/577 or 925 in treated cells was assessed at the protein level by Western blot. The most marked level was observed 60 min after treatment and after 24 hours, FAK is tyrosine phosphorylated again. Loading control: GAPDH.

Notably, as indicated by cultrex invasion assays reported in FIGS. 8H-8M, also EphA2-expressing endothelial cell in vitro migration was severely inhibited by administration of recombinant EphA2-Fc. Serum starved HMVECs were plated in the top of the chamber and allowed to migrate to the underside of the filters for 6 hours. FIG. 8H HMVECs in basal medium as control. In the low compartment VEGF (20 ng/mL) or GBM-CSCs conditioned medium respectively in the absence (FIG. 8I, Fig. J) or in the presence (FIG. 8L, FIG. 8M of EphA2-Fc (5.0 µg/mL) in the upperside of the chamber. Control human IgG in the upperside did not affect cell migration in response to VEGF FIG. 8K. Cells that migrated to the lower surface of the membrane were fixed and stained as described in the methods. Scale bar, 200 µm.

Finally, it has been demonstrated that ephrinA1-Fc and EphA2-Fc might elicit activation of MAP kinase-dependent pathways by the phosphorylation of ERK1/2 in GBM-CSCs. As reported by confocal immuno-fluorescence in FIGS. 8N-8R, relative to Fc-treated control (FIG. 8N), a specific prompt increase in the frequency of phosphorylated ERK1/2 positivity could be detected 6 hours after EphA2-Fc (FIG. 8O) or ephrinA1 Fc (FIG. 8Q) addition in the growth medium. The average level of positivity observed remained stable for 24 hours. (FIG. 8P) Soluble ligand and receptor mediated phosphorylation at ERK substrate sites is abolished by pretreating cells with U0126, a chemical inhibitor of MEK1 activation. Scale bar, 20 µm. Western blot analysis reported in FIG. 8R confirm that that increasing concentrations of ephrinA1-Fc enhance ERK1/2 activation in GBM-CSCs. GAPDH provided a control for sample loading. ephrinA1-Fc might even enhance MAPK downstream signaling, as intense activation of Akt and mTOR was detected (data not shown).

Example 11

BMP4 drives a pro-differentiation cascade of events that leads to the depletion of the cancer stem cell pool in GBMs, both in vitro and in vivo (11.). Below is the effect of combined BMP4 and ephrinA1-Fc treatments.

Real-Time PCR:

GBM-CSC cells were exposed forty-eight hours to recombinant human BMP4 (100 ng/mL, R&D). Total RNA and cDNA were obtained as described previously and then a quantitative analysis for EphA2 expression was performed. Quantitative RT-PCR reactions were run in triplicate using Brilliant SYBR Green QPCR Core Reagent Kit (Stratagene). SYBR Green dye binds to any PCR product, and therefore does not require the use of sequence-specific probes. Fluorescent emission was recorded in real-time (Chromo 4 Four-Color Real-Time PCR Detector, MJ). Gene expression profiling was completed using the comparative Ct method of relative quantification. Relative RNA quantities were normalized to two endogenous controls, GAPDH and 18S ribosomal RNA (18S rRNA).

Growth Curves:

GBM-CSCs were seeded in the presence of ephrinA1-Fc (1.0 µg/mL or 5.0 µg/mL) and of respectively BMP4 (100 ng/mL, R&D) or leukemia inhibitor factor (LIF, 10 ng/mL, Chemicon), a strong regulator of neuronal differentiation in human CNS stem cell progeny. Cell proliferation index was evaluated with growth curves analysis as described above.

Results:

As shown in FIG. 9A, FIG. 9B, rhBMP4 exposure prompts EphA2 protein downregulation in GBM-CSCs through the differentiation and the depletion of the GBM-CSCs pool. FIG. 9A QRT-PCR analysis with specific primers revealed decreased EphA2 transcript, normalized with GAPDH, in rhBMP4-treated cells as compared with matched controls. The histogram shows normalized means±s.e.m. quantified from 3 different experiments representative of two GBM-CSC lines. Furthermore, as reported in FIG. 9B rhBMP4 elicits ephrinA1-Fc inhibitory effects on GBM-CSCs and HNSCs proliferation. Differences in the growth kinetics were detected between GBM-CSCs grown with ephrinA1-Fc in the absence or in the presence of rhBMP4, with the former characterized by faster growth rate and the latter comprising slowly-dividing GBM-CSCs. Growth curves in b are representative of one GBM-CSC line.

Example 12

Effects of EphrinA1-Fc and EphA2-Fc Administration on Human GBM-CSCs Subcutaneous (s.c.) Tumor Xenografts Growth It is known that EphA2 overexpression method of causes tumorigenesis. Furthermore the critical stem cell parameters of GBM-CSCs analyzed above, such as the overall symmetry of division and the related self-renewal activity, are linearly correlated with the tumor-initiating ability of these cells. The effects of EphA2 down-regulation of expression or of activity by ephrinA1-Fc or EphA2-Fc were tested in vivo.

Here it has been assessed whether the in vitro reduction of the pool of tumorigenic GBM-CSCs is related to a similar decline in the ability of ephrinA1-Fc or EphA2-Fc-treated cells to form tumors in vivo, in subcutaneous (s.c.) xenografts.

For s.c. injections, immunocompromised athymic nu/nu mice (female 3-4 weeks old, Charles River) were employed. Human GBM subcutaneous tumor xenografts were established by injecting $3 \times 10^6$ hGBM-CSC cells into the right flank of mice as recipients, using a 23-gauge needle, in 100 µL of PBS mixed with an equal volume of Cultrex (Trevigen).

Mice were monitored for 7-35 days, reagents were administrated 1×/day for 35 days near the site of GBM-CSCs injection (peritumoral injection).

To test the ability of soluble ligand/receptor to reduce GBM-CSCs both tumor-initiating capacity and to prevent tumor establishment and growth, animals were randomized into:

Control-vehicle: after cells transplantation they received peritumoral injection of 100 µL of saline solution;

EphrinA1-Fc (co-treated group): transplantation of cells was accompanied at the same time by peritumoral injection of 100 µL of ephrinA1-Fc in saline (10 ug/dose);

EphA2-Fc (co-treated group): transplantation of cells was accompanied by peritumoral injection of 100 µL of EphA2-Fc in saline (10 µg/dose);

EphA2-Fc (post-treated group): tumor were allowed to grow 7-10 days after cells transplantation, then mice received peritumoral injection with 100 µL of EphA2-Fc (post tumor formation) (10 µg/dose).

Tumor measurements were determined with vernier calipers once week and expressed as absolute volumes, as well as normalized to individual tumor volumes at day 1, the initiation of dosing (relative tumor volumes), to assess changes in the rate of tumor growth relative to the treatment.

$$V (\text{mm}^3) = \pi/6 \times a \times b \times c$$

Animal body weights were determined and analyzed over a similar time course.

GBM-CSCs tumor xenografts from control, ephrinA1-Fc and EphA2-Fc-treated animals were excised and then postfixed and cryoprotected as described above.

Ten-micrometer-thick serial sections were immunolabeled with the following antibodies/antisera: mouse IgG1 anti-human nuclei (1:100, Chemicon), mouse IgG1 anti-human mytocondria (1:50, Chemicon) and mouse IgG2a anti-human HLA-abc (1:100, Dako) to confirm the human nature of tumor. Rabbit IgG anti-Ki67 (1:1000, NovoCastra) for proliferation index detection. After thorough rinsing, sections were incubated for 1 h at room with the appropriate secondary antibody: goat anti-mouse or anti-rabbit IgG Alexa Fluor 488-546 (1:1000, Invitrogen). Sections were washed and coverslipped with Fluorsave.

Hematoxilin and eosin staining and immunohistochemistry were performed.

Samples were viewed and photographed with a Zeiss Axiophot-2 fluorescence microscope and Leica DMIRE2 Confocal Microscope. No labeling was ever observed in control experiments when primary antibodies or antisera were omitted or, alternatively, when normal non immune serum was used.

Results:

As clearly shown in FIG. 10A, FIG. 10B, administration of ephrinA1-Fc or EphA2-Fc strongly inhibited tumorigenic ability of human GBM-CSCs and tumor progression in subcutaneous murine model. The delivery of ephrinA1-Fc/EphA2-Fc in vivo prevents subcutaneous tumor establishment and growth. Treating pre-established tumors with soluble receptor produced a major drop of their growth in viva GBM-CSCs were injected into the right flank of nu/nu mice. Saline solution (control-vehicle) or reagents (ephrinA1-Fc or EphA2-Fc co-treatment) were administered daily around the plug (100 µL/dose) starting from cells injection. For post-treatment analysis upon achieving volumes (7 days) tumor bearing nude mice received 100 µL/dose daily. The graph shows means±s.e.m. in the four groups of six mice.

Example 13

Effects of GBM-CSCs Exposure to EphrinA1-Fc and EphA2-Fc In Vitro on Their Ability to Initiate Orthotopical Tumors Xenografts To evaluate antitumor efficacy of soluble receptor and ligand molecules (by EphA2 down-regulation of expression or activity) on tumor growth, a more clinically relevant orthotopic tumor model was employed.

In order to confirm and extend the results obtained in the s.c. model, pre-treatment experiments were performed. After forty-eight hours exposure to soluble ligand or receptor (5.0 µg/mL), GBM-CSCs (infected with the reporter gene of luciferase, luc-GBM-CSCs) were injected into the striatum of scid/bg mice. This allowed to determine whether transient exposure to Ephrin ligand could lessen/abolish tumorigenicity in GBM-CSCs.

GBM-CSCs Lentiviral Infection.

GBM-CSCs were infected with reporter gene firefly luciferase.

Newly generated lentiviral vectors in which synthetic bidirectional promoters mediate the coordinate transcription of two mRNA and enable to efficient dual-gene transfer, were employed. (2.).

This proviral vector consists of a bidirectional promoter made by minimal core promoter elements from the human cytomegalovirus (mCMV) joined upstream, and in opposite orientation, of an efficient promoter, from the human phosphoglycerate kinase (PGK). The vector design makes available the firefly luciferase (f-luc) and the green fluorescent protein (GFP) as promoter genes, which will be exploited i) in vitro, to enrich the transgene-expressing cells by FACS, by limiting dilution or by In vivo Ivis Imaging Xenogen analysis; ii) in vivo, to easily monitor tumor cells distribution within the brain. VSV-pseudotyped third-generation LV will be produced by transient 4-plasmid co-transfection into 293T cells and concentrated by ultracentrifugation.

Expression titer of the vectors was estimated on HeLa cells by limiting dilution. Vector particles were measured by HIV-1 gag p24 antigen immunocapture. Vector infectivity was calculated as the ratio between titer and particle for each vector. GBM-CSC cells were exposed to the supernatant, conditioned by transfected 293T cells overnight, for 16 hours. The medium containing virus was then removed and replaced by fresh medium (luc-GBM-CSCs).

The efficiency of infection was assessed either by counting the number of GFP-expressing cells or by In vivo Lumina analysis.

Bioluminescent cells were serially diluted from 5000 to 100 cells in complete medium into black, clear bottomed, 96-well plates (Nunc). D-luciferin (ONE-Glo, luciferase assay system, Promega) was added 1:1 (v/v) to each well (containing single cells resuspended in 100 µl complete medium) 3 minutes before imaging. Imaging time was 1 min/plate.

GBM CSCs Transplantation into the Striatum of scid/bg Mice.

Luc-GBM-CSC cells were seeded in the absence or in the presence of ephrinA1-Fc (5 µg/mL) or EphA2-Fc (5 µg/mL) 48 hours before orthotopical injection.

3 µL of a $1 \times 10^5$ cells/uL suspension in DMEM with DNAse (1:1000, Sigma) were delivered into the right striatum (0.2 µl/min) by stereotactic injection through a glass electrode connected to a Hamilton syringe. All injections were made over a period of 6 minutes to ensure optimal parenchymal compliance.

Animals were anesthetized with 0.2 ml/kg of a stock solution containing ketamine hydrochloride (8 mg/mL), xylazine (0.8 mg/mL), and 14.25% ethyl alcohol in normal saline injected intraperitoneally.

Heads of anesthetized mice were disinfected with a solution of 70% ethyl alcohol and povidone-iodine. A midline incision was made on the dorsal aspect of the head and the pericranium was swept laterally to expose the bregma.

A 2 mm drill hole was made. Care was taken not to disrupt the dura.

The following coordinates (mm from bregma) were used: anterior-ventral (AV)=0; medio-lateral (ML)=+2.5 mm; dorso-ventral (DV)=−3.0 mm from the skull surface.

The micro-injector needle was retracted and skin closed with 4-0 Vicryl. Animals were monitored daily for any sign of neurological dysfunction.

Evaluation of Tumor Growth by the Xenogen IVIS Lumina System.

Tumor formation, extension and volume were indirectly calculated ones/week by sequential images taken with In vivo Lumina analysis (Xenogen) and compared with those of control animals receiving GBM cells without treatment.

According to the manufacturers' instruction, for in vivo imaging, animals were given the substrate D-luciferin (Caliper) by intraperitoneal injection at 150 mg/Kg in PBS 15 minutes before imaging and then anesthetized (2.5% isofluorane) (8.).

Mice were then placed onto the warmed stage inside the light-tight camera box with continuous exposure to 2% isofluorane. Imaging times ranged from 20 s to 1 min in automatic mode, depending on the tumor growth and time point.

Luminescent measures were performed once a week, starting at the end of the first week after cells inoculation until the sixth week.

The low levels of light emitted from the bioluminescent tumors were detected by the IVIS™ camera system, integrated, digitized, and displayed. Regions of interest (ROI) from displayed images were identified around the tumor sites and were quantified as total flux (photons/s) using Living Image software (Xenogen).

Immunohystochemistry on Tissue Sections:

After 6 weeks mice were sacrificed. Animals sacrificed undergone transcardiac perfusion/fixation with 100 mL of 0.15M NaCl followed by 250 mL of 0.1M potassium phosphate buffer (KBS) containing 4% PFA infused at a pressure of 120 mmHg, using a Watson-Marlow peristaltic pump. Brains were postfixed and cryoprotected as described above.

Hematoxylin and eosin (H&E) staining and immunohistochemistry were performed. Ten-micrometer-thick serial sections were processed as described above. To retrieve human tumor cells in tissue sections, we employed either human specific antibodies as mouse IgG1 anti-human mitochondria (1:50, Chemicon), mouse IgG1 anti-human nuclei (1:100, Chemicon), mouse IgG2a anti-human HLA-abc (1:100, Dako) or we took advantage of luciferase (mouse IgG1 1:25, Invitrogen) or the reporter gene green fluorescent protein (GFP, 1:500, Mol Probes), present in the vector.

Tumor cell proliferation, differentiation, and neovascularization were assessed by immunohistochemistry using antibodies/sera as: rabbit anti-GFAP (1:500, Dako), anti-KI67 (1:200, Novocastra), mouse anti-human PCNA (1:1500, Sigma), rat anti CD147 (1:600, serotech), rabbit anti NG2 (1:300, Chemicon). Tumor volume and extension were calculated by serial reconstruction.

Tissue sections were also stained with the following primary antibodies:
goat anti-human EphA2 (1:50, R&D), monoclonal mouse IgG 1 anti-human EphA2 clone D7 (1:100, Sigma), rabbit polyclonal anti-human ephrinA1 (1:50, Abcam), rabbit anti-human phospho-ephrinB (Tyr324/329) (1:100, Cell Signaling), goat anti-ephrinB2 (1:10, R&D), goat anti-human ephrinB3 (1:10, R&D), rabbit anti phospho (S339) CXCR4 (1:100, Abcam), goat anti-human Wnt5a (1:10, R&D), rabbit anti-human E-cadherin (1:100, Cell Signaling).

Results:

As shown in FIGS. 11A-11F, forty-eight hour exposure of luc-GBM-CSC cells to ephrinA1-Fc or to EphA2-Fc (5.0 μg/mL) in vitro, before transplantation into the striatum of scid/bg mice, dramatically reduces tumor-initiating ability. The bioluminescence monitoring reported in FIG. 11A, FIG. 11B clearly shows a corresponding signal increase from the tumors. GBM tumor growth is strongly inhibited in luc-GBM-CSC bioluminescent lines treated with EphA2-Fc or ephrinA1-Fc. The tumors were monitored once a week, beginning 7 days after cells injection using in vivo imaging. The graph shows mean±s.e.m. in the three groups of six mice. Furthermore, FIG. 11C shows the differences in tumor growth and tumor size detected in vivo following intracranial injection of resting GBM-CSCs and pre-treated with EphA2-Fc or ephrinA1-Fc. Dorsal images taken over time from three representative scid/bgm ice injected are shown. Pseudocolor scale bars were consistent for all images of dorsal views in order to show relative changes at tumor site over time.

By means of confocal images, reported in FIGS. 11D-11F, six weeks following orthotopic implantation, tumors derived from untreated luc-GBM-CSCs FIG. 11D were more extended and invade the brain parenchima more efficiently than those generated by ephrinA1-Fc FIG. 11E and EphA2-Fc FIG. 11F treated cells, as shown by luciferase-specific immunostaining. Tumor size from immunohistochemical images of serially-registered sections were compared with corresponding BLI measurements to determine the extent of correlation (data not shown). Scale bar, 1 mm.

Example 14

Effects of Localized and Direct Microperfusion of EphrinA1-Fc and EphA2-Fc on Pre-Established Orthotopic Tumors A similar approach was used to study tumor growth upon EphA2 modulation in vivo. This could define a clear relationship between the state of activation or expression of the EphA2 receptors and the tumorigenic properties of GBM-CSCs and, particularly, an inverse correlation between these two parameters. This might also determine the possibility of using EphA2 modulation in vivo as a candidate therapeutic tool to tackle the hGBM-TCSC pool in the patients' tumour.
Implantation of Mini-Alzet Pumps Infusing EphrinA1-Fc or EphA2-Fc into the Striatum of scid/bg Mice Ten days after luc-GBM-CSCs orthotopical injection, when tumor is of substantial size without causing any motor or behavioural abnormalities, the intracerebral catheter of a mini-osmotic pump (Alzet) was placed through the same burr hole into the mice striatum.

Alzet pumps operate because of an osmotic pressure difference between a compartment within the pump, called the salt sleeve, and the tissue environment in which the pump is implanted. The high osmolarity of the salt sleeve causes water to enter the pump through the semipermeable membrane, which covers the outer surface of the pump. As the water enters the salt sleeve, it compresses the flexible reservoir, displacing the test solution from the pump at a controlled, predetermined rate.

According to the manufacturers' instruction (brain infusion kit), 1004 of a solution of EphA2-Fc (30 μg) or ephrinA1-Fc (30 μg) in PBS were placed in the reservoire and infused for 14 days (0.25 μL/hour). The delivered doses were 1.8 μg/day.

Animals were closely monitored for signs of toxicity. Tumor formation, extension and volume were indirectly calculated ones/week by sequential images taken with In vivo Lumina analysis (Xenogen) as described above. Infused mice were compared with those of control animals receiving GBM cells without treatment (100 μL of PBS solution).

Two weeks after catheters placement (4 weeks after GBM-CSCs injection) mice were sacrificed. Transcardiac perfusion/fixation, tissue postfixation and inclusion and immunohistochemistry were described in pre-treatment intracranial experiments.

Results:

FIG. 12 shows that continuous administration of ephrinA1-Fc or EphA2-Fc with mini-alzet pumps, implanted into the striatum of scid/bg mice at the cell injection site 7-10 days after GBM CSCs transplantation, (post-treatment) inhibits tumor growth. Luc-GBM-CSCs were injected in the right striatum of scid/bg mice and 14 days thereafter, upon tumors achieved volume, the intracerebral catheter of a mini-osmotic pump was placed through the same burr hole into the mice striatum (arrows: osmotic pump implantation). Tumor bearing mice were infused with EphA2-Fc, ephrinA1-Fc or control vehicle for 14 days with a delivered daily dose of 1.8 μg/day. Bioluminescence monitoring was performed once a week, beginning 7 days after tumor cells implantation. Either EphA2-Fc or ephrinA1-Fc treatment group shows a decreased normalized luminescence value through day 21, in contrast to the increasing luminescence value of control group. Bioluminescence measurements for each mouse were normalized against corresponding readings obtained at the beginning of therapy. The graph shows mean±s.e.m. in the three groups of six mice.

From the above description and the above-noted examples, the advantage attained by the product described and obtained according to the present disclosure are apparent.

In summary, in some embodiments of the present disclosure, an inhibitor of expression and/or activity of an Ephrin receptor for use in the treatment of a brain tumor is described. In some of those embodiments, the tumor is glioblastoma. More particularly the brain tumor can be glioblastoma multiforme. In some embodiments, the treatment can be the therapeutic treatment and/or a prophylactic treatment of a brain tumor recurrence after surgery. In some embodiments, the treatment can inhibit the growth of the brain tumor mass.

In some embodiments, the inhibitor of expression and/or activity of an Ephrin receptor is an inhibitor of cancer stem cell proliferation. In some embodiments, the inhibitor can be selected from the group consisting of SEQ ID NO. 1 and SEQ ID NO. 3.

In some embodiments, at least one inhibitor herein described can be comprised in a composition, and in particular a pharmaceutical composition, together with a suitable vehicle, and in particular together with pharmaceutically acceptable bioactive means. In particular, in the pharmaceutical composition the inhibitor of expression and/or activity of an Ephrin receptor can be an inhibitor of cancer stem cell proliferation and/or cancer stem cell migration. In some embodiments the cancer stem cell is a malignant brain cancer stem cell. In some embodiments, the inhibitor of expression and/or activity of an Ephrin receptor is selected form the group consisting of SEQ ID NO. 1 and SEQ ID NO. 3.

The examples set forth above are provided to give those of ordinary skill in the art a complete disclosure and description of how to make and use the embodiments of the compounds, compositions, systems and methods of the disclosure, and are not intended to limit the scope of what the inventors regard as their disclosure. All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the disclosure is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence. Further, each of the hard copy of the sequence listing submitted herewith and the corresponding computer readable form is incorporated herein by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by preferred embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations which is not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

REFERENCES

1. Alo P L, Visca P, Mazzaferro S, Serpieri D E, Mangoni A, Botti C, Monaco S, Carboni M, Zaraca F, Trombetta G, Di Tondo U (1999) Immunohistochemical study of fatty acid synthase, Ki67, proliferating cell nuclear antigen, and p53 expression in hyperplastic parathyroids. Ann Diagn Pathol 3:287-293.
2. Amendola M, Venneri M A, Biffi A, Naldini L (2005) Coordinate dual-gene transgeness by lentiviral vectors carrying synthetic bidirectional promoters. Nat Biotechnol 23:108-16.
3. Erba E, Bergamaschi D, Bassano L, Damia G, Ronzoni S, Faircloth G T, D'Incalsi M (2001) Ecteinascidin-743 (ET-743), a natural marine compound, with a unique mechanism of action. Eur J Cancer; 37:97-105.
4. Gale N W, Yancopoulos G D (1997) Ephrins and their receptors: a repulsive topic?. Cell Tissue Res 290:227-41.
5. Galli R, Binda E, Orfanelli U, Cipelletti B, Gritti A, De Vitis S, et al. (2004) Isolation and characterization of tumorigenic, stem-like neural precursors from human glioblastoma. Cancer Res; 64(19): 7011-21.
6. Gritti A, Parati E A, Cova L, Frolichsthal P, Galli R, Wanke E, Faravelli L, Morassutti D J, Roisen F, Nickel D D, Vescovi A L (1996) Multipotential stem cells from the adult mouse brain proliferate and self-renew in response to basic fibroblast growth factor. J Neurosci 16:1091-1100.
7. Gritti A, Galli R, A. L. V (2001) Cultures of Stem Cells of the Central Nervous System, Humana Press Edition: S. Fedoroff.
8. Jenkins D E, Hornig Y S, Oei Y, Dusich J and Purchio T (2005) Bioluminescent human breast cancer cell lines that permit rapid and sensitive in vivo detection of mammary tumors and multiple metastases in immune deficient mice. Breast Cancer Res; 5:R444-54.
9. Holland E C (2000) Glioblastoma multiforme: the terminator. Proc Natl Acad Sci USA 97:6242-4.
10. Pennacchietti S, Michieli P, Galluzzo M, Mazzone M, Giordano S and Comoglio P M (2003) Hypoxia promotes invasive growth by transcriptional activation of the met proto oncogene. Cancer Cell 3:347-361.
11. Piccirillo S G, Reynolds B A, Zanetti N, Lamorte G, Binda E, Broggi G, et al. (2006) Bone morphogenetic proteins inhibit the tumorigenic potential of human brain tumor-initiating cells. Nature; 444(7120): 761-5.
12. Stupp R, Mason W P, van den Bent M J, Weller M, Fisher B, Taphoorn M J, Belanger K, Brandes A A, Marosi C, Bogdahn U, Curschmann J, Janzer R C, Ludwin S K, Gorlia T, Allgeier A, Lacombe D, Cairncross J G, Eisenhauer E, Mirimanoff R O (2005) Radiotherapy plus concomitant and adjuvant temozolomide for glioblastoma. N Engl J Med; 352(10):987-96.

13. Vescovi A L, Parati E A, Gritti A, Poulin P, Ferrario M, Wanke E, Frolichsthal-Schoeller P, Cova L, Arcellana-Panlilio M, Colombo A, Galli R (1999) Isolation and cloning of multipotential stem cells from the embryonic human CNS and establishment of transplantable human neural stem cell lines by epigenetic stimulation. Exp Neurol 156:71-83.

The invention claimed is:

1. A pharmaceutical composition comprising a therapeutic amount of at least one inhibitor of an Ephrin receptor expressed by a cancer stem cell derived from a malignant brain tumor, and a pharmaceutically acceptable bioactive agent in a formulation, effective to inhibit expression of the Ephrin receptor, activity of the Ephrin receptor, or a combination of both, wherein the inhibitor has sequence SEQ ID NO. 3.

2. The pharmaceutical composition of claim 1, wherein the inhibitor is an inhibitor of in vitro and in vivo cancer stem cell proliferation.

3. The pharmaceutical composition of claim 1, wherein the inhibitor is an inhibitor of cancer stem cell clonal efficiency.

4. The pharmaceutical composition of claim 1, wherein the inhibitor elicits a pro-differentiation effect on cancer stem cells.

5. The pharmaceutical composition of claim 1, wherein the inhibitor is an inhibitor of in vitro and in vivo cancer stem cell spreading and migration.

6. The pharmaceutical composition of claim 1, wherein the inhibitor is an inhibitor of in vitro and in vivo cancer stem cell tumor-initiating capacity.

7. The pharmaceutical composition of claim 1, wherein the inhibitor depletes the tumor-initiating cell population.

8. A pharmaceutical composition comprising a therapeutic amount of an inhibitor of an Ephrin receptor expressed by a cancer stem cell derived from a malignant brain tumor and a pharmaceutically acceptable bioactive agent in a formulation effective to interact with the malignant brain cancer stem cell Ephrin receptor, wherein the inhibitor has a sequence of SEQ ID NO. 1, wherein the therapeutic amount of the inhibitor in the formulation is effective (i) to inhibit expression of the Ephrin receptor, activity of the Ephrin receptor, or both and (ii) for selectively differentiating the cancer stem cells to a normal phenotype, selectively inhibiting cancer stem cell growth, or both.

9. The pharmaceutical composition of claim 8, wherein the amount of inhibitor provides a cellular concentration of 0.001 to 0.5 μg/mL.

10. A method to treat a brain tumor in an individual, the method comprising administering to the individual an effective amount of an inhibitor of expression and/or activity of an Ephrin receptor in the pharmaceutical composition of claim 1.

11. The method of claim 10, wherein the tumor is a glioblastoma.

12. The method of claim 10, wherein the tumor is glioblastoma multiforme.

13. The method of claim 10, wherein the treatment is a therapeutic treatment of brain tumor recurrence after surgery.

14. The method of claim 10, wherein the effective amount is administered to inhibit the growth of a brain tumor mass.

15. The method of claim 10, wherein the inhibitor is an inhibitor of in vitro and in vivo cancer stem cell proliferation.

* * * * *